US012605354B2

(12) United States Patent
Streeper et al.

(10) Patent No.: US 12,605,354 B2
(45) Date of Patent: Apr. 21, 2026

(54) AZELAIC ACID ESTERS IN THE TREATMENT OR PREVENTION OF DYSLIPIDEMIA AND ASSOCIATED CONDITIONS

(71) Applicant: NEW FRONTIER LABS, LLC, San Antonio, TX (US)

(72) Inventors: Robert T. Streeper, San Antonio, TX (US); Elzbieta Izbicka, San Antonio, TX (US)

(73) Assignee: NEW FRONTIER LABS, LLC, San Antonio, TX (US)

( * ) Notice: Subject to any disclaimer, the term of this patent is extended or adjusted under 35 U.S.C. 154(b) by 94 days.

(21) Appl. No.: 17/179,935

(22) Filed: Feb. 19, 2021

(65) Prior Publication Data

US 2021/0251939 A1     Aug. 19, 2021

Related U.S. Application Data

(60) Provisional application No. 62/978,785, filed on Feb. 19, 2020.

(51) Int. Cl.
| | |
|---|---|
| *A61K 31/225* | (2006.01) |
| *A61K 9/00* | (2006.01) |
| *A61P 3/06* | (2006.01) |
| *A61P 3/10* | (2006.01) |

(52) U.S. Cl.
CPC .......... *A61K 31/225* (2013.01); *A61K 9/0053* (2013.01); *A61P 3/06* (2018.01); *A61P 3/10* (2018.01)

(58) Field of Classification Search
None
See application file for complete search history.

(56) References Cited

U.S. PATENT DOCUMENTS

| | | | |
|---|---|---|---|
| 10,251,857 B2 | 4/2019 | Streeper et al. | |
| 11,026,912 B2 | 6/2021 | Streeper et al. | |
| 2017/0304252 A1* | 10/2017 | Streeper ................. | A61K 45/06 |
| 2018/0207120 A1 | 7/2018 | Lee et al. | |

FOREIGN PATENT DOCUMENTS

| | | |
|---|---|---|
| WO | 2006/074379 A2 | 7/2006 |
| WO | 2013/158541 A1 | 10/2013 |
| WO | 2017/184767 A1 | 10/2017 |

OTHER PUBLICATIONS

Group DPPR, "Long-term Effects of Metformin on Diabetes Prevention: Identification of Subgroups That Benefited Most in the Diabetes Prevention Program and Diabetes Prevention Program Outcomes Study", Diabetes Care, 2019, pp. 601-608, vol. 42(4).

Bodmer et al., "Metformin, sulfonylureas, or other antidiabetes drugs and the risk of lactic acidosis or hypoglycemia: a nested case-control analysis", Diabetes Care, 2008, pp. 2086-2091, vol. 31(11).
Lin et al., "Effect of metformin monotherapy on serum lipid profile in statin-naive individuals with newly diagnosed type 2 diabetes mellitus: a cohort study", PeerJ, 2018, pp. 1-10, 6:e4578.
Mccreight et al., "Metformin and the gastrointestinal tract", Diabetologia, 2016, pp. 426-435, vol. 59(3).
Yerevanian et al., "Metformin: Mechanisms in Human Obesity and Weight Loss", Curr Obes Rep., 2019, pp. 156-164, vol. (2).
Luo et al., "Metformin in patients with and without diabetes: a paradigm shift in cardiovascular disease management", Cardiovasc Diabetol, 2019, pp. 1-9, vol. 18(1):54.
Courtois et al., "The therapeutic potential of metformin in gastric cancer", Gastric Cancer, 2019, pp. 653-662, vol. 22(4).
Barzilai et al., "Metformin as a Tool to Target Aging", Cell Metab., 2016, pp. 1060-1065, vol. 23(6).
Kulkarni et al., "Metformin regulates metabolic and nonmetabolic pathways in skeletal muscle and subcutaneous adipose tissues of older adults", Aging Cell, 2018, pp. 1-5, vol. 17(2).
Lemieux et al., "Total Cholesterol/HDL cholesterol ratio vs LDL cholesterol/HDL cholesterol ratio as indices of Ischemic heart disease risk in men: the Quebec Cardiovascular Study", Arch Intern Med., 2001, pp. 2685-2692, vol. 161(22).
Wang et al., "Higher non-HDL-cholesterol to HDL-cholesterol ratio linked with increased nonalcoholic steatohepatitis", Lipids in Health and Disease, 2018, pp. 1-6, vol. 17(1):67.
Ertunc et al., "Lipid signaling and lipotoxicity in metaflammation: indications for metabolic disease pathogenesis and treatment", J Lipid Res., 2016, pp. 2099-2114, vol. 57(12).
Speliotes et al., "Treatment of Dyslipidemia in Common Liver Diseases", Clin Gastroenterol Hepatol., 2018, pp. 1189-1196, vol. 16(8).
Binesh et al., "Pharmacological management of metabolic syndrome and its lipid complications", Daru., 2010, pp. 146-154, vol. 18(3).
Nicholls et al., "Statins, high-density lipoprotein cholesterol, and regression of coronary atherosclerosis", JAMA, 2007, pp. 499-508, vol. 297(5).
Sattar et al., "Statins and risk of incident diabetes: a collaborative meta-analysis of randomised statin trials", Lancet, 2010, pp. 735-742, vol. 375(9716).
Seshadri et al., "Statins exacerbate glucose intolerance and hyperglycemia in a high sucrose fed rodent model", Sci Rep., 2019, pp. 1-9, vol. 9(1):8825.
Golomb et al., "Statin adverse effects: a review of the literature and evidence for a mitochondrial mechanism", Am J Cardiovasc Drugs, 2008, pp. 373-418, vol. 8(6).
Fessler et al., "Intracellular lipid flux and membrane microdomains as organizing principles in inflammatory cell signaling", J Immunol., 2011, pp. 1529-1535, vol. 187(4).

(Continued)

*Primary Examiner* — Po-Chih Chen

(74) *Attorney, Agent, or Firm* — Pillsbury Winthrop Shaw Pittman, LLP

(57) ABSTRACT

Pharmaceutical compositions comprising a $C_1$-$C_4$ alkyl ester azelate, such as diethyl azelate (DEA), dimethyl azelate (DMA), di-isopropyl azelate (DiPA), di-isobutyl azelate (DiBuA), and di-2-pentyl azelate (D2PA), and methods of, inter alia, improving abnormal lipid levels and treating or preventing dyslipidemias and/or diseases of conditions associated therewith comprising administering to a subject such pharmaceutical compositions, are provided.

5 Claims, 20 Drawing Sheets

(56) References Cited

OTHER PUBLICATIONS

Schoeniger et al., "The Impact of Membrane Lipid Composition on Macrophage Activation in the Immune Defense against Rhodococcus equi and Pseudomonas aeruginosa", Int J Mol Sci., 2011, pp. 7510-7528, vol. 12(11).

Goluszko et al., "Membrane cholesterol: a crucial molecule affecting interactions of microbial pathogens with mammalian cells", Infect Immun., 2005, pp. 7791-7996, vol. 73(12).

Owen et al., "Decreased erythrocyte membrane fluidity and altered lipid composition in human liver disease", J Lipid Res., 1982, pp. 124-132, vol. 23(1).

Kojima, "Molecular aspects of the plasma membrane in tumor cells", Nagoya J Med Sci., 1993, pp. 1-18, vol. 56.

Pilon, "Revisiting the membrane-centric view of diabetes" Lipids Health Dis., 2016, pp. 1-6, vol. 15(1).

Lodish et al., "Section 15.1—Diffusion of Small Molecules across Phospholipid Bilayers", Molecular Cell Biology. 4 ed. New York, W. H. Freeman, 2000, 3 pages.

Walter et al., "Permeability of small nonelectrolytes through lipid bilayer membranes", J Membr Biol., 1986, pp. 207-217, vol. 90(3).

Patent Cooperation Treaty, International Search Report and Written Opinion issued in PCT/IB2021/051451, May 25, 2021, pp. 1-12.

Al-Marabeh, S. et al., 'A prodrug approach to enhance azelaic acid percutaneous availability, Pharmaceutical Development and Technology, 2016, pp. 1-9.

Muthulakshmi, S. et al., 'Efficacy of azelaic acid on hepatic key enzymes of carbohydrate metabolism in high fat diet induced type 2 diabetic mice', Biochimie, 2013, vol. 95, pp. 1239-1244.

Muthulakshmi, S. et al., 'Gene expression profile of high-fat diet-fed C57BL/6J mice: in search of potential role of azelaic acid', J. Physiol. Biochem., 2015, vol. 71, pp. 29-42.

Streeper, R. T. et al., 'Oral Azelaic Acid Ester Decreases Markers of Insulin Resistance in Overweight Human Male Subjects', In vivo, May-Jun. 2020, pp. 1173-1186, vol. 34(3).

Esposito et al., "Metabolic syndrome and risk of cancer: a systematic review and meta-analysis. Diabetes Care", 2012, pp. 2402-2411, vol. 35(11).

Moghaddam et al., "Obesity and risk of colorectal cancer: meta-analysis of 31 studies with 70,000 events", Cancer Epidemiol Biomarkers Prev., 2007, pp. 2533-2547, vol. 16(12).

Huang et al., "Prediabetes and the risk of cancer: a meta-analysis. Diabetologia", 2014, pp. 2261-2269, vol. 57(11).

Koo et al., "The Incremental Risk of Pancreatic Cancer According to Fasting Glucose Levels: Nationwide Population-Based Cohort Study", The Journal of Clinical Endocrinologu and Metabollism, 2019, pp. 4594-4599.

Giovannucci et al., "Diabetes and cancer: a consensus report", Diabetes Care, 2010, pp. 1674-1685, vol. 33(7).

Hernandez et al., "Insulin resistance and endometrial cancer risk: A systematic review and metaanalysis", Eur J Cancer, 2015, pp. 2747-2758, vol. 51(18).

Caputo et al., "From chronic overnutrition to metaflammation and insulin resistance: adipose tissue and liver contributions" FEBS Letters, 2017, pp. 3061-3088, vol. 591(19).

Christ et al., "The Western lifestyle has lasting effects on metaflammation", Nat Rev Immunol., 2019, pp. 267-268, vol. 19(5).

Boden et al., oden G, "Excessive caloric intake acutely causes oxidative stress, GLUT4 carbonylation, and insulin resistance in healthy men", Sci Transl Med. ,2015, pp. 1-19, vol. 7(304).

Lustig, Fructose: it's "alcohol without the buzz", Adv Nutr., 2013, pp. 226-235, vol. 4(2).

Shelmet et al., "Ethanol causes acute inhibition of carbohydrate, fat, and protein oxidation and insulin resistance", J Clin Invest., 1988, pp. 1137-1145, vol. 81(4).

Kim et al., "Chronic alcohol consumption, type 2 diabetes mellitus, insulin-like growth factor-I (IGF-I), and growth hormone (GH) in ethanol-treated diabetic rats", Life Sci., 2013, pp. 778-782.

Hirakawa et al., "Relationship between Alcohol Intake and Risk Factors for Metabolic Syndrome in Men", Intern Med., 2015, pp. 2139-2145, vol. 54(17).

Carr et al., "Temporal effects of ethanol consumption on energy homeostasis, hepatic steatosis, and insulin sensitivity in mice", Alcohol Clin Exp Res., 2013, pp. 1091-1099, vol. 37(7).

Sterrett et al., "Type 2 Diabetes Medication Review", Am J Med Sci., 2016, pp. 342-355, vol. 351(4).

Smilowitz et al., "The human milk metabolome reveals diverse oligosaccharide profiles", J Nutr., 2013, pp. 1709-1718, vol. 143(11).

Matsubara et al., "Metabolomics identifies an inflammatory cascade involved in dioxin- and diet-induced steatohepatitis", Cell Metab., 2012, pp. 634-644, vol. 16(5).

Fan et al., "Characterization of key odorants in Chinese chixiang aroma-type liquor by gas chromatography-olfactometry, quantitative measurements, aroma recombination, and omission studies", J Agric Food Chem, 2015, pp. 3660-3668, vol. 63(5).

Saerens et al., "Parameters affecting ethyl ester production by *Saccharomyces cerevisiae* during fermentation", Appl Environ Microbiol., 2008, pp. 454-461, vol. 74(2).

Kostelenos et al., "Olive tree history and evolution", In: Kiritsakis A, Shahidi F, editors, Olives and olive oil as functional foods, Oxford, UK: John Wiley & Sons Ltd., 2017. pp. 1-12.

Rahmani et al., "Food hazards and quality control in table olive processing with a special reference to functional compounds", In: Kiritsakis A, Shahidi F, editors, Olives and olive oil as functional foods, Oxford, UK: John Wiley & Sons Ltd; 2017. p. 347-352.

Hymowitz, "The history of the soybean. Soybeans Chemistry, Production, Processing and Utilization: AOCS Press", 2008. pp. 1-31.

Kwon et al., "Antidiabetic effects of fermented soybean products on type 2 diabetes", Nutr Res., 2010, pp. 1-13, vol. 30(1).

Kim et al., "Components in Commercial Douchi a Chinese Fermented Black Bean Product by Supercritical Fluid Extraction", J Food Sci Nutr, 2008, pp. 12-17, vol. 13.

European Food Safety Authority, The EFSA Journal, 2009, pp. 1-114, vol. 934.

Singh et al. "Surrogate markers of insulin resistance: A review", World J Diabetes, 2010, pp. 36-47.

Bonora et al., "The pros and cons of diagnosing diabetes with A1C", Diabetes Care, May 2011, pp. S184-S190, vol. 34 Supplement 2.

Tyrer et al., "Sampling in epidemiological research: issues, hazards and pitfalls", BJPsych Bull, 2016, pp. 57-60, vol. 40(2).

Yeung et al., "Longitudinal study of insulin resistance and sex hormones over the menstrual cycle: the BioCycle Study", J Clin Endocrinol Metab., 2010, pp. 5435-5442, vol. 95(12).

Ibrahim et al., "Study Design Selection in Early Clinical Anti-Hyperglycemic Drug Development: A Simulation Study of Glucose Tolerance Tests", CPT Pharmacometrics Syst Pharmacol, 2018, pp. 432-441, vol. 7(7).

Warnick et al., Standardization of Measurements for Cholesterol, Triglycerides, and Major Lipoproteins Labmedicine. 2008, pp. 481-490, vol. 39(8).

Sherifali et al., "The effect of oral antidiabetic agents on A1C levels: a systematic review and meta-analysis", Diabetes Care, 2010, pp. 1859-1864, vol. 33(8).

Brambilla et al., "Normal fasting plasma glucose and risk of type 2 diabetes", Diabetes Care, 2011, pp. 1372-1374, vol. 34(6).

Tuso et al., "Prediabetes and lifestyle modification: time to prevent a preventable disease", Perm J., 2014, pp. 88-93, vol. 18(3).

Brunzell et al., "Relationships between fasting plasma glucose levels and insulin secretion during intravenous glucose tolerance tests", J Clin Endocrinol Metab., 1976, pp. 222-229, vol. 42(2).

Gaitonde et al. "A Comprehensive Review of Novel Drug-Disease Models in Diabetes Drug Development", Clinical Pharmacokinetics, 2016, pp. 769-788, vol. 55(7).

Thomas, "Glycemic exposure, glycemic control, and metabolic karma in diabetic complications", Adv Chronic Kidney Dis., 2014, pp. 311-317, vol. 21(3).

Gerich, "The importance of tight glycemic control", Am J Med., 2005, pp. 7S-11S, vol. 118 (Suppl 9A).

Bluher et al. Leptin in humans: lessons from translational research, "American Journal of Clinical Nutrition", 2009, pp. 991S-997S, vol. 89(3).

(56) References Cited

OTHER PUBLICATIONS

Wang et al., "Non-HDL-cholesterol to HDL-cholesterol ratio is a better predictor of new-onset non-alcoholic fatty liver disease than non-HDL-cholesterol: a cohort study", Lipids Health Dis., 2018, pp. 1-8, vol. 17(196).
Donath et al., "Mechanisms of beta-cell death in type 2 diabetes", Diabetes, 2005, pp. S108-S113, vol. 54 (Suppl 2).
Eriksson et al. "Shortterm effects of metformin in type 2 diabetes", Diabetes Obes Metab., 2007, pp. 483-489, vol. 9 (4).
Salpeter et al., "Meta-analysis: metformin treatment in persons at risk for diabetes mellitus", Am J Med., 2008, pp. 149-157, vol. 121(2).
India Intellectual Property Office, Official Action issued in IN Application No. 202217052812, Oct. 15, 2025, pp. 1-8.

* cited by examiner

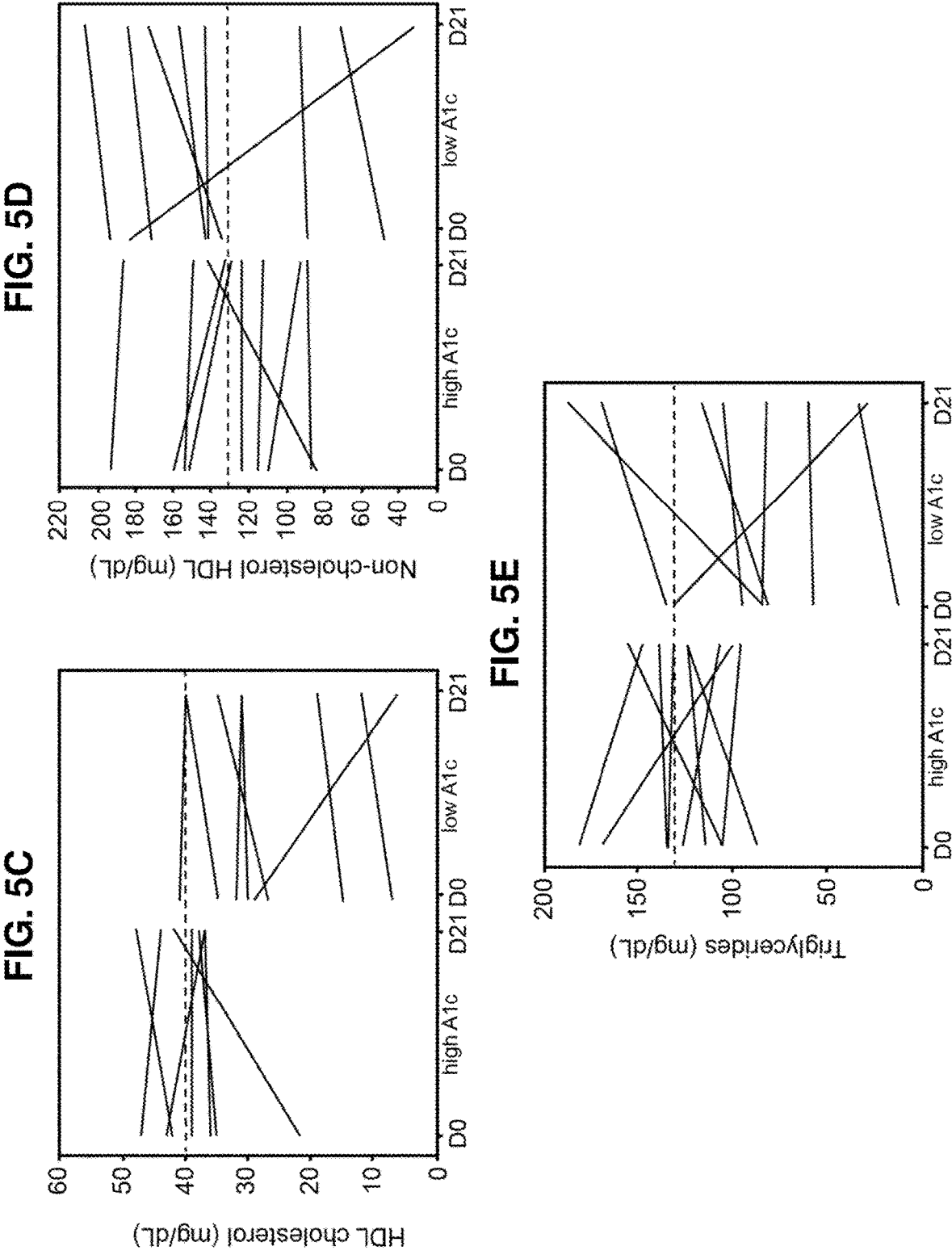

Figure 8

Blood Lipid Levels vs. Buccal DEA Dose

Figure 15

DEA Buccal Delivery

| DEA | Total Cholesterol | HDL | Triglycerides | Calc LDL | TC/HDL |
|-----|-------------------|-----|---------------|----------|--------|
| 0 | 237.8 | 54.2 | 174.8 | 148.6 | 4.5 |
| 0.5 | 192.5 | 66.3 | 125.3 | 109.3 | 2.9 |
| 1 | 138.2 | 60.6 | 91.2 | 59.4 | 2.3 |
| 2 | 202.2 | 72.4 | 114.6 | 106.8 | 2.8 |
| 4 | 194.0 | 63.6 | 140.2 | 102.2 | 3.0 |

DEA Gastric Delivery

| DEA | Total Cholesterol | HDL | Triglycerides | Calc LDL | TC/HDL |
|-----|-------------------|-----|---------------|----------|--------|
| 0 | 237.8 | 54.2 | 174.8 | 148.6 | 4.5 |
| 0.1 | 202.4 | 59.2 | 95.6 | 124.0 | 3.4 |
| 0.25 | 179.6 | 60.8 | 81.4 | 99.2 | 3.0 |
| 0.5 | 209.4 | 67.4 | 93.6 | 123.4 | 3.1 |
| 1 | 207.0 | 63.8 | 103.2 | 122.2 | 3.3 |

Figure 16

DEA Buccal Delivery

| DEA | Glucose 0h | Glucose 1h | Glucose 2h | Glucose 4 h |
|-----|-----------|-----------|-----------|------------|
| 0 | 133.4 | 265.0 | 182.2 | 115.0 |
| 0.5 | 108.8 | 184.6 | 110.4 | 87.0 |
| 1 | 133.2 | 234.2 | 103.4 | 105.4 |
| 2 | 142.4 | 250.8 | 177.8 | 126.6 |
| 4 | 143.2 | 220.0 | 146.8 | 102.0 |

DEA Gastric Delivery

| DEA | Glucose 0h | Glucose 1h | Glucose 2h | Glucose 4 h |
|-----|-----------|-----------|-----------|------------|
| 0 | 133.4 | 265.0 | 182.2 | 115.0 |
| 0.1 | 132.6 | 222.0 | 139.0 | 122.4 |
| 0.25 | 120.2 | 199.2 | 136.2 | 115.2 |
| 0.5 | 120.8 | 216.6 | 144.0 | 104.0 |
| 1 | 129.4 | 229.0 | 143.8 | 131.0 |

Figure 17

Comparison of doses

| DEA dose | Total Cholesterol | HDL | Triglycerides | Calc LDL | TC/HDL |
|---|---|---|---|---|---|
| 1 mg/kg buccal | 138.2 | 60.6 | 91.2 | 59.4 | 2.3 |
| 0.25 mg/kg gastric | 179.6 | 60.8 | 81.4 | 99.2 | 3.0 |
| T test | 0.021 | 0.972 | 0.303 | 0.229 | 0.049 |

Comparison of doses

| DEA dose | Glucose 0h | Glucose 1h | Glucose 2h | Glucose 4 h |
|---|---|---|---|---|
| 0.5mg/kg buccal | 108.8 | 184.6 | 110.4 | 87.0 |
| 0.25 mg/kg gastric | 120.2 | 199.2 | 136.2 | 115.2 |
| T test | 0.019 | 0.291 | 0.173 | 0.040 |

Protein Activity as a Function of Membrane Fluidity

% protein function

100

0 soft hard

Membrane fluidity

"Too soft"

"Too hard"

AZELAIC ACID ESTERS IN THE TREATMENT OR PREVENTION OF DYSLIPIDEMIA AND ASSOCIATED CONDITIONS

RELATED APPLICATIONS

This patent application claims priority to U.S. Provisional Patent Application No. 62/978,785, filed Feb. 19, 2020, entitled "AZELAIC ACID ESTERS IN THE TREATMENT OR PREVENTION OF DYSLIPIDEMIA AND ASSOCIATED CONDITIONS" naming inventors Robert T. STREEPER and Elzbieta IZBICKA. The entire content of the foregoing patent application is incorporated herein by reference.

BACKGROUND

Provided are pharmaceutical compositions and methods for, inter alia, improving abnormal lipid levels and treating or preventing dyslipidemias and/or diseases of conditions associated therewith, including diseases of lipid signaling, comprising administering to a subject such pharmaceutical compositions. Such pharmaceutical compositions comprise a $C_1$-$C_4$ alkyl ester azelate, such as diethyl azelate (DEA), dimethyl azelate (DMA), di-isopropyl azelate (DiPA), di-isobutyl azelate (DiBuA), or di-2-pentyl azelate (D2PA).

Dyslipidemias are disorders of lipoprotein metabolism, lipid transport and clearance, and/or over- or under-consumption. These disorders may be manifested by abnormal or aberrant blood total cholesterol level or concentration, low-density lipoprotein (LDL) level or concentration, triglyceride level or concentration, and/or high-density lipoprotein (HDL) level or concentration. While the term describes a wide range of conditions, the most common forms of dyslipidemia involve one or more of the following: elevated levels of low-density lipoproteins (LDL), or "bad cholesterol"; low levels of high-density lipoproteins (HDL), or "good cholesterol"; elevated levels of triglycerides; high cholesterol, which refers to high LDL and triglyceride levels; elevated LDL-to-HDL (LDL/HDL) ratio, and/or elevated non-cholesterol HDL-to-HDL (non-cholesterol HDL/HDL) ratio.

Dyslipidemias, such as hypertriglyceridemia, hyperlipidemia, hypercholesterolemia, and the like, have also been shown to be associated with and/or cause pancreatitis, hepatomegaly, hypertension, overweight, and obesity. Numerous studies have also documented a causal relationship between elevated or aberrant serum cholesterol levels and the genesis of cardiovascular disease, such as atherosclerosis, arteriosclerosis, coronary heart disease, stroke, ischemic heart disease, and other comorbidities. A strong association between dyslipidemia and insulin resistance has also been observed, both of which are key components of metabolic syndrome, a constellation of metabolic factors including central obesity, dyslipidemia, hypertension, and either impaired fasting glucose or type II diabetes that in turn increase the risk for other metabolic derangements including cardiovascular disease, fatty liver disease, nonalcoholic steatohepatitis (NASH), and alcoholic steatohepatitis (ASH).

The Western diet combined with a sedentary lifestyle has been shown to result in chronic metabolic inflammation (8, 9), insulin resistance, and obesity. A diet consisting of ~50% carbohydrates with high levels of fructose has been shown to induce insulin resistance in healthy non-obese men within 2-7 days (10). The detrimental health effects of dietary fructose are similar to those of ethanol (11). The diabetogenic effects of ethanol consumption, either acute (12) or chronic (13), strongly correlate with the development of insulin resistance in a dose-dependent manner (14, 15).

Despite the high prevalence and coincidence of dyslipidemias in the setting of insulin resistance, prediabetes, type II diabetes, metabolic syndrome and other comorbidities associated with metabolic syndrome, treatments and therapies designed to reduce insulin resistance and/or to treat prediabetes or type II diabetes often to not satisfactorily address coincident, abnormal lipid levels and/or treat coincident dyslipidemias or any of the other comorbidities associated with abnormal lipid levels, such as cardiovascular disease, such as atherosclerosis, arteriosclerosis, coronary heart disease, stroke, ischemic heart disease, and the like. Similarly, subjects with overweight or obesity often experience abnormal lipid levels and/or dyslipidemia, with or without coincident insulin resistance, prediabetes, and/or type II diabetes, and nonetheless have or are at risk of acquiring, many of these comorbid metabolic and cardiovascular diseases or conditions. Accordingly, lipid lowering and/or lipid improving therapies and treatments are desirable in such overweight or obese subjects independent—or in lieu of—any treatments for insulin resistance, prediabetes, or type II diabetes.

The current clinical treatment of dyslipidemia represents the outcome of a large body of fundamental basic science research on lipids, lipid metabolism, and the effects of different lipids on cellular components of the artery, inflammatory cells, and platelets. In general, low density lipids activate intracellular pathways to increase local and systemic inflammation, monocyte adhesion, endothelial cell dysfunction and apoptosis, and smooth muscle cell proliferation, resulting in foam cell formation. Accordingly, dyslipidemias may be viewed in certain respects as inflammatory disorders, as well as disorders that may be associated with or exacerbate inflammatory conditions.

Various strategies are currently employed in the management of dyslipidemias both independently and in the setting of other associated diseases or conditions, such as insulin resistance, type II diabetes, and the like. With regard to treating dyslipidemias, strategies include dietary changes aimed at reducing consumption of foods high in cholesterol and fats, as well as prescription of one or more medications aimed to improve elevated cholesterol, LDL, and/or triglyceride levels. Such medications include: statins, such as atorvastatin, fluvastatin, lovastatin, pravastatin, simvastatin, and rosuvastatin; fibrates, such as clofibrate, gemfibrozil, fenofibrate; niacin; and leptins or leptin agonists, including metreleptin.

Similar to strategies for treating dyslipidemias, insulin resistance and type II diabetes are often first managed by increasing physical exercise and taking on dietary changes aimed at decreasing caloric-primarily carbohydrate-consumption. If these measures do not sufficiently lower blood sugar and or A1c levels, medications are designed to effect blood sugar and/or A1c levels are typically employed. The most commonly used drug, insulin in various formulations, is used to lower blood glucose. Metformin, a biguanide drug, may also be prescribed, which inhibits glucose production and release by the liver. By cutting off the glucose supply, metformin increases insulin sensitivity. Other therapies include administration of: insulin sensitizers, such as thiazolidinediones, including pioglitazone and rosiglutozone; glucagonlike peptide-1 (GLP-1) agonists such as an exendin, exenatide, liraglutide, lixisenatide, albiglutide, dulaglutide, semaglutide; amylin agonists, such as pramlintide; leptins or leptin agonists, such as metreleptin; sodium-glucose co-transporter 2 (SGLT2) inhibitors, such as cana-gliflozin, dapagliflozin, empagliflozin, and ertuglifozin.

Azelates, such as $C_1$-$C_4$ alkyl ester azelates, including diethyl azelate (DEA), are metabolic products occurring naturally in humans and other mammals [17, 18]. Azelates are also present in grains and grain derived products including liquor and in fermented foods due to bacterial degradation of acyl glycerol fatty acids and esterification of the resulting medium chain fatty acids [20]. Fermentation of olives by Lactobacilli to render them edible has been practiced for at least 6 millennia in the Mediterranean basin [21]. The Lactobacilli destroy bitter alkaloids contained in the olive fruits converting them to table olives [22]. In addition, the Lactobacilli ferment some of the oleic acid contained in the olives into azelaic acid and azelates. The rind of olives also contains appreciable quantities of azelaic acid. Fermented soybean products, produced by humans for over 3 millennia [23], may help prevent or attenuate the progression of T2D [24]. Azelaic acid and azelate ethyl esters are also present in douchi, a fermented black bean product [25].

Although not currently used as drugs, azelates and similar fatty acid esters are used as food additives, lubricants and plasticizers. DEA is approved as a flavoring additive in the European Union [26, 27] and diethylhexyl azelate is approved for food contact packaging in the United States. A closely related ester, diethyl sebacate, which differs from DEA in that sebacic acid is one methylene unit longer than azelaic acid, is on the list of Generally Regarded As Safe (GRAS) compounds and the Inactive Ingredients List of the United States Food and Drug Administration (FDA).

SUMMARY

In some aspects, which may be combined with one or more other aspects or embodiments, provided are methods of improving one or more abnormal lipid levels in a subject, comprising administering to the subject a pharmaceutical composition comprising an effective amount of a $C_1$-$C_4$ alkyl ester azelate to improve the one or more abnormal lipid levels. In some embodiments, such methods comprise administering a pharmaceutical composition comprising a $C_1$-$C_4$ alkyl ester azelate selected from the group consisting of: diethyl azelate (DEA); dimethyl azelate (DMA), di-isopropyl azelate (DiPA), di-isobutyl azelate (DiBuA), and di-2-pentyl azelate (D2PA). In some embodiments, such methods comprise administering a pharmaceutical composition comprising DEA.

In some aspects, which may be combined with one or more other aspects or embodiments, provided are methods of lowering an elevated LDL level, elevating a diminished HDL level, lowering an elevated triglyceride level, lowering an elevated cholesterol/HDL, lowering an elevated LDL/HDL, lowering an elevated LDL/triglyceride, or lowering an elevated non-cholesterol HDL/HDL in a subject, the methods comprising administering to the subject an effective amount of a pharmaceutical composition comprising a $C_1$-$C_4$ alkyl ester azelate. In some embodiments, such methods comprise administering a pharmaceutical composition comprising a $C_1$-$C_4$ alkyl ester azelate selected from the group consisting of: DEA; DMA; DiPA; DiBuA; and D2PA. In some embodiments, such methods comprise administering a pharmaceutical composition comprising DEA.

In some aspects, which may be combined with one or more other aspects or embodiments, provided are methods of treating or preventing a dyslipidemia or a disease or condition associated with a dyslipidemia, in a subject comprising administering to the subject a pharmaceutical composition comprising a $C_1$-$C_4$ alkyl ester azelate in an amount effective to treat or prevent the dyslipidemia, or a disease or condition associated with a dyslipidemia, in the subject. In some embodiments, the dyslipidemia comprises at least one of the following: elevated LDL level, diminished HDL level, elevated triglyceride level, elevated cholesterol/HDL, elevated LDL/HDL, elevated LDL/triglyceride, and elevated non-cholesterol HDL/HDL. In some embodiments, such methods comprise administering a pharmaceutical composition comprising a $C_1$-$C_4$ alkyl ester azelate selected from the group consisting of: DEA; DMA; DiPA; DiBuA; and D2PA. In some embodiments, such methods comprise administering a pharmaceutical composition comprising DEA.

In some aspects, which may be combined with one or more other aspects or embodiments, provided are methods of treating or preventing a dyslipidemia or a disease or condition associated with a dyslipidemia in a subject comprising administering to the subject a pharmaceutical composition comprising an effective amount of $C_1$-$C_4$ alkyl ester azelate, wherein the disease or condition associated with the dyslipidemia comprises one or more of the following: hyperlipidemia, hypertriglyceridemia, hypercholesterolemia, mixed hyperlipidemia, familial combined hyperlipidemia, lipodystrophy, cardiovascular disease, hypertension, stroke, atherosclerosis, arteriosclerosis, coronary artery disease, NASH, ASH, fatty liver disease, NAFLD, hepatomegaly, pancreatitis, metabolic syndrome, insulin resistance, prediabetes, type II diabetes, overweight, and obesity. In some embodiments, such methods comprise administering a pharmaceutical composition comprising a $C_1$-$C_4$ alkyl ester azelate selected from the group consisting of: DEA; DMA; DiPA; DiBuA; and D2PA. In some embodiments, such methods comprise administering a pharmaceutical composition comprising DEA.

In some aspects, which may be combined with one or more other aspects or embodiments, methods provided herein comprise administering to a subject a $C_1$-$C_4$ alkyl ester azelate at a dosage in a range from about 0.1 milligram/kilogram/day (mg/kg/day) to about 10 mg/kg/day, about 0.2 mg/kg/day to about 9.5 mg/kg/day, about 0.3 mg/kg/day to about 9 mg/kg/day, 0.4 mg/kg/day to about 8.5 mg/kg/day, about 0.5 mg/kg/day to about 8 mg/kg/day, about 0.6 mg/kg/day to about 7.5 mg/kg/day, about 0.7 mg/kg/day to about 7.0 mg/kg/day, about 0.8 mg/kg/day to about 6.5 mg/kg/day, about 0.9 mg/kg/day to about 6.0 mg/kg/day, about 1.0 mg/kg/day to about 5.5 mg/kg/day, about 1.0 mg/kg/day to about 5.0 mg/kg/day, about 0.1 mg/kg/day to about 5.0 mg/kg/day, about 0.25 mg/kg/day to about 5.0 mg/kg/day, about 0.1 mg/kg/day to about 4.0 mg/kg/day, about 0.25 mg/kg/day to about 4.0 mg/kg/day, about 0.5 mg/kg/day to about 4.0 mg/kg/day, about 0.75 to about 4.0 mg/kg/day, or about 0.25 mg/kg/day to about 3.0 mg/kg/day, about 0.25 mg/kg/day to about 2.5 mg/kg/day, about 0.25 mg/kg/day to about 2.0 mg/kg/day, about 0.25 mg/kg/day to about 1.5 mg/kg/day, or about 0.25 mg/kg/day to about 1.5 mg/kg/day. In some embodiments, the $C_1$-$C_4$ alkyl ester azelate is orally administered at such dosage ranges.

In some aspects, which may be combined with one or more other aspects or embodiments, methods provided herein comprise administering to a subject a pharmaceutical composition comprising $C_1$-$C_4$ alkyl ester azelate at a dosage of about 0.1 mg/kg/day, about 0.2 mg/kg/day, about 0.3 mg/kg/day, about 0.4 mg/kg/day, about 0.5 mg/kg/day, about 0.6 mg/kg/day, about 0.7 mg/kg/day, about 0.8 mg/kg/day, about 0.9 mg/kg/day, about 1.0 mg/kg/day, about 1.1 mg/kg/day, about 1.2 mg/kg/day, about 1.3 mg/kg/day, about 1.4 mg/kg/day, about 1.5 mg/kg/day, about 1.6 mg/kg/day, about 1.7 mg/kg/day, about 1.8 mg/kg/day, about 1.9 mg/kg/day, about 2.0 mg/kg/day, about 2.1 mg/kg/day, about 2.2 mg/kg/day, about 2.3 mg/kg/day, about 2.4 mg/kg/day, about 2.5 mg/kg/day, about 2.6 mg/kg/day, about 2.7 mg/kg/day, about 2.8 mg/kg/day, about 2.9 mg/kg/day, about 3.0 mg/kg/day, about 3.1 mg/kg/day, about 3.2 mg/kg/day, about 3.3 mg/kg/day, about 3.4 mg/kg/day, about 3.5 mg/kg/day, about 3.6 mg/kg/day, about 3.7 mg/kg/day, about 3.8 mg/kg/day, about 3.9 mg/kg/day, about 4.0 mg/kg/day, about 4.1 mg/kg/day, about 4.2 mg/kg/day, about 4.3 mg/kg/day, about 4.4 mg/kg/day, about 4.5 mg/kg/day, about 4.6 mg/kg/day, about 4.7 mg/kg/day, about 4.8 mg/kg/day, about 4.9 mg/kg/day, 5.0 mg/kg/day, about 5.1 mg/kg/day, about 5.2 mg/kg/day, about 5.3 mg/kg/day, about 5.4 mg/kg/day, about 5.5 mg/kg/day, about 5.6 mg/kg/day, about 5.7 mg/kg/day, about 5.8 mg/kg/day, about 5.9 mg/kg/day, about 6.0 mg/kg/day, about 6.1 mg/kg/day, about 6.2 mg/kg/day, about 6.3 mg/kg/day, about 6.4 mg/kg/day, about 6.5 mg/kg/day, about 6.6 mg/kg/day, about 6.7 mg/kg/day, about 6.8 mg/kg/day, about 6.9 mg/kg/day, 7.0 mg/kg/day, about 7.1 mg/kg/day, about 7.2 mg/kg/day, about 7.3 mg/kg/day, about 7.4 mg/kg/day, about 7.5 mg/kg/day, about 7.6 mg/kg/day, about 7.7 mg/kg/day, about 7.8 mg/kg/day, about 7.9 mg/kg/day, 8.0 mg/kg/day, about 8.1 mg/kg/day, about 8.2 mg/kg/day, about 8.3 mg/kg/day, about 8.4 mg/kg/day, about 8.5 mg/kg/day, about 8.6 mg/kg/day, about 8.7 mg/kg/day, about 8.8 mg/kg/day, about 8.9 mg/kg/day, 9.0 mg/kg/day, about 9.1 mg/kg/day, about 9.2 mg/kg/day, about 9.3 mg/kg/day, about 9.4 mg/kg/day, about 9.5 mg/kg/day, about 9.6 mg/kg/day, about 9.7 mg/kg/day, about 9.8 mg/kg/day, about 9.9 mg/kg/day, or about 10.0 mg/kg/day. In some embodiments, the $C_1$-$C_4$ alkyl ester azelate is orally administered at such dosages.

In some aspects, which may be combined with one or more other aspects or embodiments, methods provided herein comprise administering to a subject a pharmaceutical composition comprising DEA at a dosage in a range from about 0.1 mg/kg/day to about 10 mg/kg/day, about 0.2 mg/kg/day to about 9.5 mg/kg/day, about 0.3 mg/kg/day to about 9 mg/kg/day, 0.4 mg/kg/day to about 8.5 mg/kg/day, about 0.5 mg/kg/day to about 8 mg/kg/day, about 0.6 mg/kg/day to about 7.5 mg/kg/day, about 0.7 mg/kg/day to about 7.0 mg/kg/day, about 0.8 mg/kg/day to about 6.5 mg/kg/day, about 0.9 mg/kg/day to about 6.0 mg/kg/day, about 1.0 mg/kg/day to about 5.5 mg/kg/day, about 1.0 mg/kg/day to about 5.0 mg/kg/day, about 0.1 mg/kg/day to about 5.0 mg/kg/day, about 0.25 mg/kg/day to about 5.0 mg/kg/day, about 0.1 mg/kg/day to about 4.0 mg/kg/day, about 0.25 mg/kg/day to about 4.0 mg/kg/day, about 0.5 mg/kg/day to about 4.0 mg/kg/day, about 0.75 to about 4.0 mg/kg/day, or about 0.25 mg/kg/day to about 3.0 mg/kg/day, about 0.25 mg/kg/day to about 2.5 mg/kg/day, about 0.25 mg/kg/day to about 2.0 mg/kg/day, about 0.25 mg/kg/day to about 1.5 mg/kg/day, or about 0.25 mg/kg/day to about 1.5 mg/kg/day. In some embodiments, the pharmaceutical composition comprises orally administered DEA at such dosage ranges.

In some aspects, which may be combined with one or more other aspects or embodiments, methods provided herein comprise administering to a subject a pharmaceutical composition comprising DEA of about 0.1 mg/kg/day, about 0.2 mg/kg/day, about 0.3 mg/kg/day, about 0.4 mg/kg/day, about 0.5 mg/kg/day, about 0.6 mg/kg/day, about 0.7 mg/kg/day, about 0.8 mg/kg/day, about 0.9 mg/kg/day, about 1.0 mg/kg/day, about 1.1 mg/kg/day, about 1.2 mg/kg/day, about 1.3 mg/kg/day, about 1.4 mg/kg/day, about 1.5 mg/kg/day, about 1.6 mg/kg/day, about 1.7 mg/kg/day, about 1.8 mg/kg/day, about 1.9 mg/kg/day, about 2.0 mg/kg/day, about 2.1 mg/kg/day, about 2.2 mg/kg/day, about 2.3 mg/kg/day, about 2.4 mg/kg/day, about 2.5 mg/kg/day, about 2.6 mg/kg/day, about 2.7 mg/kg/day, about 2.8 mg/kg/day, about 2.9 mg/kg/day, about 3.0 mg/kg/day, about 3.1 mg/kg/day, about 3.2 mg/kg/day, about 3.3 mg/kg/day, about 3.4 mg/kg/day, about 3.5 mg/kg/day, about 3.6 mg/kg/day, about 3.7 mg/kg/day, about 3.8 mg/kg/day, about 3.9 mg/kg/day, about 4.0 mg/kg/day, about 4.1 mg/kg/day, about 4.2 mg/kg/day, about 4.3 mg/kg/day, about 4.4 mg/kg/day, about 4.5 mg/kg/day, about 4.6 mg/kg/day, about 4.7 mg/kg/day, about 4.8 mg/kg/day, about 4.9 mg/kg/day, 5.0 mg/kg/day, about 5.1 mg/kg/day, about 5.2 mg/kg/day, about 5.3 mg/kg/day, about 5.4 mg/kg/day, about 5.5 mg/kg/day, about 5.6 mg/kg/day, about 5.7 mg/kg/day, about 5.8 mg/kg/day, about 5.9 mg/kg/day, about 6.0 mg/kg/day, about 6.1 mg/kg/day, about 6.2 mg/kg/day, about 6.3 mg/kg/day, about 6.4 mg/kg/day, about 6.5 mg/kg/day, about 6.6 mg/kg/day, about 6.7 mg/kg/day, about 6.8 mg/kg/day, about 6.9 mg/kg/day, 7.0 mg/kg/day, about 7.1 mg/kg/day, about 7.2 mg/kg/day, about 7.3 mg/kg/day, about 7.4 mg/kg/day, about 7.5 mg/kg/day, about 7.6 mg/kg/day, about 7.7 mg/kg/day, about 7.8 mg/kg/day, about 7.9 mg/kg/day, 8.0 mg/kg/day, about 8.1 mg/kg/day, about 8.2 mg/kg/day, about 8.3 mg/kg/day, about 8.4 mg/kg/day, about 8.5 mg/kg/day, about 8.6 mg/kg/day, about 8.7 mg/kg/day, about 8.8 mg/kg/day, about 8.9 mg/kg/day, 9.0 mg/kg/day, about 9.1 mg/kg/day, about 9.2 mg/kg/day, about 9.3 mg/kg/day, about 9.4 mg/kg/day, about 9.5 mg/kg/day, about 9.6 mg/kg/day, about 9.7 mg/kg/day, about 9.8 mg/kg/day, about 9.9 mg/kg/day, or about 10.0 mg/kg/day. In some embodiments, the pharmaceutical composition comprises orally administered DEA at such dosages.

In some aspects, which may be combined with one or more other aspects or embodiments, methods provided herein comprise administering to a subject a pharmaceutical composition comprising DEA at a dosage of about 0.1 mg/kg/day, about 0.25 mg/kg/day, about 0.5 mg/kg/day, about 1 mg/kg/day, about 2 mg/kg/day, or about 4 mg/kg/day. In some embodiments, the pharmaceutical composition comprises orally administered DEA at such dosages.

In some aspects, which may be combined with one or more other aspects or embodiments, methods provided herein comprise administering to a subject pharmaceutical composition comprising a $C_1$-$C_4$ alkyl ester azelate, wherein the subject has, is suspected of having, or is suspected of having a predisposition to acquiring, at least one of insulin resistance, prediabetes, type II diabetes, overweight, or obesity. In some embodiments, the subject has prediabetes. In some embodiments, the subject has type II diabetes. In some embodiments, the subject has overweight. In some embodiments, the subject has obesity.

In some aspects, which may be combined with one or more other aspects or embodiments, methods provided herein comprise administering to a subject pharmaceutical composition comprising DEA, wherein the subject has, is suspected of having, or is suspected of having a predisposition to acquiring, at least one of insulin resistance, prediabetes, type II diabetes, overweight, or obesity. In some embodiments, the subject has prediabetes. In some embodiments, the subject has type II diabetes. In some embodiments, the subject has overweight. In some embodiments, the subject has obesity.

In some aspects, which may be combined with one or more other aspects or embodiments, methods provided herein comprise administering to a subject pharmaceutical composition comprising a $C_1$-$C_4$ alkyl ester azelate, wherein the subject has a body mass index (BMI) from 25 to less than 30 or has a BMI of 30 or greater.

In some aspects, which may be combined with one or more other aspects or embodiments, methods provided herein comprise administering to a subject pharmaceutical composition comprising DEA, wherein the subject has a BMI from 25 to less than 30 or has a BMI of 30 or greater.

In some aspects, which may be combined with one or more other aspects or embodiments, methods provided herein comprise administering to a subject a pharmaceutical composition comprising a $C_1$-$C_4$ alkyl ester azelate that is formulated for buccal delivery. In some embodiments, the $C_1$-$C_4$ alkyl ester azelate formulated for buccal delivery comprises DEA.

In some aspects, which may be combined with one or more other aspects or embodiments, methods provided herein comprise administering to a subject a pharmaceutical composition comprising a $C_1$-$C_4$ alkyl ester azelate that is formulated for gastric delivery. In some embodiments, the $C_1$-$C_4$ alkyl ester azelate formulated for gastric delivery comprises DEA.

In some aspects, which may be combined with one or more other aspects or embodiments, methods provided herein further comprise administering a second active ingredient in addition to the $C_1$-$C_4$ alkyl ester azelate. In some embodiments, the second active ingredient is administered separately from the pharmaceutical composition comprising the $C_1$-$C_4$ alkyl ester azelate. In some embodiments, the second active ingredient is co-administered with the pharmaceutical composition comprising the $C_1$-$C_4$ alkyl ester azelate. In some embodiments, the second active ingredient comprises one of more of a $C_1$-$C_4$ alkyl ester azelate other than DEA, a biguanide, metformin, buformin, phenformin, a thiazolidinedione, pioglitazone, rosiglitazone, a corticosteroid, prednisone, an insulin, a lipase inhibitor, orlistat, a glucagonlike peptide-1 (GLP-1) agonist, an exendin, exenatide, liraglutide, lixisenatide, albiglutide, dulaglutide, semaglutide, an HMG-CoA reductase inhibitor, a statin, atorvastatin, fluvastatin, lovastatin, pitavastatin, pravastatin, rusovastatin, simvastatin, a fibrate, gemfibrozil, fenofibrate, niacin, a leptin, a leptin agonist, metreleptin, an amylin agonist, pramlintide, and combinations thereof. In some embodiments, the insulin is formulated as a rapid-acting formulation, an intermediate-acting formulation, a long-acting formulation, or combinations thereof.

In some aspects, which may be combined with one or more other aspects or embodiments, methods provided herein comprise administering a pharmaceutical composition consisting essentially of DEA as active ingredient.

In some aspects, which may be combined with one or more other aspects or embodiments, methods provided herein comprise administering a pharmaceutical composition consisting of DEA as active ingredient.

In some aspects, which may be combined with one or more other aspects or embodiments, provided are pharmaceutical compositions comprising a $C_1$-$C_4$ alkyl ester azelate for buccal delivery at a dose in a range from about 0.25 milligram/kilogram (mg/kg) to about 2.0 mg/kg, from about 0.5 to about 2.0 mg/kg, or from about 0.5 to about 1.0 mg/kg. In some embodiments, such $C_1$-$C_4$ alkyl ester azelate is selected from the group consisting of: DEA; DMA; DiPA; DiBuA; and D2PA. In some embodiments, such $C_1$-$C_4$ alkyl ester azelate is DEA.

In some aspects, which may be combined with one or more other aspects or embodiments, provided are pharmaceutical compositions comprising a $C_1$-$C_4$ alkyl ester azelate for buccal delivery at a dose in a range from about 0.25 mg/mg to about 2.0 mg/kg, from about 0.5 to about 2.0 mg/kg, or from about 0.5 to about 1.0 mg/kg wherein the dose is effective at improving one or more abnormal lipid levels when administered to a subject. In some embodiments, such $C_1$-$C_4$ alkyl ester azelate is selected from the group consisting of: DEA; DMA; DiPA; DiBuA; and D2PA. In some embodiments, such $C_1$-$C_4$ alkyl ester azelate is DEA.

In some aspects, which may be combined with one or more other aspects or embodiments, provided are pharmaceutical compositions comprising a $C_1$-$C_4$ alkyl ester azelate for buccal delivery at a dose in a range from about 0.25 mg/mg to about 2.0 mg/kg, from about 0.5 to about 2.0 mg/kg, or from about 0.5 to about 1.0 mg/kg wherein the dose is effective at lowering an elevated LDL level, elevating a diminished HDL level, lowering an elevated triglyceride level, lowering an elevated cholesterol/HDL, lowering an elevated LDL/HDL, lowering an elevated LDL/triglyceride, or lowering an elevated non-cholesterol HDL/HDL when administered to a subject. In some embodiments, such $C_1$-$C_4$ alkyl ester azelate is selected from the group consisting of: DEA; DMA; DiPA; DiBuA; and D2PA. In some embodiments, such $C_1$-$C_4$ alkyl ester azelate is DEA.

In some aspects, which may be combined with one or more other aspects or embodiments, provided are pharmaceutical compositions comprising a $C_1$-$C_4$ alkyl ester azelate for buccal delivery at a dose in a range from about 0.25 mg/mg to about 2.0 mg/kg, from about 0.5 to about 2.0 mg/kg, or from about 0.5 to about 1.0 mg/kg wherein the dose is effective at treating or preventing a dyslipidemia, or a disease or condition associated with a dyslipidemia. In some embodiments, such $C_1$-$C_4$ alkyl ester azelate is selected from the group consisting of: DEA; DMA; DiPA; DiBuA; and D2PA. In some embodiments, such $C_1$-$C_4$ alkyl ester azelate is DEA.

In some aspects, which may be combined with one or more other aspects or embodiments, provided are pharmaceutical compositions comprising a $C_1$-$C_4$ alkyl ester azelate for buccal delivery at a dose in a range from about 0.25 mg/mg to about 2.0 mg/kg, from about 0.5 to about 2.0 mg/kg, or from about 0.5 to about 1.0 mg/kg wherein the dose is effective at treating or preventing a dyslipidemia, or a disease or condition associated with a dyslipidemia, wherein the disease or condition associated with dyslipidemia is selected from the group consisting of hyperlipidemia, hypertriglyceridemia, hypercholesterolemia, mixed hyperlipidemia, familial combined hyperlipidemia, lipodystrophy, cardiovascular disease, hypertension, stroke, atherosclerosis, arteriosclerosis, coronary artery disease, NASH, ASH, fatty liver disease, NAFLD, hepatomegaly, pancreatitis, metabolic syndrome, insulin resistance, prediabetes, type II diabetes, overweight, and obesity. In some embodiments, such $C_1$-$C_4$ alkyl ester azelate is selected from the group consisting of: DEA; DMA; DiPA; DiBuA; and D2PA.

BRIEF DESCRIPTION OF DRAWINGS

FIG. 2A: glucose levels in the subgroup of subjects with ≥100 mg/dL and <100 mg/dL pre-treatment. FIG. 2B: correlation of the change glucose levels observed after treatment with hemoglobin A1c levels and the pre-treatment fasting plasma glucose levels (left and right panels, respectively).

FIG. 3A: Comparison of the DEA effect at 180 min in the high and low A1c subgroups. A horizontal line at 100 mg/dL demarks the boundary between normal and abnormal glucose ranges. FIG. 3B: Depiction of OGTT glucose profiles of the 3 prediabetic subjects depicted in FIG. 1. Day 0 (day before initiation of DEA treatment regimen), dashed lines, Day 21 (last day of DEA treatment regimen), solid lines.

FIG. 4A: fasting insulin in the cohort stratified by A1c levels into the high and low A1c subgroups. The horizontal line at 25 µU/mL demarks the boundary between normal and abnormal insulin ranges. FIG. 4B: insulin profiles in the 3 prediabetic subjects depicted in FIG. 1 over a 180 min time course. Day 0 (day before initiation of DEA treatment regimen), dashed lines, Day 21 (last day of DEA treatment regimen), solid lines.

FIGS. 5A-5E show the effect of DEA treatment on the single lipid markers on subjects described in Example 1. FIG. 5A: total cholesterol. FIG. 5B: LDL cholesterol. FIG. 5C: HDL cholesterol. FIG. 5D: non-cholesterol HDL. FIG. 5E: triglycerides. For all of FIGS. 5A through 5E, the cohort was stratified by A1c levels into the high and low A1c subgroups. Horizontal dashed lines demark boundaries between normal and abnormal ranges for the measured endpoints.

FIG. 6A: total cholesterol/HDL, FIG. 6B: LDL/HDL, FIG. 6C: LDL/triglycerides, FIG. 6D: non-cholesterol HDL/ HDL, FIG. 6E: triglycerides/HDL. In all cases, the cohort was stratified by A1c levels into the high and low A1c subgroups. Horizontal dashed lines demark boundaries between normal and abnormal ranges for the measured endpoints.

FIG. 8 shows the effect of DEA administration via buccal delivery on lipid levels as a function of DEA dose (in mg/kg) as described in Example 2. HDL=high density lipoprotein; Calc LDL=Calculated low-density lipoprotein.

FIG. 15 provides a comparison of the indicated lipid measurement values upon administration of DEA via buccal delivery (upper panel) or gastric delivery (lower panel), as described in Example 2. HDL=high density lipoprotein; Calc LDL=calculated low-density lipoprotein; TC/HDL=total cholesterol/high density lipoprotein ratio.

FIG. 16 provides a comparison of the effect of buccal delivery (upper panel) vs. gastric delivery (lower panel) of the indicated DEA dosages on plasma glucose concentrations measured at the indicated time points after ingestion of a standard glucose dose in an OGTT, as described in Example 2.

FIG. 17 provides a comparison of the effect of the indicated doses of DEA administered via buccal or gastric delivery, as described in Example 2. Upper panel: measured lipid levels (HDL=high density lipoprotein; Calc LDL=calculated low-density lipoprotein; TC/HDL=total cholesterol/high density lipoprotein ratio. Lower panel: plasma glucose concentrations measured at the indicated time points after ingestion of a standard glucose dose in an OGTT.

DETAILED DESCRIPTION

It has now been discovered, inter alia, that administration of $C_1$-$C_4$ alkyl ester azelates, such as DEA, induces beneficial changes ("improvements") in metabolic markers of and risk factors for dyslipidemia, insulin resistance, and diseases or conditions associated with dyslipidemia and/or insulin resistance, such as improvements in plasma lipid levels and glucose levels. These beneficial changes are disclosed herein to correlate, inter alia, with disease or condition severity in subjects with insulin resistance, prediabetes, diabetes, abnormal lipid levels, overweight, and/or obesity.

Without being bound by any theory, these effects are believed to be achieved, at least in part, by modulation of plasma membrane fluidity using membrane-soluble molecules, such as $C_1$-$C_4$ alkyl ester azelates. An increasing body of evidence suggests that even minor changes in membrane structure and composition affect host immune functions, inflammatory signaling and innate immune responses [68-70]. Reports have indicated that the structure of the plasma membrane may be altered in various diseases [71, 72], and that the diet itself can affect plasma membrane structure. It has been proposed that dietary fats and sugars induce alterations in plasma membranes that result in pathological insulin signaling and diminished tissue glucose uptake associated with type II diabetes [73]. Lipophilic molecules such as a $C_1$-$C_4$ alkyl ester azelate, such as DEA, may diffuse into the plasma membrane [74, 75], increase membrane fluidity and trigger metabolic changes that translate into health benefits.

Figure 18:
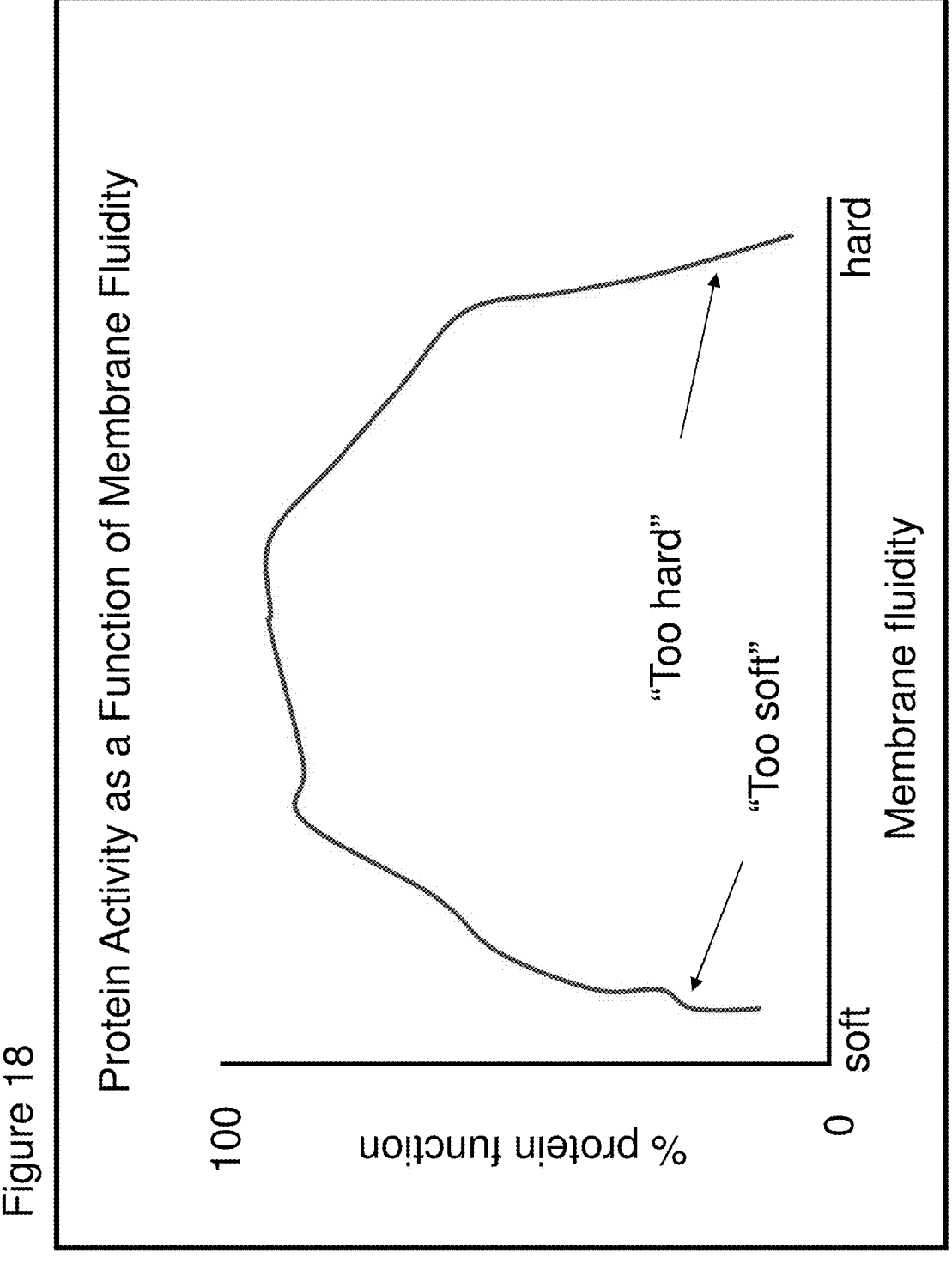
FIG. 18 provides, without wishing to be bound by any theory, a graphic representation of the proposed impact of the degree of membrane fluidity ("soft" to "hard") on percent membrane protein function (100% protein function constituting "maximum" function).

A non-limiting example of such a dynamic is illustrated in FIG. 18, in which percent protein function ("% protein function) as a function of membrane fluidity is graphically illustrated. Molecules that may diffuse into the plasma membrane, such as $C_1$-$C_4$ alkyl ester azelates, such as DEA, may affect (e.g, increase) membrane fluidity and thereby affect (e.g., improve) membrane protein and receptor function in vivo. These effects on membrane fluidity are believed to depend on relative ratios of various lipid species present within the membrane, and it is believed that there exists an optimum fluidity, or range of fluidities, that optimizes/ maximizes membrane protein or membrane receptor function in vivo. It is also believed that an innate feedback-regulated physiological mechanism exists that regulates membrane fluidity via changes in membrane lipids, lipid metabolism, and blood lipid levels, including changes in triglyceride and cholesterol, among others (termed "Adaptive Membrane Fluidity Modulation System ("AMFMS"). Agents that may influence or modulate such lipid levels and/or lipid metabolism may affect AMFMS. Plasma lipid levels, in turn, may therefore serve as biomarkers signifying modulation of AMFMS response and/or identifying agents that are efficacious in modulating AMFMS in such a way that a therapeutic benefit is achieved.

Drugs and therapeutic compounds or molecules that modulate, or are designed to modulate, membrane physicochemical characteristics are therefore believed to serve as viable candidates for the treatment of diverse human diseases, including dyslipidemias, insulin resistance, and diseases or conditions associated therewith, that are caused or exacerbated by abnormal lipid levels and/or abnormal blood glucose levels. Such diseases or conditions include, for example, including hyperlipidemia, hypertriglyceridemia, hypercholesterolemia, combined hyperlipidemia, familial combined hyperlipidemia, lipodystrophy, lipoatrophy, cardiovascular disease, hypertension, stroke, atherosclerosis, arteriosclerosis, coronary artery disease, NASH, ASH, fatty liver disease, NAFLD, hepatomegaly, pancreatitis, prediabetes, type II diabetes, insulin resistance, overweight, and obesity.

In some embodiments, pharmaceutical compositions and methods are provided for improving one more abnormal lipid levels in a subject comprising administering to a subject such pharmaceutical compositions, wherein such pharmaceutical compositions comprise a $C_1$-$C_4$ alkyl ester azelate, such as DEA. In embodiments, there are provided pharmaceutical compositions and methods for lowering an elevated LDL level; elevating a diminished (i.e., "low") HDL level; lowering an elevated triglyceride level; lowering an elevated cholesterol/HDL; lowering an elevated LDL/HDL; lowering an elevated LDL/triglyceride; or lowering elevated non-cholesterol HDL/HDL level; or a combination of the aforementioned in a subject in need thereof. In embodiments, provided are methods of treating or preventing a dyslipidemia, or a disease or condition associated with a dyslipidemia, comprising administering to a subject a pharmaceutical composition comprising a $C_1$-$C_4$ alkyl ester azelate, such as DEA.

The disclosure herein demonstrates, inter alia, diseases or conditions associated with abnormal blood lipid levels and/ or abnormal blood glucose levels, including hyperlipidemia, hypertriglyceridemia, hypercholesterolemia, combined hyperlipidemia, familial combined hyperlipidemia, lipodystrophy, lipoatrophy, cardiovascular disease, hypertension, stroke, atherosclerosis, arteriosclerosis, coronary artery disease, NASH, ASH, fatty liver disease, NAFLD, hepatomegaly, pancreatitis, prediabetes, type II diabetes, insulin resistance, overweight, and obesity.

are amendable to treatment or prevention by administering $C_1$-$C_4$ alkyl ester azelates, such as DEA, to subjects in need of such treatment or prevention.

In some embodiments, there are provided pharmaceutical compositions comprising a $C_1$-$C_4$ alkyl ester azelate, and methods for preventing, ameliorating, or treating a disease or conditions associated with a dyslipidemia or insulin resistance comprising administering to a subject such a $C_1$-$C_4$ alkyl ester azelate. In some embodiments are provided pharmaceutical compositions comprising DEA for preventing, ameliorating, or treating a disease or conditions associated with a dyslipidemia or insulin resistance.

In some embodiments, there are provided methods for preventing, ameliorating, or treating a disease or conditions associated with a dyslipidemia or insulin resistance comprising administering to a subject a $C_1$-$C_4$ alkyl ester azelate. In some embodiments, the $C_1$-$C_4$ alkyl ester azelate comprises DEA.

A "dyslipidemia" or "dyslipidemias", used interchangeably throughout, refers to a group of conditions or disorders characterized by abnormal lipid levels in the blood of a subject.

"Abnormal lipid levels" refers to one or more of the following: elevated LDL level; elevated very low density lipoprotein (VLDL) level; diminished (i.e., "low") HDL level; elevated triglyceride level; elevated cholesterol/HDL; elevated LDL/HDL; elevated LDL/triglyceride; and elevated non-cholesterol HDL/HDL level; relative to normal lipid levels. "Abnormal lipid levels" also refer to blood lipid component concentration levels or blood lipid component concentration ranges.

"Lipid level", "lipid range", "lipid component level", and "lipid component range", or corresponding plural forms, used interchangeably throughout, refers to blood, blood plasma, and/or serum concentrations or concentration ranges of lipid components, which are measured by methods that are routine to one of skill in the art. Such lipid levels, lipid component levels, lipid ranges, and/or lipid component ranges, and the like are measured in, for example, milligrams per deciliter (mg/dL).

"Lipid component" or "lipid components", used interchangeable throughout, refer to, for example, total cholesterol, LDL, HDL, VLDL, triglyceride, and calculated LDL.

"Normal lipid level", "healthy lipid level", "normal lipid range", "healthy lipid range", or corresponding plural forms, used interchangeably throughout, refers to blood and/or serum lipid component concentrations recognized as within healthy limits by a health agency and/or medical community, such as, for example, the United States National Institutes of Health and the World Health Organization.

In embodiments, normal lipid levels are as follows:

|  | Lipid component | Healthy level (milligrams/deciliter ("mg/dL") |
| --- | --- | --- |
| Anyone age 19 or younger | Total cholesterol | Less than 170 mg/dL |
|  | Non-HDL | Less than 120 mg/dL |
|  | LDL | Less than 100 mg/dL |
|  | HDL | More than 45 mg/dL |
| Males age 20 or older | Total cholesterol | 125 to 200 mg/dL |
|  | Non-HDL | Less than 130 mg/dL |
|  | LDL | Less than 100 mg/dL |
|  | HDL | 40 mg/dL or higher |
| Females age 20 or older | Total cholesterol | 125 to 200 mg/dL |
|  | Non-HDL | Less than 130 mg/dL |
|  | LDL | Less than 100 mg/dL |
|  | HDL | 50 mg/dL or higher |

"Abnormal lipid level", "abnormal lipid range", "abnormal lipid levels", or "abnormal lipid ranges", used interchangeably throughout, refers to a measured concentration or concentration range of one or more lipid components that does not correspond to or fall within a normal (healthy) lipid level or normal (healthy) lipid range, respectively.

"Improving", "improves", or "improvement" refers to causing a level of one or more analytes and/or one or more ratios of levels of analytes, such as, for example, glucose, A1c, LDL, VLDL, triglyceride, HDL, calculated cholesterol, cholesterol/HDL ratio, LDL/HDL ratio, LDL/triglyceride ratio or non-cholesterol HDL/HDL ratio to approach a normal level relative to a prior abnormal level. In some embodiments, such "improving" and/or "improvements" are achieved as a result of administration of a pharmaceutical composition comprising a $C_1$-$C_4$ alkyl ester azelate. In some embodiments, such "improving" and/or "improvements" are achieved as a result of administration of a pharmaceutical composition comprising a $C_1$-$C_4$ alkyl ester azelate selected from the group consisting of: DEA; DMA; DiPA; DiBuA; and D2PA. In some embodiments, such "improving" and/or "improvements" are achieved as a result of administration of a pharmaceutical composition comprising DEA.

"Diabetes" refers to a group of metabolic diseases characterized by high blood sugar (glucose) levels which result from defects in insulin secretion or action, or both.

"Type 2 diabetes" or "T2D" refers to one of the two major types of diabetes, wherein the beta cells of the pancreas produce insulin, at least in the early stages of the disease, but the body is unable to use it effectively because the cells of the body are resistant to the action of insulin. In later stages of the disease the beta cells may stop producing insulin. Type 2 diabetes is also known as insulin-resistant diabetes, non-insulin dependent diabetes and adult-onset diabetes.

"Prediabetes" refers to one or more early diabetes-related conditions including impaired glucose utilization, abnormal or impaired fasting glucose levels, impaired glucose tolerance, impaired insulin sensitivity and insulin resistance. In embodiments, "prediabetes" may be defined by a hemoglobin A1c measurement of from about 6.0% or greater.

"Insulin resistant" or "insulin resistance" refers to a condition in which insulin-sensitive cells become resistant to the effects of insulin—a hormone that regulates the uptake of glucose into cells—and/or when the amount of insulin produced is insufficient to maintain a normal glucose level. Cells are diminished in the ability to respond to the action of insulin in promoting the transport of the sugar glucose from blood into muscles and other tissues (i.e., sensitivity to insulin decreases). Eventually, the pancreas produces far more insulin than normal and the cells continue to be resistant. As long as enough insulin is produced to overcome this resistance, blood glucose levels remain normal. Once the pancreas is no longer able to keep up, blood glucose levels to rise, ultimately resulting in diabetes, such as type II diabetes. Insulin resistance ranges from normal (insulin sensitive) to insulin resistant (IR).

"Overweight" refers to a condition defined by an excess amount body fat in a subject. In embodiments, overweight is characterized in a subject by a BMI in a range of 25 to less than 30 and/or a percent body fat generally between about 33% and about 39% for women and generally between about 19% and about 25% for men.

"Obesity" refers to a condition defined by an excess amount body fat in a subject. In embodiments, obesity is characterized in a subject by a BMI equal to or more than 30, and/or a percent body fat generally over about 39% for women and generally over about 25% for men.

The term "disease" as used herein is intended to be generally synonymous, and is used interchangeably with, the terms "disorder" and "condition" (as in medical condition), in that all reflect an abnormal condition of the human or animal body or of one of its parts that impairs normal functioning, is typically manifested by distinguishing signs and symptoms, and causes the human or animal to have a reduced duration or quality of life.

The term "about," as used herein, is intended to qualify the numerical values which it modifies, denoting such a value as variable within a margin of error. When no particular margin of error, such as a standard deviation to a mean value given in a chart or table of data, is recited, the term "about" should be understood to mean that range which would encompass the recited value and the range which would be included by rounding up or down to that figure as well, taking into account significant figures.

When numerical ranges of values are disclosed, such ranges are intended to include the numbers themselves and any sub-range between them. This range may be integral or continuous between and including the end values.

The term "combination therapy" means the administration of two or more therapeutic agents to treat a therapeutic condition or disorder described in the present disclosure. Such administration may encompass co-administration of these therapeutic agents in a substantially simultaneous manner, such as in a single dosage form having a fixed ratio of active ingredients or in multiple, separate dosage forms for each active ingredient. In addition, such administration also encompasses use of each type of therapeutic agent in a sequential manner. In either case, the treatment regimen will provide beneficial effects of the drug combination in treating the conditions or disorders described herein.

The phrase "therapeutically effective amount" or "effective amount" is intended to qualify the amount of active ingredients used to achieve a clinical or therapeutic outcome, improvement, or benefit in a subject. A "therapeutically effective amount or "effective amount" is an amount that will provide some improvement, alleviation, mitigation, decrease, or stabilization in at least one clinical symptom in the subject. Those skilled in the art will appreciate that the therapeutic effects need not be complete or curative, as long as some benefit is provided to the subject.

In some embodiments, a "therapeutically effective amount" or "effective amount" is an amount effective in improving one or more abnormal lipid level in a subject when administered to the subject.

In some embodiments, a "therapeutically effective amount" or "effective amount" is an amount effective in lowering an elevated LDL level, elevating a diminished HDL level, lowering an elevated triglyceride level, lowering an elevated cholesterol/HDL, lowering an elevated LDL/ HDL, lowering an elevated LDL/triglyceride, or lowering an elevated non-cholesterol HDL/HDL in a subject when administered to the subject.

In some embodiments, a "therapeutically effective amount" or "effective amount" is an amount effective in treating or preventing a dyslipidemia or a disease or condition associated with a dyslipidemia.

In some embodiments, a "therapeutically effective amount" or "effective amount" is an amount effective in treating or preventing a one or more diseases or conditions associated with a dyslipidemia selected from the group consisting of hyperlipidemia, hypertriglyceridemia, hypercholesterolemia, mixed hyperlipidemia, familial combined hyperlipidemia, lipodystrophy, cardiovascular disease, hypertension, stroke, atherosclerosis, arteriosclerosis, coronary artery disease, NASH, ASH, fatty liver disease, NAFLD, hepatomegaly, pancreatitis, metabolic syndrome, insulin resistance, prediabetes, type II diabetes, overweight, and obesity, in a subject when administered to the subject. therein the treatment of a disease, condition, or disorder. This amount will achieve the goal of reducing the impact of, or eliminating the disease, condition, or disorder.

Reference to "treatment" of a subject includes prophylaxis, or prevention. The term "subject" means all mammals including humans. Examples of patients include humans, cows, dogs, cats, goats, sheep, pigs, and rabbits. In some embodiments, the subject is a human.

"Associated with" refers to a disease, condition, or clinical finding or result that: is coincident with; causative for; a co-morbidity of; a risk factor for; a biomarker for; and/or is indicative of a predisposition for acquiring; another disease, condition, or clinical finding or result.

The term "comprising" is intended to mean that the compositions and methods include the recited elements, but not excluding others. The term "consisting essentially of," as applied to the compositions of the present embodiments, means the composition can contain additional elements as long as the additional elements do not materially alter the composition. The term "materially altered," as applied to a composition, refers to an increase or decrease in the therapeutic effectiveness of the composition as compared to the effectiveness of a composition consisting of the recited elements. In other words, "consisting essentially of" when used to define compositions, shall mean excluding other components of any essential significance to the composition. Thus, a composition consisting essentially of the components as defined herein would not exclude trace contaminants from the isolation and purification method and pharmaceutically acceptable carriers. "Consisting of" shall mean excluding more than trace elements of other ingredients and substantial method steps for administering the compositions of this invention. Embodiments defined by each of these transition terms are within the scope of this invention.
Pharmaceutical Compositions and Treatments Provided herein are pharmaceutical compositions which include one or more of certain compounds disclosed herein, such as $C_1$-$C_4$ alkyl ester azelates, which may optionally be formulated or otherwise combined with one or more pharmaceutically acceptable carriers thereof, and also optionally may include one or more other therapeutic ingredients. In some embodiments, the pharmaceutical composition comprises a $C_1$-$C_4$ alkyl ester azelate selected from the group consisting of DEA, DMA, DiPA, DiBuA, and D2PA, each of which can be prepared from azelaic acid and the respective alcohols (e.g., methyl, ethyl, propyl, isobutyl, 1-, 2, and 3-pentyl, and cyclohexyl) using the standard acid-catalyzed esterification. An aliphatic acid contains an alkyl group bound to the carboxyl group.

In embodiments, the pharmaceutical composition comprises DEA. Diethyl azelate may be found in some common foods (Yu 2001; Plough, Zhangxia et al. 2002; Kim and Chung 2008; Fan, Fan et al. 2015) and is an approved flavoring additive at gram quantities, in the EU (AFC 2005).

In embodiments, the pharmaceutical composition comprises a second active ingredient, which may comprise one or more of a $C_1$-$C_4$ alkyl ester azelate (different from DEA, if DEA is already included in the pharmaceutical composition), a biguanide, metformin, buformin, phenformin, a thiazolidinedione, pioglitazone, rosiglitazone, a corticosteroid, prednisone, an insulin, a lipase inhibitor, orlistat, a glucagonlike peptide-1 (GLP-1) agonist, an exendin, exenatide, liraglutide, lixisenatide, albiglutide, dulaglutide, semaglutide, an HMG-COA reductase inhibitor, a statin, atorvastatin, fluvastatin, lovastatin, pitavastatin, pravastatin, rusovastatin, simvastatin, a fibrate, gemfibrozil, fenofibrate, niacin, a leptin, a leptin agonist, metreleptin, an amylin agonist, pramlintide, and combinations thereof.

Other second active ingredients include, without limitation, alpha glucosidase inhibitors, dipeptidyl peptidase-4 (DPP-4) inhibitors, AKA incretin enhancers (including alogliptin, linagliptin, saxagliptin, sitagliptin, vildagliptin), sulfonylureas and related agents (including glibenclamide, gliclazide, glimepride, glipizide, tolbutamide and nateglinide, repaglinide), acarbose, sodium-glucose co-transporter 2 (SGLT2) inhibitors (e.g., canagliflozin, dapagliflozin, empagliflozin) and natural products such as nopal (prickly pear cactus), fenugreek, karela (bitter melon), gymnema, ginseng, tronadora, chromium, and alpha-lipoic acid, and hydroxycitric acid.

Where compounds have been in disuse due to toxicity or other detrimental side effect, dosages may be substantially reduced compared to those that were originally approved.

In some embodiments, the thiazolidinedione includes pioglitazone, rosiglitazone, or combinations thereof.

In some embodiments, the corticosteroid comprises prednisone.

In some embodiments, the insulin is formulated as a rapid-acting formulation, an intermediate-acting formulation, a long-acting formulation, or combinations thereof.

In some embodiments, the lipase inhibitor comprises orlistat.

In some embodiments, the GLP-1 agonist includes exendin, exenatide, liraglutide, lixisenatide, albiglutide, dulaglutide, semaglutide, semaglutide formulated for oral administration (e.g., RYBELSUS® semaglutide tablets) and combinations thereof.

In some embodiments, the HMG-COA reductase inhibitor comprises a statin, atorvastatin, fluvastatin, lovastatin, pitavastatin, pravastatin, rusovastatin, simvastatin In some embodiments, the pharmaceutical composition consists essentially of DEA as active ingredient. In some embodiments, the pharmaceutical composition consists of DEA as active ingredient.

In some embodiments, the pharmaceutical composition is enterically coated. The pharmaceutical composition of the present embodiments can be configured for immediate release, extended release, sustained release, and controlled release of, a $C_1$-$C_4$ alkyl ester azelate, such as DEA. In some embodiments, the pharmaceutical composition is configured for extended release of a $C_1$-$C_4$ alkyl ester azelate, such as DEA. In some embodiments, the pharmaceutical composition is configured for any combination of immediate release, extended release, sustained release, and controlled release of a $C_1$-$C_4$ alkyl ester azelate, such as DEA. The various release profiles of the foregoing embodiments may be achieved via any conventional method known in the art. In some embodiments, the pharmaceutical composition is administered once daily. In some embodiments, the pharmaceutical composition is administered twice or thrice daily.

The carrier(s) are "acceptable" in the sense of being compatible with the other ingredients of the formulation and not deleterious to the subject. Proper formulation is dependent upon the route of administration chosen. Any of the well-known techniques, carriers, and excipients as understood in the art may be used e.g., those disclosed in Remington's Pharmaceutical Sciences. The pharmaceutical compositions disclosed herein may be manufactured in any manner known in the art, such as by means of conventional mixing, dissolving, granulating, dragee-making, levigating, emulsifying, encapsulating, entrapping or compression processes.

The pharmaceutical compositions include those suitable for enteral (including oral, buccal, gastric, and rectal), parenteral (including subcutaneous, intradermal, intramuscular, intravenous, intraarticular, and intramedullary), intraperitoneal, transmucosal, transdermal, and topical (including dermal, buccal, sublingual, ocular, intranasal, and intraocular) administration or delivery, although the most suitable route of administration or delivery may depend upon for example the condition and disorder of the recipient.

In embodiments, the pharmaceutical composition is formulated for oral administration or delivery.

In embodiments, the pharmaceutical composition is formulated for buccal administration or delivery.

In embodiments the pharmaceutical composition is formulated for gastric administration or delivery.

The pharmaceutical compositions may conveniently be presented in unit dosage forms and may be prepared by any of the methods well known in the art of pharmacy. Typically, these methods include the step of mixing a $C_1$-$C_4$ alkyl ester azelate, such as DEA, and optionally any co-administered active ingredient disclosed herein, with the carrier which constitutes one or more accessory ingredients. In general, the pharmaceutical compositions are prepared by uniformly and intimately mixing the active ingredients with liquid carriers or finely divided solid carriers or both and then, as necessary, shaping the product into the desired composition.

Pharmaceutical compositions of a $C_1$-$C_4$ alkyl ester azelate, such as DEA, and any optional secondary active ingredient, suitable for, for example, oral, buccal, or gastric administration or delivery may be presented as discrete units such as capsules, cachets or tablets each containing a predetermined amount of the active ingredient(s); as a powder or granules; as a solution or a suspension in an aqueous liquid or a non-aqueous liquid; or as an oil-in-water liquid emulsion or a water-in-oil liquid emulsion. The active ingredient(s) may also be presented as a bolus, electuary or paste. For buccal or sublingual administration or delivery, the compositions may take the form of tablets, lozenges, pastilles, or gels formulated in conventional manner. Such compositions may comprise the active ingredient in a flavored basis such as sucrose and acacia or tragacanth. For gastric administration or delivery, the compositions may take the form of gelatin capsules, such as hard gelatin capsules. An example of a gelatin capsule for, for example, gastric administration or delivery of a $C_1$-$C_4$ alkyl ester azelate, such as DEA, is a gelatin capsule size 00 (PureCaps USA, Philmont, NY).

Pharmaceutical preparations which can be used, for example, for oral, buccal, or gastric administration or delivery include tablets, capsules made of gelatin, which may be hard gelatin capsules, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. The tablets may optionally be coated or scored and may be formulated so as to provide slow or controlled release of the active ingredient therein.

All pharmaceutical compositions for, for example, oral, buccal, or gastric administration or delivery may be in dosages suitable for such administration or delivery. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Examples of fillers or diluents for use in oral pharmaceutical formulations such as capsules and tablets include, without limitation, lactose, mannitol, xylitol, dextrose, sucrose, sorbitol, compressible sugar, microcrystalline cellulose (MCC), powdered cellulose, cornstarch, pregelatinized starch, dextrates, dextran, dextrin, dextrose, maltodextrin, calcium carbonate, dibasic calcium phosphate, tribasic calcium phosphate, calcium sulfate, magnesium carbonate, magnesium oxide, poloxamers such as polyethylene oxide, and hydroxypropyl methyl cellulose. Fillers may have complexed solvent molecules, such as in the case where the lactose used is lactose monohydrate. Fillers may also be proprietary, such in the case of the filler PROSOLV® (available from JRS Pharma). PROSOLV® is a proprietary, optionally high-density, silicified microcrystalline cellulose composed of 98% microcrystalline cellulose and 2% colloidal silicon dioxide. Silicification of the microcrystalline cellulose is achieved by a patented process, resulting in an intimate association between the colloidal silicon dioxide and microcrystalline cellulose. PROSOLV® comes in different grades based on particle size, and is a white or almost white, fine or granular powder, practically insoluble in water, acetone, ethanol, toluene and dilute acids and in a 50 g/L solution of sodium hydroxide.

Examples of disintegrants for use in pharmaceutical compositions such as capsules and tablets include, without limitation, sodium starch glycolate, sodium carboxymethyl cellulose, calcium carboxymethyl cellulose, croscarmellose sodium, povidone, crospovidone (polyvinylpolypyrrolidone), methyl cellulose, microcrystalline cellulose, powdered cellulose, low-substituted hydroxypropyl cellulose, starch, pregelatinized starch, and sodium alginate.

Additionally, glidants and lubricants may be used in oral pharmaceutical compositions to ensure an even blend of excipients upon mixing. Examples of lubricants include, without limitation, calcium stearate, glyceryl monostearate, glyceryl palmitostearate, hydrogenated vegetable oil, light mineral oil, magnesium stearate, mineral oil, polyethylene glycol, sodium benzoate, sodium lauryl sulfate, sodium stearyl fumarate, stearic acid, talc, and zinc stearate. Examples of glidants include, without limitation, silicon dioxide ($SiO_2$), talc cornstarch, and poloxamers. Poloxamers (or LUTROL®, available from the BASF Corporation) are A-B-A block copolymers in which the A segment is a hydrophilic polyethylene glycol homopolymer and the B segment is hydrophobic polypropylene glycol homopolymer.

Examples of tablet binders include, without limitation, acacia, alginic acid, carbomer, carboxymethyl cellulose sodium, dextrin, ethylcellulose, gelatin, guar gum, hydrogenated vegetable oil, hydroxyethyl cellulose, hydroxypropyl cellulose, hydroxypropylmethyl cellulose, copolyvidone, methyl cellulose, liquid glucose, maltodextrin, polymethacrylates, povidone, pregelatinized starch, sodium alginate, starch, sucrose, tragacanth, and zein.

Methods of Treatment

It has been discovered, inter alia, that $C_1$-$C_4$ alkyl ester azelates, such as DEA have beneficial effect on, inter alia, improving blood lipid levels, blood glucose levels, blood insulin levels, and blood A1c levels when administered to subjects. Such benefits were observed, for example, in subjects with one or more diseases of conditions associated with certain metabolic derangements, such as overweight, obesity, insulin-resistance, prediabetes, and/or type II diabetes, and other sequelae associated with metabolic syndrome and lipid imbalance. This is significant, at least because it has been reported that abnormal lipids and lipid levels, while important for maintaining metabolic homeostasis and adapting to stresses imposed by nutrient fluctuations during feeding and fasting cycles, can also contribute to—or serve as risk factors—for certain diseases or conditions such as cardiovascular disease, hypertension, stroke, atherosclerosis, arteriosclerosis, coronary artery disease, NASH, ASH, fatty liver disease, NAFLD, hepatomegaly, pancreatitis, and the like. Furthermore, as lipid metabolism and immune responses are highly integrated, accumulation of harmful lipids or generation of lipid signaling intermediates can interfere with immune regulation in multiple tissues, causing a vicious cycle of immune-metabolic dysregulation, and the development of a large array of conditions and disorders associated with dyslipidemias and metabolic syndrome. Without wishing to be bound by any theory, it is believed that $C_1$-$C_4$ alkyl ester azelates, such as DEA, exert the beneficial effects disclosed herein by modulating membrane fluidity and/or modulating immune modulatory signaling intermediates and mechanisms in a manner that promotes and/or normalizes metabolic and immune homeostasis, thereby preventing, ameliorating, or treating diseases or conditions influenced by metabolic and inflammatory derangements.

Conditions and disorders associated with dyslipidemias and metabolic syndrome include, for example: hyperlipidemia, hypertriglyceridemia, hypercholesterolemia, mixed hyperlipidemia, familial combined hyperlipidemia, lipodystrophy, cardiovascular disease, hypertension, stroke, atherosclerosis, arteriosclerosis, coronary artery disease, NASH, ASH, fatty liver disease, NAFLD, hepatomegaly, pancreatitis, metabolic syndrome, insulin resistance, prediabetes, type II diabetes, overweight, and obesity. Accordingly, to subjects who have, are suspected of having, or have a predisposition for acquiring a dyslipidemia, metabolic syndrome, or one or more of conditions or diseases associate with a dyslipidemia or metabolic syndrome area amenable to treatment using the methods provided herein and throughout.

In some embodiments, methods are provided for improving one or more abnormal lipid levels in a subject, comprising administering to the subject a pharmaceutical composition comprising an effective amount of a $C_1$-$C_4$ alkyl ester azelate to improve the one or more abnormal lipid levels. In some embodiments, the $C_1$-$C_4$ alkyl ester azelate is selected from the group consisting of: DEA; DMA; DiPA; DiBuA; and D2PA. In some embodiments the $C_1$-$C_4$ alkyl ester azelate is DEA.

In some embodiments, methods are provided for lowering an elevated LDL level, elevating a diminished HDL level, lowering an elevated triglyceride level, lowering an elevated cholesterol/HDL, lowering an elevated LDL/HDL, lowering an elevated LDL/triglyceride, or lowering an elevated noncholesterol HDL/HDL in a subject, the method comprising administering to the subject an effective amount of a pharmaceutical composition comprising a $C_1$-$C_4$ alkyl ester azelate. In some embodiments the $C_1$-$C_4$ alkyl ester azelate is selected from the group consisting of: DEA; DMA; DiPA; DiBuA; and D2PA. In some embodiments the $C_1$-$C_4$ alkyl ester azelate is DEA.

In some embodiments, methods are provided for treating or preventing a dyslipidemia or a disease or condition associated with a dyslipidemia, in a subject comprising administering to the subject a pharmaceutical composition comprising a $C_1$-$C_4$ alkyl ester azelate in an amount effective to treat or prevent the dyslipidemia, or a disease or condition associated with a dyslipidemia, in the subject. In some embodiments, the $C_1$-$C_4$ alkyl ester azelate is selected from the group consisting of: DEA; DMA; DiPA; DiBuA; and D2PA. In some embodiments the $C_1$-$C_4$ alkyl ester azelate is DEA.

In some embodiments, the methods comprise oral administration of a $C_1$-$C_4$ alkyl ester azelate, such as DEA. In some embodiments, oral administration provides for buccal delivery or gastric delivery of a $C_1$-$C_4$ alkyl ester azelate, such as DEA. Such oral administration may be accomplished, for example, via tablet, capsule elixir, or the like, as described herein and throughout. In some embodiments, the administering step is performed parenterally. In some embodiments, the parenteral administration is performed intramuscularly or subcutaneously. In some embodiments, combinations of enteric and parenteral administration may be employed.

A suitable or effective single dose size is a dose that is capable of causing a measurable improvement in one or more lipid levels and/or in insulin resistance, blood glucose levels, of blood A1c percentage, of a subject when administered one or more times over a suitable time period. A suitable or effective single dose size can also be a dose that is capable of causing a measurable change in insulin resistance in a subject as compared to the measure of insulin resistance established prior to initiation of the treatment, when administered one or more times over a suitable time period. Doses can vary depending upon the condition of the subject being treated, including the severity of the dyslipidemia, conditions or disease associated with the dyslipidemia, whether the subject suffers from overt diabetes or not, and/or any other related or non-related health factors experienced by a particular patient.

In some embodiments, the methods provided herein comprise administering a pharmaceutical composition including a $C_1$-$C_4$ alkyl ester azelate in a dosage of about 0.1 mg/kg/day, about 0.2 mg/kg/day, about 0.3 mg/kg/day, about 0.4 mg/kg/day, about 0.5 mg/kg/day, about 0.6 mg/kg/day, about 0.7 mg/kg/day, about 0.8 mg/kg/day, about 0.9 mg/kg/day, about 1.0 mg/kg/day, about 1.1 mg/kg/day, about 1.2 mg/kg/day, about 1.3 mg/kg/day, about 1.4 mg/kg/day, about 1.5 mg/kg/day, about 1.6 mg/kg/day, about 1.7 mg/kg/day, about 1.8 mg/kg/day, about 1.9 mg/kg/day, about 2.0 mg/kg/day, about 2.1 mg/kg/day, about 2.2 mg/kg/day, about 2.3 mg/kg/day, about 2.4 mg/kg/day, about 2.5 mg/kg/day, about 2.6 mg/kg/day, about 2.7 mg/kg/day, about 2.8 mg/kg/day, about 2.9 mg/kg/day, about 3.0 mg/kg/day, about 3.1 mg/kg/day, about 3.2 mg/kg/day, about 3.3 mg/kg/day, about 3.4 mg/kg/day, about 3.5 mg/kg/day, about 3.6 mg/kg/day, about 3.7 mg/kg/day, about 3.8 mg/kg/day, about 3.9 mg/kg/day, about 4.0 mg/kg/day, about 4.1 mg/kg/day, about 4.2 mg/kg/day, about 4.3 mg/kg/day, about 4.4 mg/kg/day, about 4.5 mg/kg/day, about 4.6 mg/kg/day, about 4.7 mg/kg/day, about 4.8 mg/kg/day, about 4.9 mg/kg/day, 5.0 mg/kg/day, about 5.1 mg/kg/day, about 5.2 mg/kg/day, about 5.3 mg/kg/day, about 5.4 mg/kg/day, about 5.5 mg/kg/day, about 5.6 mg/kg/day, about 5.7 mg/kg/day, about 5.8 mg/kg/day, about 5.9 mg/kg/day, about 6.0 mg/kg/day, about 6.1 mg/kg/day, about 6.2 mg/kg/day, about 6.3 mg/kg/day, about 6.4 mg/kg/day, about 6.5 mg/kg/day, about 6.6 mg/kg/day, about 6.7 mg/kg/day, about 6.8 mg/kg/day, about 6.9 mg/kg/day, 7.0 mg/kg/day, about 7.1 mg/kg/day, about 7.2 mg/kg/day, about 7.3 mg/kg/day, about 7.4 mg/kg/day, about 7.5 mg/kg/day, about 7.6 mg/kg/day, about 7.7 mg/kg/day, about 7.8 mg/kg/day, about 7.9 mg/kg/day, 8.0 mg/kg/day, about 8.1 mg/kg/day, about 8.2 mg/kg/day, about 8.3 mg/kg/day, about 8.4 mg/kg/day, about 8.5 mg/kg/day, about 8.6 mg/kg/day, about 8.7 mg/kg/day, about 8.8 mg/kg/day, about 8.9 mg/kg/day, 9.0 mg/kg/day, about 9.1 mg/kg/day, about 9.2 mg/kg/day, about 9.3 mg/kg/day, about 9.4 mg/kg/day, about 9.5 mg/kg/day, about 9.6 mg/kg/day, about 9.7 mg/kg/day, about 9.8 mg/kg/day, about 9.9 mg/kg/day, or about 10.0 mg/kg/day. In some embodiments, the $C_1$-$C_4$ alkyl ester azelate that is administered at such dosage ranges is selected from the group consisting of: DEA; DMA; DiPA; DiBuA; and D2PA. In some embodiments, the $C_1$-$C_4$ alkyl ester azelate that is administered at such dosage ranges is DEA.

In some embodiments, the $C_1$-$C_4$ alkyl ester azelate, such as DEA, in the pharmaceutical composition is about 1 mg/kg/day. The dose range for an adult human is generally from 3 mg to 2 g per day. The dosage may be calculated based on the body mass of the subject. For example, based on an average body mass of from about 120 to about 180 kg, the dose range for an adult human may be from 50 mg to 0.5 g per day; based on an average body mass of from about 80 to about 120 kg, the dose range for an adult human may be from 10 mg to 1 g per day, or from 5 mg to 0.15 g per day; based on an average body mass of from about 60 to about 80 kg, the dose range for an adult human may be from 25 mg to 0.3 g per day. The pharmaceutical compositions may contain, for example, from about 0.1% to about 99% by weight, of DEA, depending on the method of administration. Where the pharmaceutical compositions comprise dosage units, each unit may contain, for example, from about 10 to 2000 mg, or from about 10 to 1000 mg of the active ingredient, more typically from 5 mg to 150 mg, in single or divided doses. Those skilled in the art may recognize the flexibility in dosing based on individual patient needs and dosages may be outside these ranges based on responses observed in tests such as the glucose tolerance test, and through assessment of baseline lipid levels (e.g., lipid levels measured prior to commencement of treatment). Thus, these ranges should be understood to be merely exemplary. In some embodiments, a dosage is selected based on diagnostic screens as part of an ongoing treatment regimen, thus allowing for adjustment of the dosage as needed for each individual subject.

The methods may further include administering a second active ingredient. In some embodiments, administering the second active ingredient is separate from administering the pharmaceutical composition including the $C_1$-$C_4$ alkyl ester azelate, such as DEA. In some embodiments, the second active ingredient is co-administered with the pharmaceutical composition including the $C_1$-$C_4$ alkyl ester azelate, such as DEA. In some embodiments, the second active ingredient is present in the pharmaceutical composition including the $C_1$-$C_4$ alkyl ester azelate, such as DEA. Such a second active ingredient may be selected from: a $C_1$-$C_4$ alkyl ester azelate other than DEA, a biguanide, metformin, buformin, phenformin, a thiazolidinedione, pioglitazone, rosiglitazone, a corticosteroid, prednisone, an insulin, a lipase inhibitor, orlistat, a glucagonlike peptide-1 (GLP-1) agonist, an exendin, exenatide, liraglutide, lixisenatide, albiglutide, dulaglutide, semaglutide, an HMG-COA reductase inhibitor, a statin, atorvastatin, fluvastatin, lovastatin, pitavastatin, pravastatin, rusovastatin, simvastatin, a fibrate, gemfibrozil, fenofibrate, niacin, a leptin, a leptin agonist, metreleptin, an amylin agonist, pramlintide, and combinations thereof.

The following Examples are submitted to illustrate embodiments of the present disclosure. These Examples are intended to be illustrative only and are not intended to limit the scope of the present disclosure. Also, parts and percentages are by weight unless otherwise indicated. As used herein, "room temperature" refers to a temperature of from about 20° C. to about 25° C.

EXAMPLES

Example 1

Described in this example is an evaluation of the effects of alkyl azelates, such as DEA, on certain markers of insulin resistance and dyslipidemia, including blood plasma glucose, insulin levels and/or lipid levels [30], when orally administered to overweight or obese adult male volunteers. The cohort spanned from normal to prediabetic subjects based on the levels of the blood marker glycated hemoglobin A1c (A1c) which is considered a longer-term gauge of blood glucose control [31]. The American Diabetes Association defines prediabetes as an A1c of 5.7%-6.4%, but also states that patients with an A1c just below the 5.7% threshold are at risk of developing diabetes [32]. The results of the study demonstrate that, alkyl azelates, such as DEA, can significantly improve lipid levels, and thus dyslipidemia or a disease or conditions associated with a dyslipidemia, such as in a setting of insulin resistance.

Abbreviations

A1c=hemoglobin A1c
AFLD=alcoholic fatty liver disease
BMI=body mass index
CHL=cholesterol
DEA=diethyl azelate
GC-MS=gas chromatography-mass spectrometry
HDL=high density lipoprotein
LDL=low density lipoprotein NAFLD=non-alcoholic fatty liver disease
NASH=non-alcoholic steatohepatitis
ncHDL=non-cholesterol high density lipoprotein
OGTT=fasting oral glucose tolerance test
T2D=type 2 diabetes
TRG=triglycerides

Materials and Methods

Diethyl azelate was synthesized from azelaic acid and ethyl alcohol sing the standard acid-catalyzed esterification followed by fractional distillation to produce DEA to 99% purity as determined by chromatography-mass spectrometry (GC-MS).

Other azelaic acid esters are synthesized from azelaic acid and respective alcohols (e.g., methyl, propyl, isobutyl, 1-, 2—, and 3-pentyl) using the standard acid-catalyzed esterification followed by fractional distillation to produce DMA, DiPA, DiBuA, di-(1-pentyl) azelate (DIPA), (D2PA), or di-(3-pentyl) azelate (D3PA).

The human studies were performed with the approval of the Institutional Review Board at IntegReview (Austin, TX, USA). Written consent was obtained from study subjects following the informed consent protocol EP20160001. The Board was constituted and operated in accordance with the ethical rules of the Helsinki Declaration and requirements as described in the US Code of Federal Regulations 21 CFR Part 56.

Seventeen subjects were recruited by sampling a large population at risk for T2D (according to convenience sample; a statistical method of drawing representative data [33]) to measure the changes in glucose, lipid and insulin measurements after an OGTT after the subjects had been treated for 21 days.

The subjects were overweight to obese males with body mass indices (BMIs) ranging from 27.2 to 43.6 kg/m$^2$, glycated hemoglobin A1c (HbA1c) of 5.0-6.2% and insulin levels of 8.8-52 μU/mL. The study was conducted by Clinical Trials of Texas, Inc. in San Antonio, TX. The cohort represented a population at risk for the development of T2D.

The study was restricted to male participants to control for the variability of insulin sensitivity associated with the menstrual cycle [34]. The subjects received 21 daily oral doses ("q1d") of 1 mg/kg DEA. An OGTT, in which 75 grams of glucose in a total volume of 300 mL was administered orally to subjects, was performed on Day 0 and again on Day 21 and glucose measurements performed at −30, −5 and 0 min, insulin measurements at −30 and 0 min, and both glucose measurements and insulin measurements at 30, 60, 90, 120 and 180 minutes, where "0 min" is the time at which the glucose solution was administered. The 180-minute time point was selected to gain an early insight into the possible signal of drug action [35]. Blood lipid levels (triglycerides, cholesterol, HDL, non-cholesterol HDL and LDL) were measured before the onset of treatment on Day 0 and again on Day 21. The error of the assays was <5% [36].

The results of the various marker measurements at Day 0 and Day 21 were compared using both the paired Students T-test and the Wilcoxon signed rank test. The results of both calculations are provided; the p-value from the paired Student T-test first, followed by the p-value from the Wilcoxon signed rank test. Generalized Estimating Equations and bootstrapping were used to verify the results generated with other methods. Fasting glucose was calculated as the average of the −30, −5, and 0-minute measurements and fasting insulin was calculated as the average of the −30- and 0-minute measurements. Spearman's correlation coefficient was calculated for the relationship between A1c and pre-treatment fasting plasma glucose versus post-treatment fasting plasma glucose. Area under the curve (AUC) was calculated over the 180-minute time span of the OGTT. All analyses were performed using the open language engine R 3.4.4. Statistical significance was at the $\alpha$=0.05 level.

Results

Daily oral DEA was well tolerated by all study subjects; only one subject experienced transient mild diarrhea in the first week of treatment. No other adverse effects were reported. Specific effects of DEA on examined endpoints are summarized in Table 1 and presented in detail below.

TABLE 1

| Variables (geometric mean and 95% confidence limits) determined during a 21-day's study of diethylazelate in overweight male subjects | | | | | |
|---|---|---|---|---|---|
| | All (n = 17) | | Low A1c (n = 8) | | High A1c (n = 9) |
| Variable | D0 | D21 | D0 | D21 | D0 |
| Fasting plasma glucose (mg/dL) | 101.662 | 99.732 | 97.731 | 99.138 | 105.156 |
| | (90.113, 113.211) | (92.462, 107.002) | (86.515, 108.947) | (92.916, 105.359) | (93.863, 116.448) |
| Glucose 180 min (mg/dL) | 100.315 | 91.579 | 90.569 | 87.588 | 108.978 |
| | (66.998, 133.631) | (62.923, 120.236) | (72.025, 109.113) | (72.575, 102.6) | (67.269, 150.687) |
| AUC Glucose | 25826 | 25356 | 24153 | 24756 | 27313 |
| | (20758, 30894) | (20152, 30559) | (21644, 26663) | (23040, 26471) | (20944, 33682) |
| Fasting insulin (μU/mL) | 26.082 | 25.894 | 21.212 | 22.512 | 30.411 |
| | (10.065, 42.1) | (3.064, 48.724) | (12.172, 30.253) | (10.835, 34.19) | (10.492, 50.331) |
| AUC insulin | 24963 | 26834 | 22609 | 27785 | 27055 |
| | (15288, 34637) | (14646, 39021) | (14285, 30932) | (14299, 41271) | (16280, 37830) |
| Cholesterol, total (mg/dL) | 150.118 | 148.882 | 129.5 | 125.5 | 168.444 |
| | (104.379, 195.856) | (101.074, 196.69) | (86.608, 172.392) | (72.38, 178.62) | (126.358, 210.531) |
| LDL cholesterol (mg/dL) | 93.765 | 89.765 | 81.125 | 74.375 | 105 |
| | (61.047, 126.482) | (57.062, 122.467) | (54.698, 107.552) | (45.045, 103.705) | (69.957, 140.043) |
| HDL cholesterol (mg/dL) | 32.765 | 34.412 | 27 | 26.75 | 37.889 |
| | (22.273, 43.256) | (22.653, 46.17) | (16.033, 37.967) | (13.858, 39.642) | (30.67, 45.108) |
| Non-cholesterol HDL (mg/dL) | 117.412 | 114.471 | 102.5 | 98.75 | 130.667 |
| | (80.052, 154.772) | (76.013, 152.929) | (67.958, 137.042) | (55.996, 141.504) | (94.232, 167.102) |
| Triglycerides (mg/dL) | 118.588 | 124 | 106.875 | 122.625 | 129 |
| | (77.926, 159.25) | (73.094, 174.906) | (57.756, 155.994) | (49.036, 196.214) | (98.398, 159.602) |
| Cholesterol, total/HDL | 4.806 | 4.553* | 5.2 | 5.062 | 4.456 |
| | (3.68, 5.931) | (3.426, 5.68) | (3.746, 6.654) | (3.672, 6.453) | (3.831, 5.08) |

TABLE 1-continued

| Variables (geometric mean and 95% confidence limits) determined during a 21-day's study of diethylazelate in overweight male subjects | | | | |
|---|---|---|---|---|
| LDL/HDL | 3.442 | 3.201* | 3.744 | 3.582 | 3.173 |
| | (2.481, 4.403) | (2.31, 4.092) | (2.543, 4.944) | (2.543, 4.621) | (2.531, 3.816) |
| LDL/triglycerides | 0.998 | 0.893 | 1.048 | 0.804 | 0.954 |
| | (0.562, 1.434) | (0.619, 1.166) | (0.471, 1.624) | (0.556, 1.051) | (0.664, 1.244) |
| Non-cholesterol HDL/HDL | 3.799 | 3.549* | 4.196 | 4.046 | 3.446 |
| | (2.68, 4.917) | (2.434, 4.664) | (2.758, 5.633) | (2.666, 5.426) | (2.816, 4.077) |
| Triglycerides/HDL | 3.761 | 3.907 | 4.076 | 4.82 | 3.481 |
| | (2.399, 5.123) | (2.227, 5.588) | (2.299, 5.854) | (2.816, 6.824) | (2.611, 4.35) |

| | High A1c (n = 9) | FPG <100 mg/dL (n = 8) | | FPG >100 mg/dL (n = 9) | |
|---|---|---|---|---|---|
| Variable | D21 | D0 | D21 | D0 | D21 |
| Fasting plasma glucose (mg/dL) | 100.261 | 92.769 | 97.25 | 109.567 | 101.939** |
| | (91.825, 108.697) | (85.484, 100.053) | (90.903, 103.597) | (101.143, 117.99) | (94.269, 109.609)) |
| Glucose 180 min (mg/dL) | 95.128 | 89.919 | 86.494 | 109.556 | 96.1 |
| | (57.51, 132.745) | (71.388, 108.45) | (71.181, 101.807) | (68.139, 150.972) | (58.839, 133.361) |
| AUC Glucose | 25889 | 23530 | 24475 | 27867 | 26138 |
| | (18754, 33023) | (21166, 25894) | (19643, 29307) | (21824, 33910) | (20459, 31818) |
| Fasting insulin (μU/mL) | 28.9 | 20.212 | 20.95 | 31.3 | 30.289 |
| | (−1.125, 58.925) | (8.336, 32.089) | (8.242, 33.658) | (13.283, 49.317) | (1.05, 59.528) |
| AUC insulin | 25988 | 22215 | 27461 | 27405 | 26275 |
| | (14315, 37660) | (11805, 32625) | (12317, 42605) | (18567, 36243) | (16494, 36056) |
| Cholesterol, total (mg/dL) | 169.667 | 154.875 | 146.125 | 145.889 | 151.333 |
| | (136.963, 202.37) | (98.406, 211.344) | (81.035, 211.215) | (109.131, 182.646) | (122.183, 180.484) |
| LDL cholesterol (mg/dL) | 103.444 | 101 | 90.75 | 105 | 103.444 |
| | (72.805, 134.084) | (62.344, 139.656) | (49.127, 132.373) | (69.957, 140.043) | (72.805, 134.084) |
| HDL cholesterol (mg/dL) | 41.222 | 31.25 | 31.5 | 34.111 | 37 |
| | (36.728, 45.716) | (17.847, 44.653) | (14.887, 48.113) | (26.455, 41.767) | (32.641, 41.359) |
| Non-cholesterol HDL (mg/dL) | 128.444 | 111.778 | 114.333 | 123.75 | 114.625 |
| | (98.582, 158.307) | (80.892, 142.664) | (87.278, 141.389) | (78.88, 168.62) | (64.187, 165.063) |
| Triglycerides (mg/dL) | 125.222 | 122.889 | 127.667 | 113.75 | 119.875 |
| | (104.229, 146.215) | (89.197, 156.58) | (87.911, 167.422) | (64.441, 163.059) | (55.999, 183.751) |
| Cholesterol, total/HDL | 4.1* | 4.311 | 4.089 | 5.362 | 5.075 |
| | (3.502, 4.698) | (3.621, 5.001) | (3.358, 4.819) | 5.362 (4.065, 6.66) | 5.075 (3.769, 6.381) |
| LDL/HDL | 2.862** | 3.082 | 2.892 | 3.847 | 3.549 |
| | (2.255, 3.47) | (2.383, 3.78) | (2.224, 3.559) | (2.752, 4.942) | (2.527, 4.571) |
| LDL/triglycerides | 0.972 | 0.861 | 0.887 | 1.152 | 0.9 |
| | (0.687, 1.256) | (0.669, 1.054) | (0.612, 1.161) | (0.568, 1.735) | (0.608, 1.191) |
| Non-cholesterol HDL/HDL | 3.108 | 3.309 | 3.098 | 4.349 | 4.057 |
| | (2.512, 3.704) | (2.624, 3.995) | (2.376, 3.819) | (3.058, 5.641) | (2.757, 5.357) |
| Triglycerides/HDL | 3.096 | 3.693 | 3.521 | 3.837 | 4.342 |
| | (2.35, 3.843) | (2.618, 4.769) | (2.135, 4.907) | (2.133, 5.541) | (2.38, 6.304) |

D0; Day 0, pre-treatment values
D21; Day 21, post-treatment values
AUC; area under the curve
FPG; fasting plasma glucose
LDL; low density lipoprotein
HDL; high density lipoprotein
*P < 0.05; bold type
**P < 0.01; bold type
Values without paretheses: mean
Value in parentheses: 95% confidence intervals Glucose The levels of glycated hemoglobin A1c ("A1c"), which is considered as a measure of the average blood sugar level in a subject over the two or three months prior to measurement, are often measured to assess effects of oral antidiabetic agents on glucose control with the drug activity becoming apparent within the first 4 to 6 months [37]. A measurable effect on A1c was not expected in this short-term study but pre-treatment A1c levels were measured and used to assess the relative state of insulin resistance in the subjects.

Figure 1:
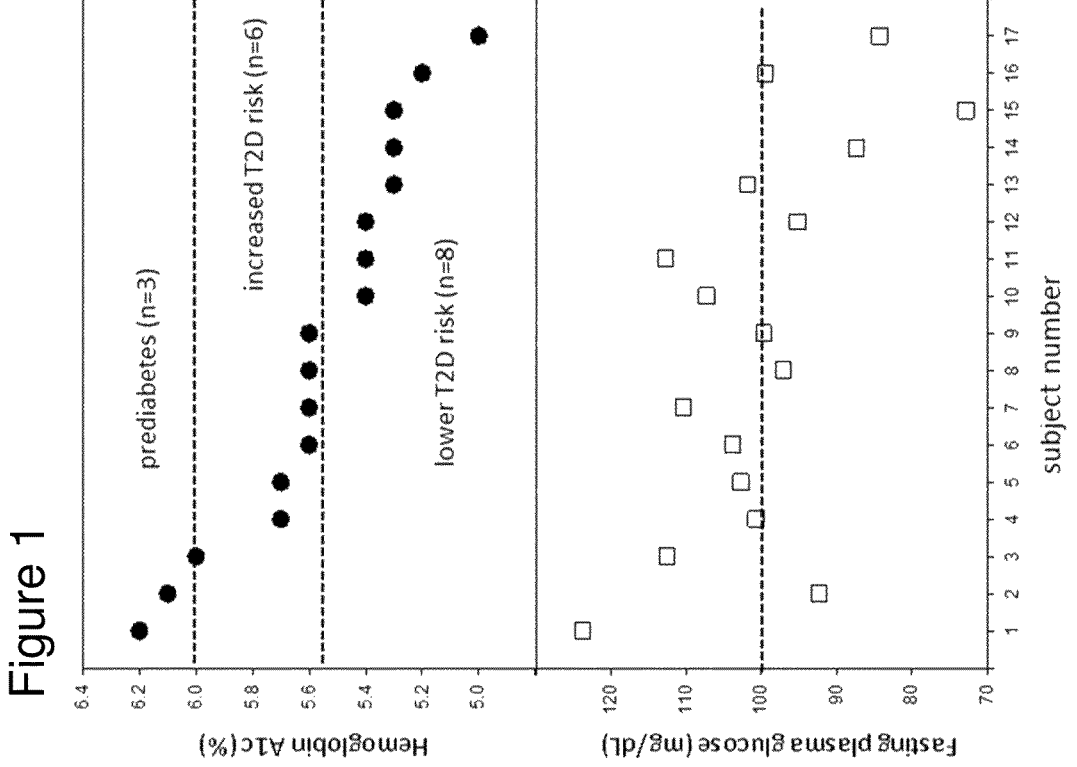
FIG. 1 shows stratification by glucose markers of the study cohort of 17 subjects described in Example 1. Stratification shown by descending hemoglobin A1c levels, filled circles; corresponding fasting plasma glucose levels, open squares.

When the cohort was sorted by descending A1c values (FIG. 1), 3 subjects with A1c's of 6.2, 6.1 and 6.0% were classified as prediabetic and 6 subjects with A1c's of 5.6-5.7% as having an increased risk for T2D. This subgroup of 9 subjects with A1c≥5.6% is referred to as 'high A1c' herein. The remaining 8 subjects with A1c's of 5.0-5.4% and having a lower risk for T2D were referred to as "low A1c". Stratification by fasting plasma glucose levels showed that 9 subjects≥100 mg/dL ('high glucose') and 8 subjects were below the threshold of 100 mg/mL ("low glucose").

For measuring the effect of DEA on blood glucose, an assessment of fasting plasma glucose levels was relied upon, which is a measure that is commonly used as an indication that a subject may be diabetic. A level under 100 mg/dL is considered clinically normal [38] while the range between 100 and 125 mg/dL is indicative of prediabetes [39]. At the threshold of 100 mg/dL the human body begins to have a compromised insulin response to glucose shock [40]. The OGTT was used, in which a standard dose of glucose was ingested by mouth, and blood samples were taken at specified time points after ingestion. Plasma blood glucose measurements were then obtained as a means of understanding the pharmacodynamic effects of DEA.

Figure 2B:
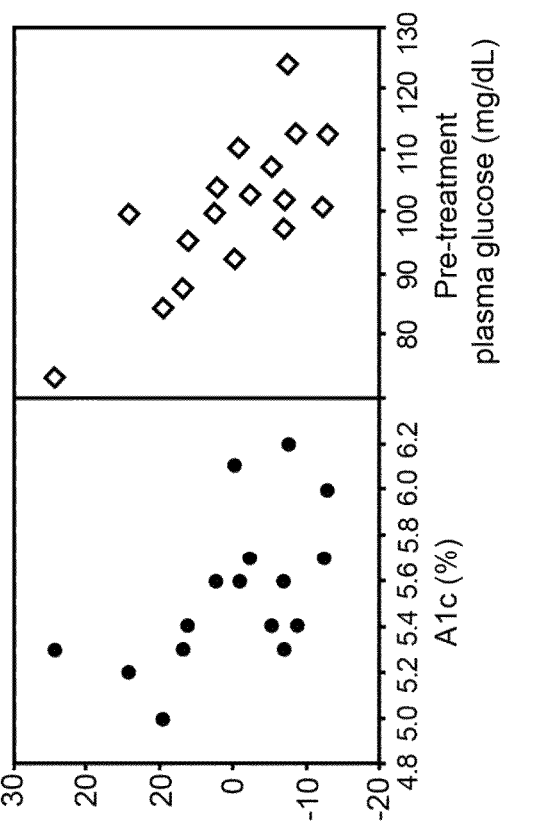
FIGS. 2A and 2B show effects of DEA on fasting plasma glucose on subjects described in Example 1.
Figure 2A:
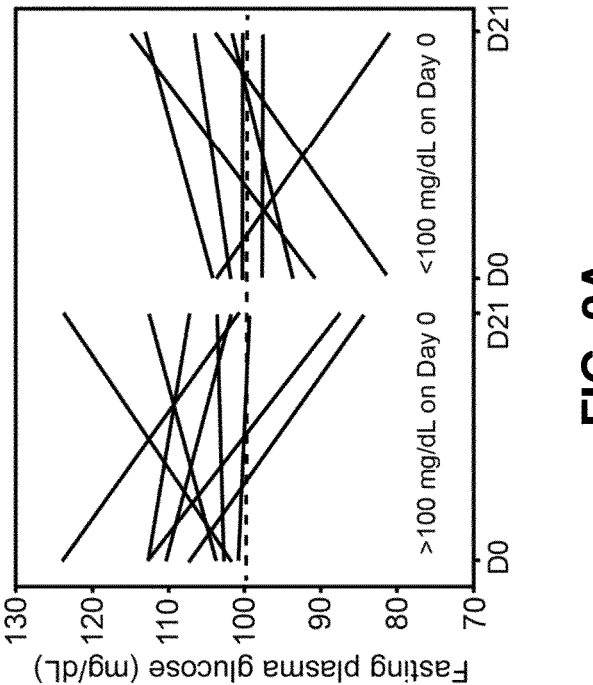

When the entire cohort of 17 subjects was analyzed as a group, post-treatment fasting glucose increased slightly yet insignificantly by 0.11 mg/dL (p=0.962; p=0.96. However, fasting glucose decreased in subjects both in the high glucose and high A1c groups. For those with an HbA1c≥5.6%, the average decrease was 4.25 mg/dL (p=0.128; p=0.22). The largest decrease occurred in the 8 subjects with a fasting glucose≥100 mg/dL in whom the fasting glucose decreased by an average 6.06 mg/dL (p=0.033; p=0.06) (see FIG. 2A). The decrease in fasting glucose after treatment was moderately correlated with the pre-treatment A1c (p=−0.551) and strongly correlated with the fasting plasma glucose pre-treatment (p=−0.755) (FIG. 2B).

Figures 3A, 3B:
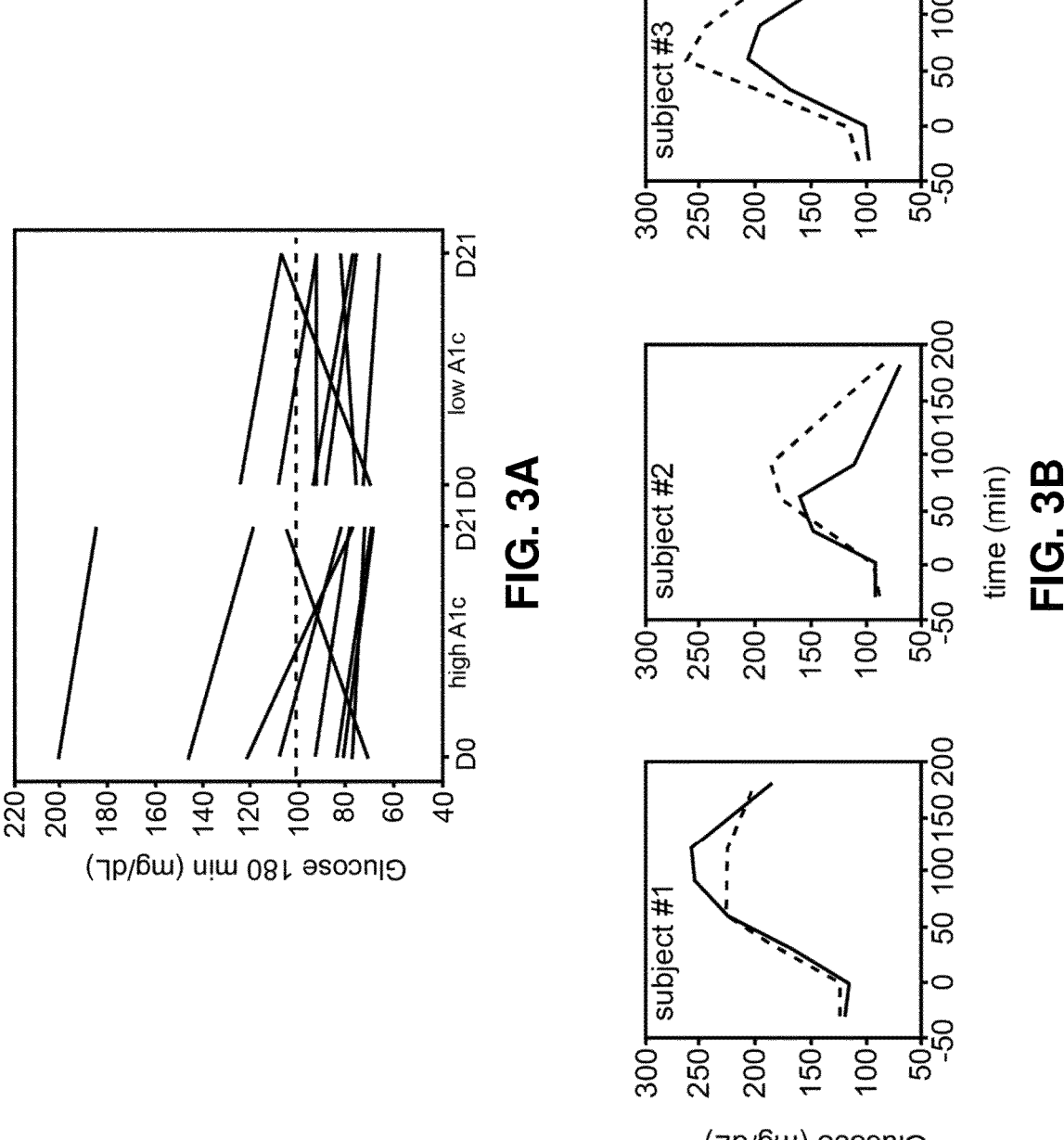
FIGS. 3A and 3B show effects of DEA treatment on glucose levels in the fasting oral glucose tolerance test (OGTT) on subjects described in Example 1.

Modulation of postprandial glucose level is of interest for drug development given that even transient hyperglycemia has long-term impact on cardiovascular and kidney diseases, neuropathy and retinopathy [42, 43]. FIG. 3A shows the effects of DEA on glucose at 180 min in the high and low A1c subject groups. In a subset of 12 subjects DEA decreased glucose levels at 180 minutes compared to the average pre-OGTT glucose levels on Day 21, by 2.4% to 31.5% with an average decrease of 21.7% (p<0.001; median decrease 25.3%). For the entire cohort, the average decrease at 180 minutes was not significant (9.14%; p=0.136; 0.057) due to a single outlier (subject #1) who showed a 58.6% increase. This particular subject had an average fasting insulin of 77.45 µU/mL and may have been leptin resistant which may interfere with the mechanism of action of DEA (unpublished data). Excluding that subject, the remaining 16 subjects exhibited a decrease in 180 min plasma glucose of 13.5% after treatment (p=0.002; 0.003).

The effects of DEA can be appreciated by the analysis of three individual prediabetic cases. As shown in FIG. 3B, the glucose disposal profile of subject #1 (A1c 6.2%) increased post-treatment but the fasting and 180 min glucose levels decreased from 123.8 to 116.3 mg/dL and from 200.0 to 184.5 mg/dL, respectively. Subjects #2 (A1c 6.1%) and #3 (A1c 6.0%) experienced improvement in glucose clearance rates at 180 min (from 88.3 to 69 mg/dL and from 146 to 119 mg/dL, respectively).

Insulin

Figures 4A, 4B:
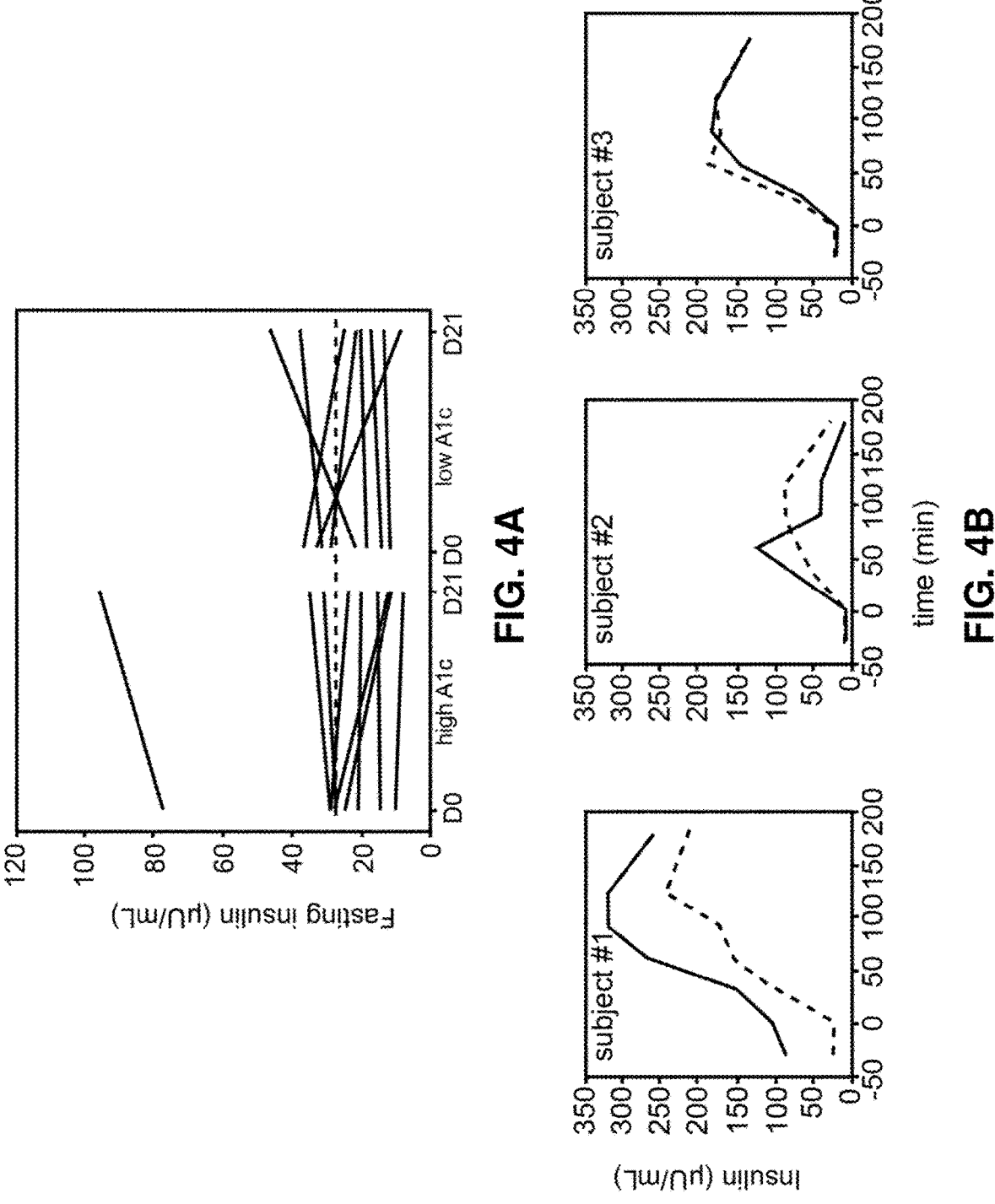
FIGS. 4A and 4B show the correlation of effect of DEA treatment on fasting insulin and the A1c levels studied subjects described in Example 1.

In the prediabetic state and more so in T2D, the body does respond to insulin properly leading to insulin resistance. Subjects with insulin resistance show elevated blood glucose and insulin levels. In our study, fasting insulin spanned mostly normal ranges of <25 µU/mL before and after the treatment in the high and low A1c groups (FIG. 4A) and the inter-group differences were not significant. An outlier was a single subject (#1) in the high A1c group (see also FIG. 4B) whose pre-treatment average fasting insulin increased from 77.45 µU/mL to 96.15 µU/mL post-treatment. The remaining 16 subjects experienced a decrease of fasting insulin of 13.4% (p=0.007; 0.009)

In a subset of 8 subjects (#2-4, 8-11, and 13) from both high and low (≥5.3%) A1c groups, DEA treatment significantly (p=0.004, p=0.008) decreased mean fasting insulin by 37.8% (a median decrease of 42.5%). The apparent non-responders including the outlier (subject #1) had otherwise either normal pre-treatment levels of fasting insulin, plasma glucose, and/or lipid markers. Considering all 17 subjects, the decrease was 0.7 µU/mL (p=0.916; p=0.963). In the high fasting plasma glucose group, the decrease was 2.97 µU/mL (p=0.752; p=0.855) and in the high A1c group, the decrease was 0.84 µU/mL (p=0.916; p=0.963).

The effects of treatment on individual insulin profiles in 3 prediabetic subjects (FIG. 4B) parallel their glucose response (FIG. 3B) and suggest that in cases such as subject #1 with advanced prediabetes, the dose and/or duration of the treatment need to be further optimized.

The median insulin area under the curve (AUC) decreased by 1663.5 in the high A1c group but increased by 3380.25 in the low A1c group. Neither change was statistically significant. The glucose and insulin responses to DEA were correlated for the entire cohort. Overall, DEA increased the correlation between AUCs for glucose and insulin from 0.229 pre-treatment to 0.523 post-treatment (data not shown).

Lipid Panel

Figure 5B:
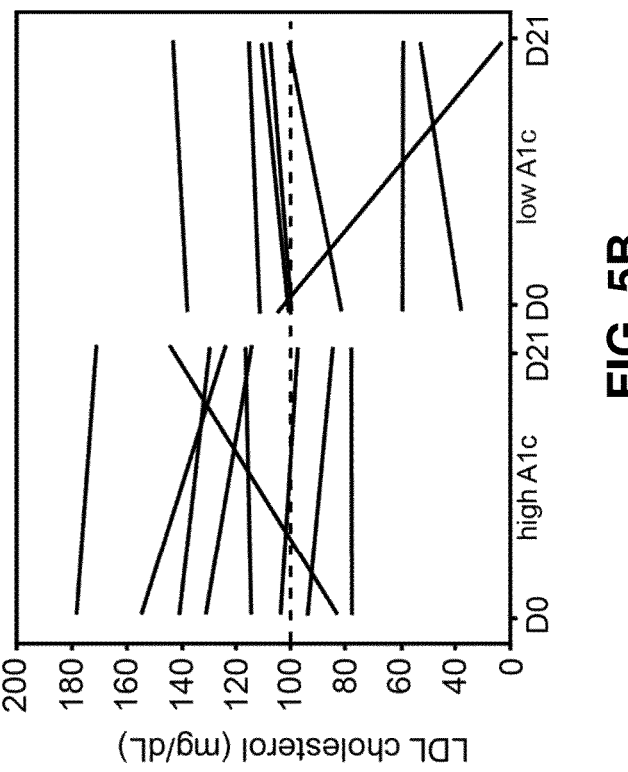
Figure 5A:
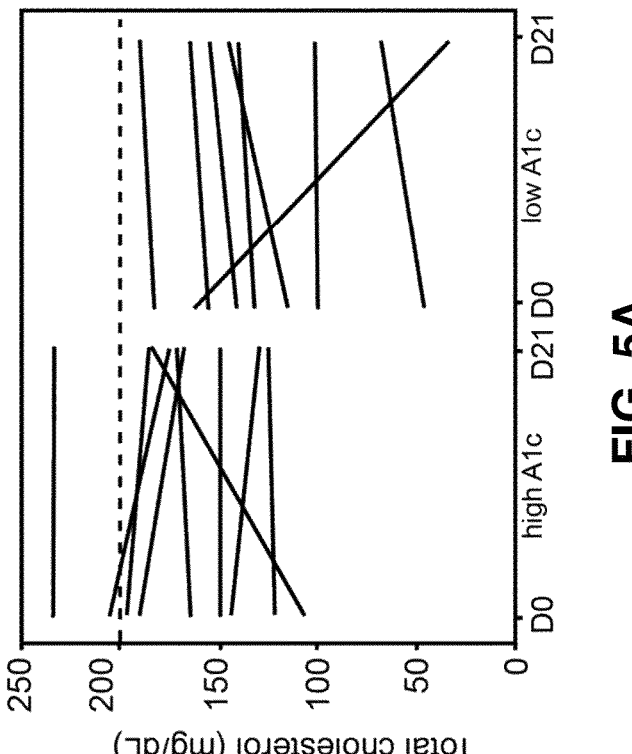

When the lipid data were analyzed for the entire cohort, DEA did not exert statistically significant effects on any endpoint considered singly: total cholesterol, LDL, HDL, non-cholesterol HDL, and triglycerides (see Table 1). However, the pharmacological effects of DEA become noticeable between the high and low A1c groups (FIGS. 5A-5E). Abnormal total cholesterol (>200 mg/dL) in two subjects in the high A1c group decreased or returned to normal levels. The median total cholesterol decreased by 1 mg/dL in the high A1c group but increased by 9 mg/dL in the low A1c group (FIG. 5A). LDL showed a decreasing trend toward normal values of <100 mg/dL in the high A1c group but less so in the low A1c group (FIG. 5B). HDL and non-cholesterol HDL were within the normal range (>40 mg/dL and <130 mg/dL) in all subjects and were non-significantly affected by the treatment (FIGS. 5C and 5D). Elevated triglycerides decreased post-treatment to normal levels in 8 subjects including two subjects with abnormal triglycerides of >150 mg/before treatment in the high A1c group (FIG. 5E).

Figures 6A, 6B, 6C:
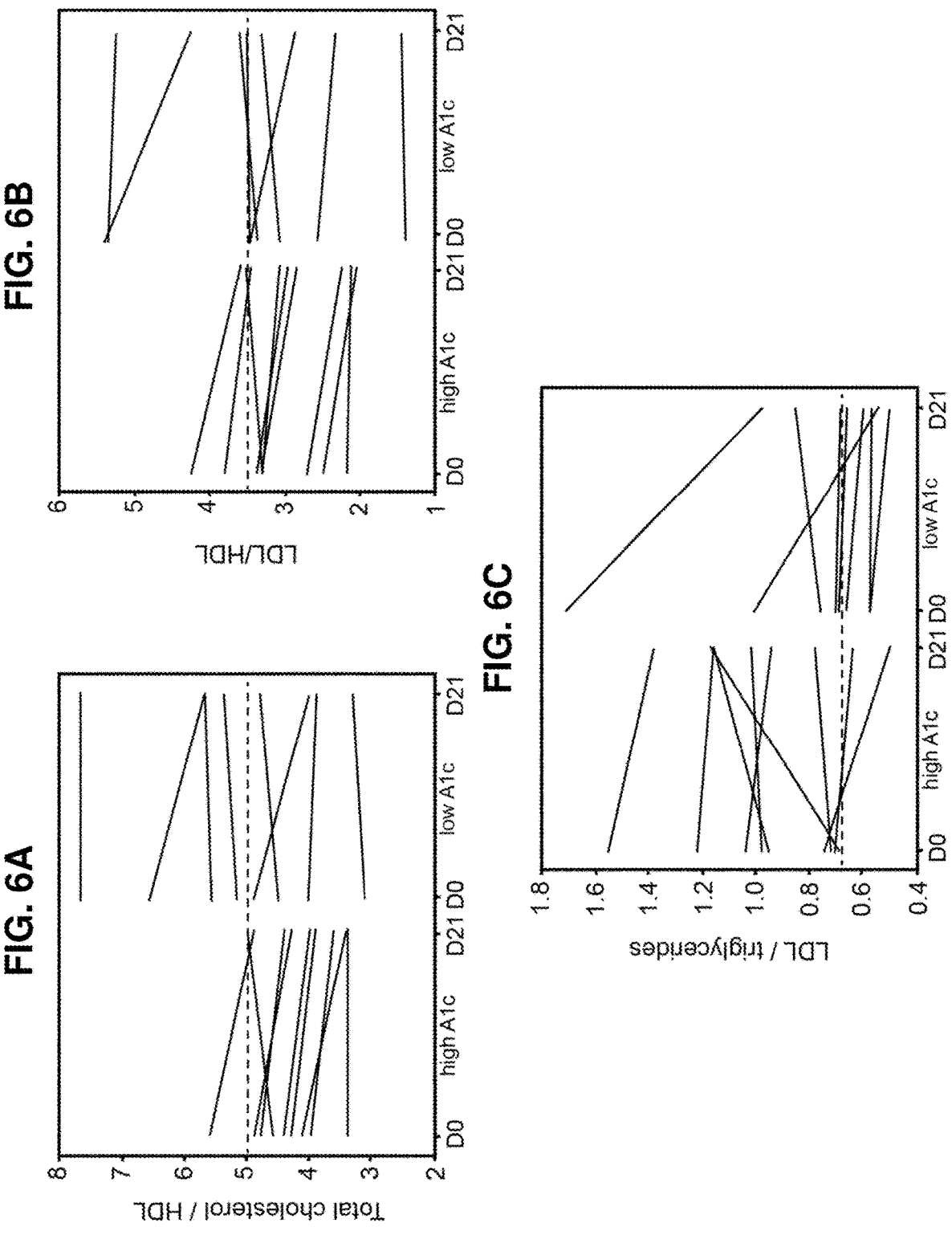
FIGS. 6A-6E show the effect of DEA treatment on the ratios of lipid markers on subjects described in Example 1.
Figure 6E:
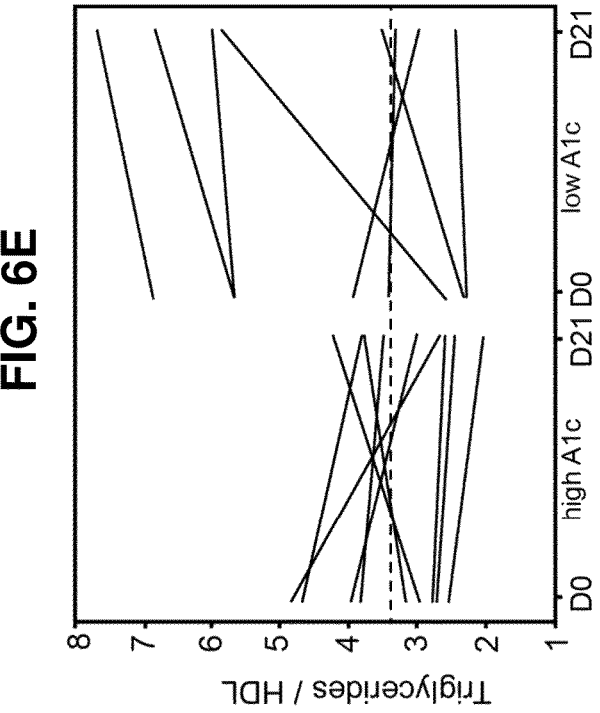
Figure 6D:
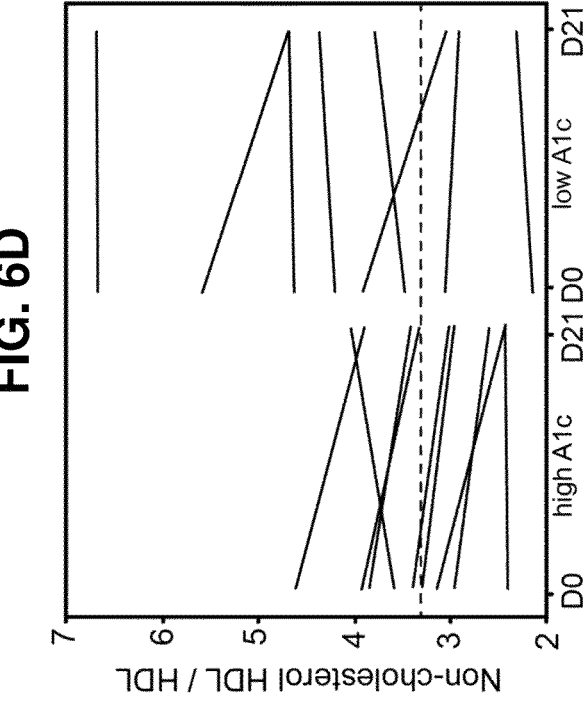

In contrast, substantial differences were observed in the lipid ratios. While the total cholesterol remained largely unaffected by DEA treatment, the ratio of total cholesterol/ HDL decreased significantly by 5.36% (p=0.025; p=0.041). This decrease was primarily driven by the high A1c group which exhibited a 7.99% decrease (p=0.017; p=0.068); see also FIG. 6A. Likewise, LDL/HDL decreased in all 17 subjects by 6.46% (p=0.011; p=0.02). Among the high A1c subjects, this decrease was 9.8% (p=0.008; p=0.02); see also FIG. 6B. The ratios of LDL/triglycerides and triglycerides/ HDL did not differ significantly between the high and low A1c groups, but several individuals experienced clear improvement (FIGS. 6C and 6E). Of interest was the effect of treatment on the ratio of triglycerides/HDL, a predictor of cardiovascular disease [39], which increased by 15% in the low A1c (from 3.9 to 4.6 post-treatment) but decreased by 11% (from 3.4 to 3.0) in the high A1c group. A significant improvement was also observed in the non-cholesterol HDL/HDL ratio, a predictor of onset of non-alcoholic fatty liver disease (NAFLD) [45], which decreased by 6.6% in the entire cohort (p=0.025; p=0.057) and by 9.8% in the high A1c group (p=0.025; p=0.074); see also FIG. 6D.

Figure 7:
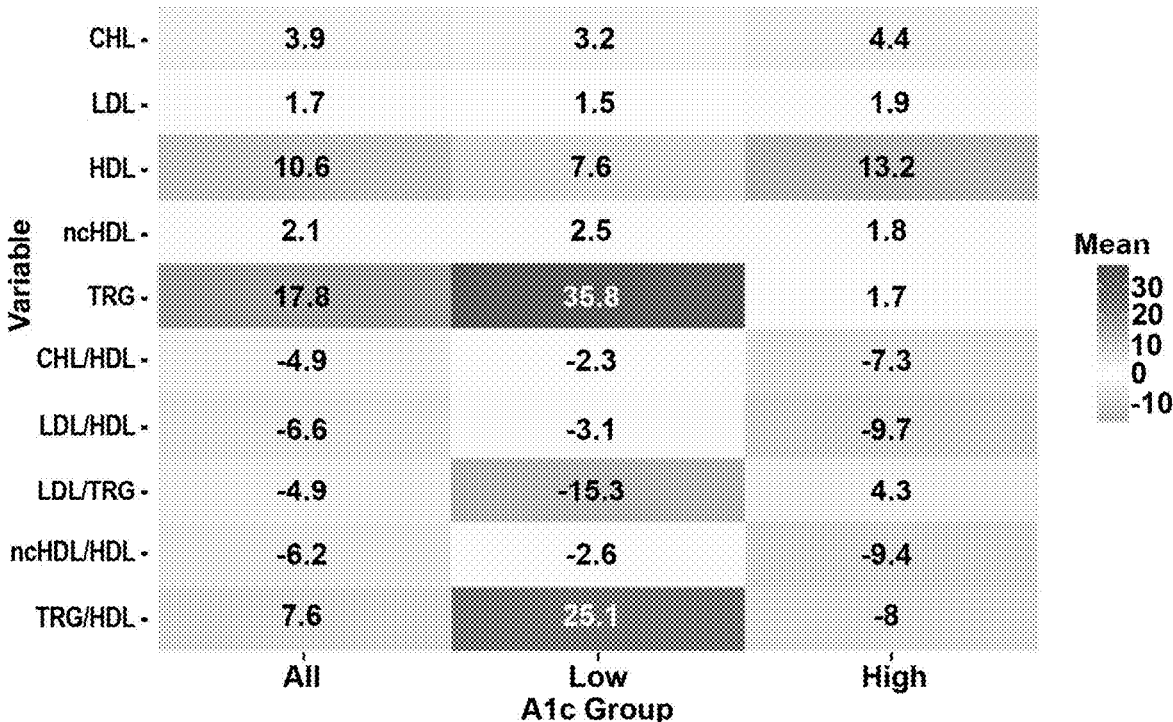
FIG. 7 shows the effect of DEA treatment on the lipid markers in the cohort of subjects described in Example 1. Left column: all subjects. Middle column: low A1c subgroups. Right column: High A1c subjects. Mean percentage changes in the levels of the endpoints are presented in grayscale and the numerical values are shown for all endpoints. The darker ranges (above "10" to "30") correspond to increased values post-treatment and the lighter ranges (below "0" to "−10") correspond to the decreased values.

FIG. 7 illustrates the lipid panel results for the entire cohort and both the low and high A1c groups. Large differences between the A1c subgroups were evident for HDL/LDL, total cholesterol/HDL and triglycerides. Overall, the lipid panel differences between the high and low A1c groups suggested an adaptive response to DEA.

Data mining of the results disclosed in this Example 1 using several statistical analytic methods confirmed the statistical significance of DEA effects on markers (e.g., plasma lipid levels, plasma lipid ratios, and plasma glucose levels, as disclosed herein) of dyslipidemias and insulin resistance. For fasting plasma glucose, the DEA effects were significant in prediabetic subjects and those with elevated risk for T2D (e.g., the high A1c subgroup and the high fasting plasma glucose (FPG) groups). The apparent non-responders did not have clinical indicators of T2D or pre-diabetes and as such would not be considered a population needful of antidiabetic therapy. The discordant responses in the test group suggest that normal subjects do not benefit from DEA and that those with signs of dyslipidemia or insulin resistance show improvements in their clinical indices in response to DEA treatment. The individuals with higher insulin resistance experienced even greater improvement upon DEA treatment. Subjects classified in the range of T2D risk or prediabetes evidenced improvement not only in the plasma glucose but also insulin levels. These results suggest that upon DEA treatment the pancreas functions less strenuously in producing insulin and is less likely to 'burn out' as seen in late T2D [46].

A comparison of certain effects of metformin and DEA as presented herein revealed many similarities and advantages of DEA over metformin as provided in Table 2, below.

observed in the diagnostic lipid ratios of cholesterol/HDL, LDL/HDL [59], and non-cholesterol HDL/HDL [60] in the entire cohort of subjects studies. These subjects were either overweight or obese and were thus at risk for conditions and diseases associated with metabolic syndrome, including metaflammation [61], NAFLD and NASH [62], type II diabetes, cardiovascular disease, stroke, coronary artery disease, atherosclerosis, and cancer.

At present there are no approved drugs to treat NAFLD or NASH, and lipid-based complications of metabolic syndrome are currently treated with statins [63]. No overlap was found in statistically significant endpoints for DEA administration disclosed herein and statins except for decreased LDL/HDL ratios for DEA (9.8%, 21-day study disclosed herein) versus statins (26.7%, 18-24 month study [64]).

TABLE 2

Comparison of diethylazelate and metformin effects on glucose, insulin and lipid markers

| Variable | DEA | Metformin | Study duration | Reference |
|---|---|---|---|---|
| Fasting plasma glucose | *5.9% decrease (apparent responders) | 4.5% decrease | 8 weeks (T2D risk) | 48 |
| Hypoglycemia | no effect | infrequent event | multiple studies | 51 |
| Fasting insulin | *38% decrease (apparent responders) | 14.4% decrease | 8 weeks (T2D risk) | 48 |
| HDL | 8.7% increase | 5% increase | 1 year (T2D) | 52 |
| Cholesterol/HDL | *5.4% decrease (all), *8% (high A1c) | 9.2% decrease | 4 weeks (T2D) | 47 |
| LDL | 4.3% decrease (all), 2% (high A1c) | 5.6% decrease | 1 year (T2D) | 52 |
| LDL/HDL | *6.5% decrease (all),*9.8% (high A1c) | 11.7% decrease | 1 year (T2D) | 52 |
| Side effects | mild transient diarrhea (1/17 subjects) | severe gastrointestinal effects | multiple studies | 53 |

*Significant effect in this stud

For example, in a 28-day study in 16 subjects with Type II diabetes, metformin reduced fasting glucose but had no effect on insulin levels [47]. In a meta-analysis of 4750 prediabetic subjects in randomized trials of at least 8 weeks, metformin reduced fasting glucose (−4.5%), fasting insulin (−14.4%), and LDL (−5.6%) and increased HDL (5.0%) compared to placebo or no treatment [48]. In the 21-day study presented herein, fasting plasma glucose decreased by 5.9% and fasting insulin decreased by 38%. In a 15-year study metformin reduced the incidence of diabetes compared to placebo by 17% and the subset that benefited most included subjects with higher baseline plasma glucose or A1c [49]. The data presented herein indicate that DEA may be even more effective in treating or preventing more advanced diabetic pathologies, as well as dyslipidemias and conditions or disease associate wherewith.

Neither metformin nor DEA administration as presented herein induced hypoglycemia. The effects presented herein of DEA on lipid levels were at least qualitatively similar to, and in many respects superior to, metformin [47]. For example, DEA significantly improved the LDL/HDL ratio and the decrease of 9.8%, that was achieved in 3 weeks was comparable with an 11.7% decrease reported after 1 year of treatment with metformin in statin-naïve individuals [52]. Additionally, oral administration of DEA was well tolerated, while metformin causes severe gastrointestinal side effects in 1 of 4 users and 5% patients cannot tolerate metformin at all [53].

Metformin has been suggested as a treatment for obesity by inducing weight loss [54], diminishing risk of cardiovascular disease [55] and cancer [56], and promoting life extension [57, 58]. The results presented herein, which were by many measures superior to that reported with metformin, demonstrate utility of DEA in these indications and other diseases or conditions associated therewith, as well.

Unlike the glucose and insulin effects of DEA in subjects with higher insulin resistance, significant improvement was However, statins have been reported to increase hyperglycemia and risk for type II diabetes [65] especially on a high carbohydrate diet and their adverse effects include severe muscle condition; rhabdomyolysis, further exacerbated by metabolic syndrome [67]. Thus, subject populations that cannot tolerate statins may benefit from DEA treatment that may lower the risk of progressive diseases initiated and driven by dyslipidemia.

Example 2

Described in this example is an evaluation of the effects of alkyl azelates, such as DEA, on certain markers of insulin resistance and dyslipidemia, namely, blood plasma glucose, insulin levels and/or lipid levels [30], when administered either for buccal delivery or for gastric delivery in a male subject, with diet induced insulin resistance and diabetes with a BMI of approximately 27.

Materials and Methods

Diethyl azelate was synthesized from azelaic acid and ethyl alcohol sing the standard acid-catalyzed esterification followed by fractional distillation to produce DEA to 99% purity as determined by chromatography-mass spectrometry (GC-MS). The 99% distilled DEA distillation product was administered in unformulated, unencapsulated, etc. form (i.e., "as is") for buccal delivery as indicated below.

For gastric delivery, the 99% DEA distillation product was placed in a hard gelatin capsule, size 00 (PureCaps USA, Philmont, NY) and administered for gastric delivery by swallowing with a drink of water.

Other azelaic acid esters are synthesized from azelaic acid and respective alcohols (methyl, propyl, isobutyl, 1-, 2—, and 3-pentyl, and cyclohexyl) using the standard acid-catalyzed esterification followed by fractional distillation to produce; DMA, DIPA, DiBuA, DIPA, D2PA, and D3PA.

Fasting blood glucose levels were measured using UniStrip blood glucose test strips (UniStrip Technologies LLC, Charlotte, NC) and OneTouchUltra 2 blood glucose meter (LifeScan OneTouch, Tampa. FL).

Glycated hemoglobin A1c (A1c) blood levels were measured using A1C Now$^+$ sample dilution kit, test cartridge and the monitor (Polymer Technology Systems, Inc., Indianapolis, IN) according to the manufacturer's instructions.

Fasting blood levels of cholesterol, high density lipoprotein (HDL) cholesterol, and triglycerides were measured using Lipid Panel PTS test strips and CardioChek P-A test system (Polymer Technology Systems, Inc., Indianapolis, IN) according to the manufacturer's instructions.

Results

Figure 8:
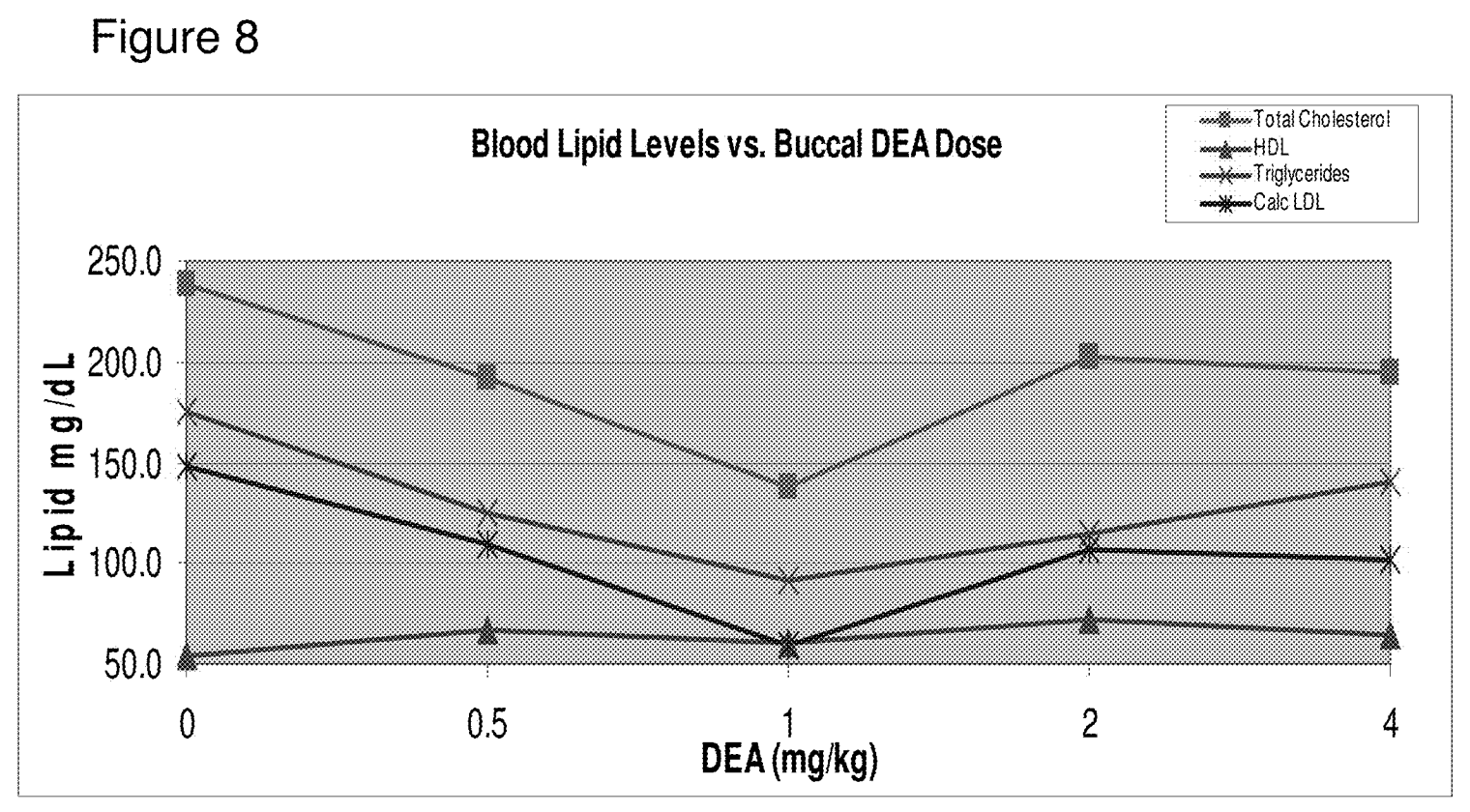

FIG. 8 shows the effect of buccal DEA delivery on measured concentrations (in mg/dL) of total cholesterol, high density lipoprotein, (HDL), triglycerides, and calculated LDL (Calc LDL) as a function of DEA dose, provided at 0 mg/kg, 0.5 mg/kg, 1 mg/kg, 2 mg/kg, and 4 mg/kg. The results demonstrate that total cholesterol, triglycerides, and calculated LDL were all lowered in response to buccal delivery at all administered DEA amounts relative to the levels observed when no DEA was administered (i.e., "0" mg/kg DEA). More pronounced lowering effects of these lipids were observed with the 0.5 mg/kg, 1 mg/kg, and 2 mg/kg DEA doses, with the greatest lowering effect observed at the 0.5 mg/kg DEA dose. The results also demonstrate that HDL levels were increased at all DEA doses tested relative to the level observed when no DEA was administered (i.e., "0" mg/kg DEA). Overall, these results demonstrate that buccal delivery of DEA results in improvement in lipid profile/lipid levels for all lipids measured.

Figure 9:
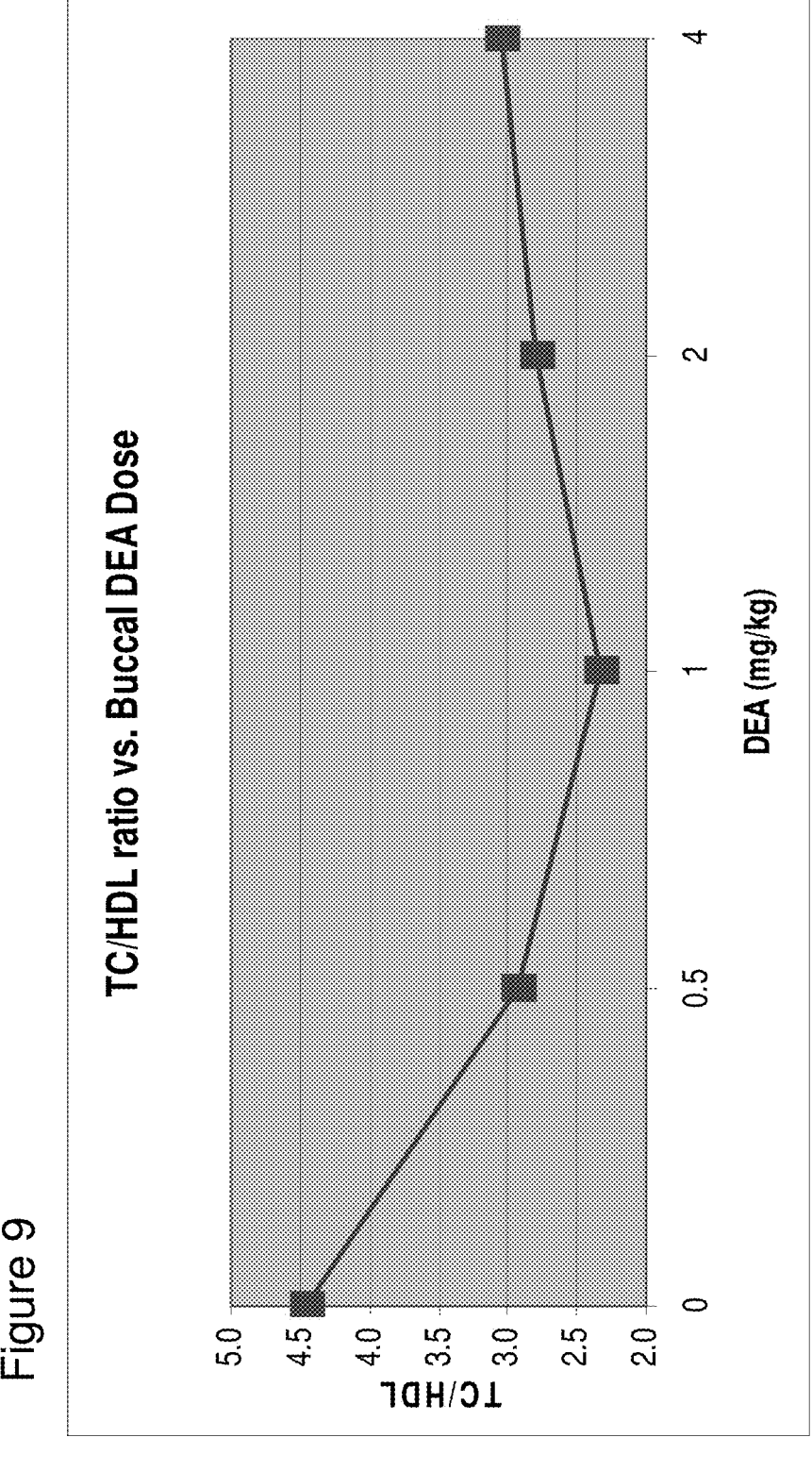
FIG. 9 shows the effect of DEA administration via buccal delivery on total cholesterol/high density lipoprotein (TC/ HDL) ratio as a function of the indicated DEA dosages, as described in Example 2.

FIG. 9 shows the effect buccal DEA delivery on total measured cholesterol concentration/high density lipoprotein concentration (TC/HDL) ratio as a function of DEA dose, provided at 0 mg/kg, 0.5 mg/kg, 1 mg/kg, 2 mg/kg, and 4 mg/kg. The results demonstrate lowered (i.e., improved) TC/HDL ratio upon buccal delivery of DEA at all tested DEA amounts relative to the TC/HDL ration measured with no DEA administration, with more TC/HDL ratio-lowering effects observed with the 0.5 mg/kg, 1 mg/kg, and 2 mg/kg DEA doses. The TC/HDL ratio was lowered the most with the 0.5 mg/kg DEA dosage amount.

Figure 10:
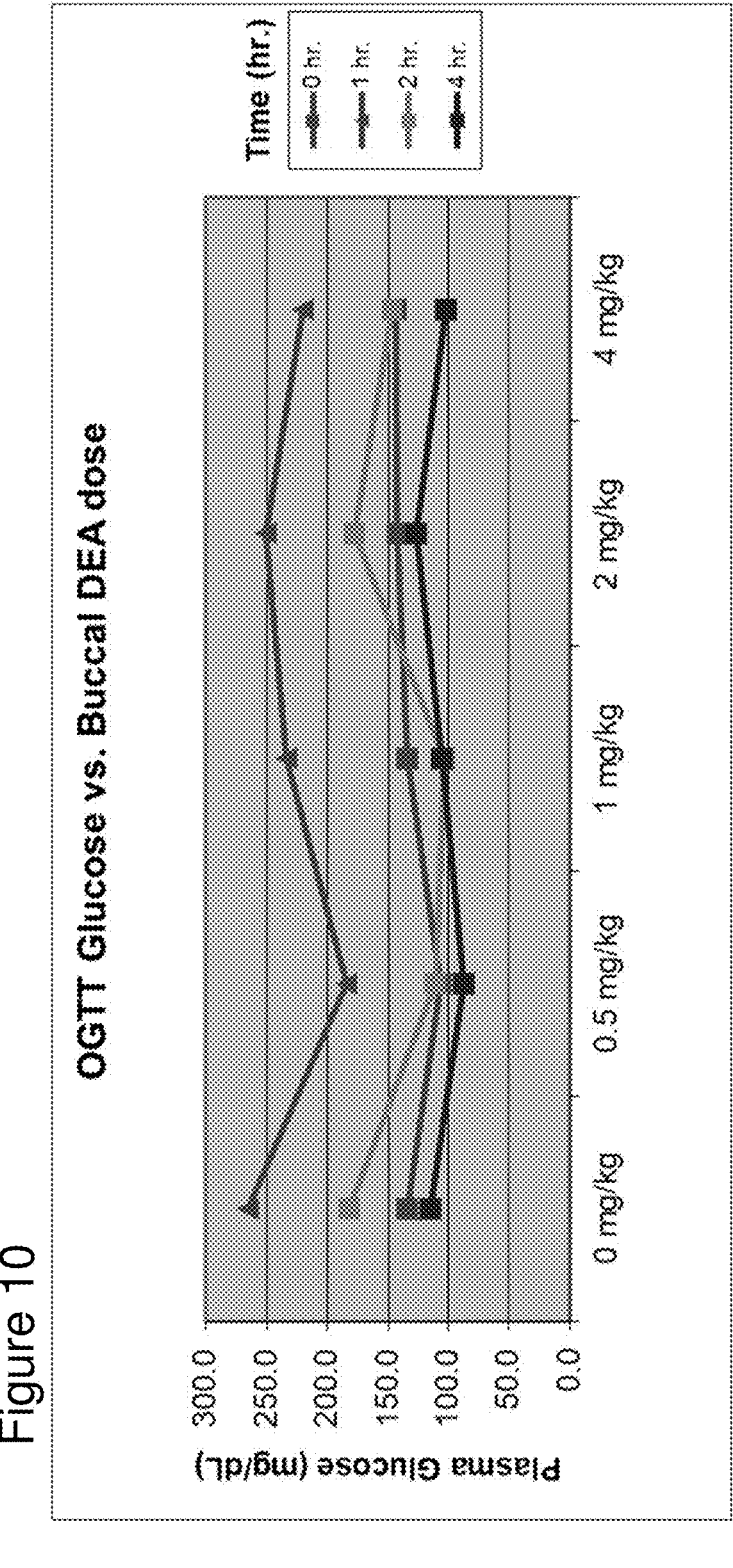
FIG. 10 shows the effect of DEA administration via buccal delivery on plasma glucose concentrations measured at the indicated time points after ingestion of a standard glucose dose in an OGTT as a function of the indicated DEA dosages, as described in Example 2.

FIG. 10 shows the effect of buccal delivery of 0 mg/kg, 0.5 mg/kg, 1 mg/kg, 2 mg/kg, and 4 mg/kg of DEA on plasma glucose concentrations (mg/dL) in the setting of (i.e., "during") an OGTT measured at 0 hour, 1 hour, 2 hours, and 4 hours after ingestion of 75 grams of glucose in 300 mL volume. The results demonstrate that buccal administration of DEA lowered (improved) plasma glucose levels in the setting of OGTT, with the most pronounced lowering (improvement) observed at 0.5 mg/kg and 1 mg/kg DEA dosage amounts.

Figure 11:
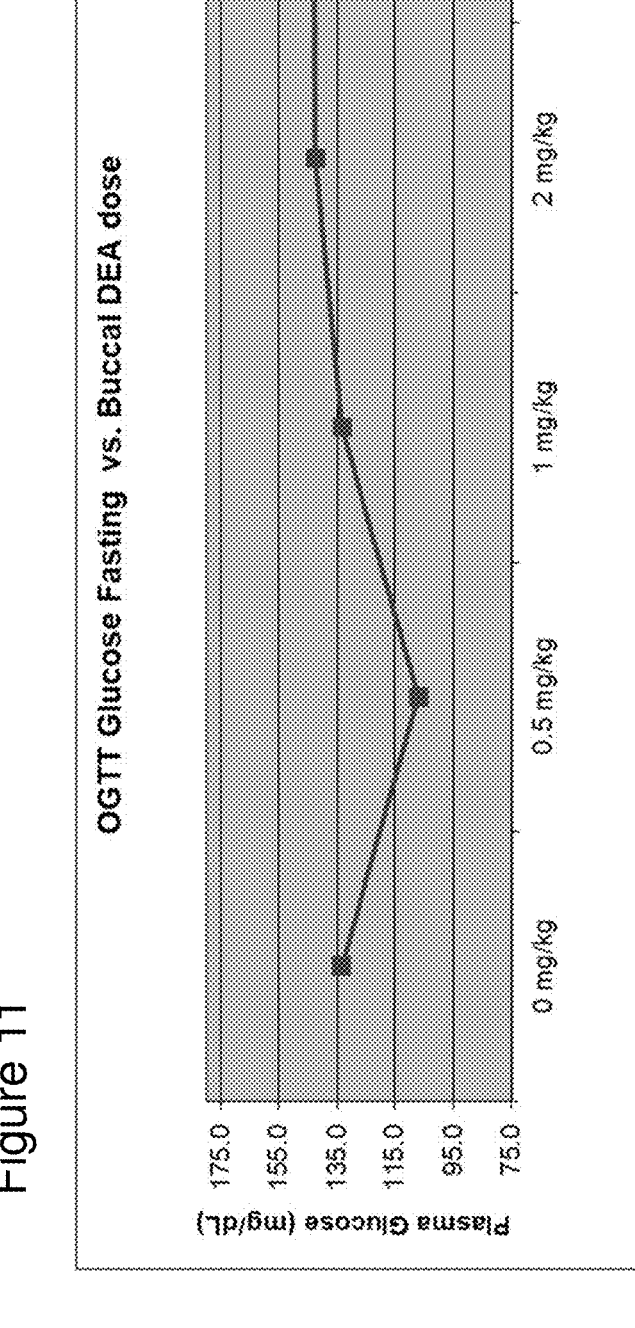
FIG. 11 shows the effect of DEA administration via buccal delivery on plasma glucose concentrations measured at the indicated time points after ingestion of a standard glucose dose in an OGTT under fasting conditions as a function of the indicated DEA dosages, as described in Example 2. Glucose administration provided at t=0. First glucose measurement taken at t=0, with subsequent glucose measurements taken at t=1, t=2 and t=4 hours.

FIG. 11 shows the effect of buccal delivery of 0 mg/kg, 0.5 mg/kg, 1 mg/kg, 2 mg/kg, and 4 mg/kg of DEA on plasma glucose concentrations (mg/dL) in the setting of (i.e., "during") an OGTT. The results demonstrate that buccal administration of DEA lowered (improved) plasma glucose levels in the setting of a fasting OGTT, with the most pronounced lowering (improvement) observed at 0.5 mg/kg and 1 mg/kg DEA dosage amounts.

Figure 12:
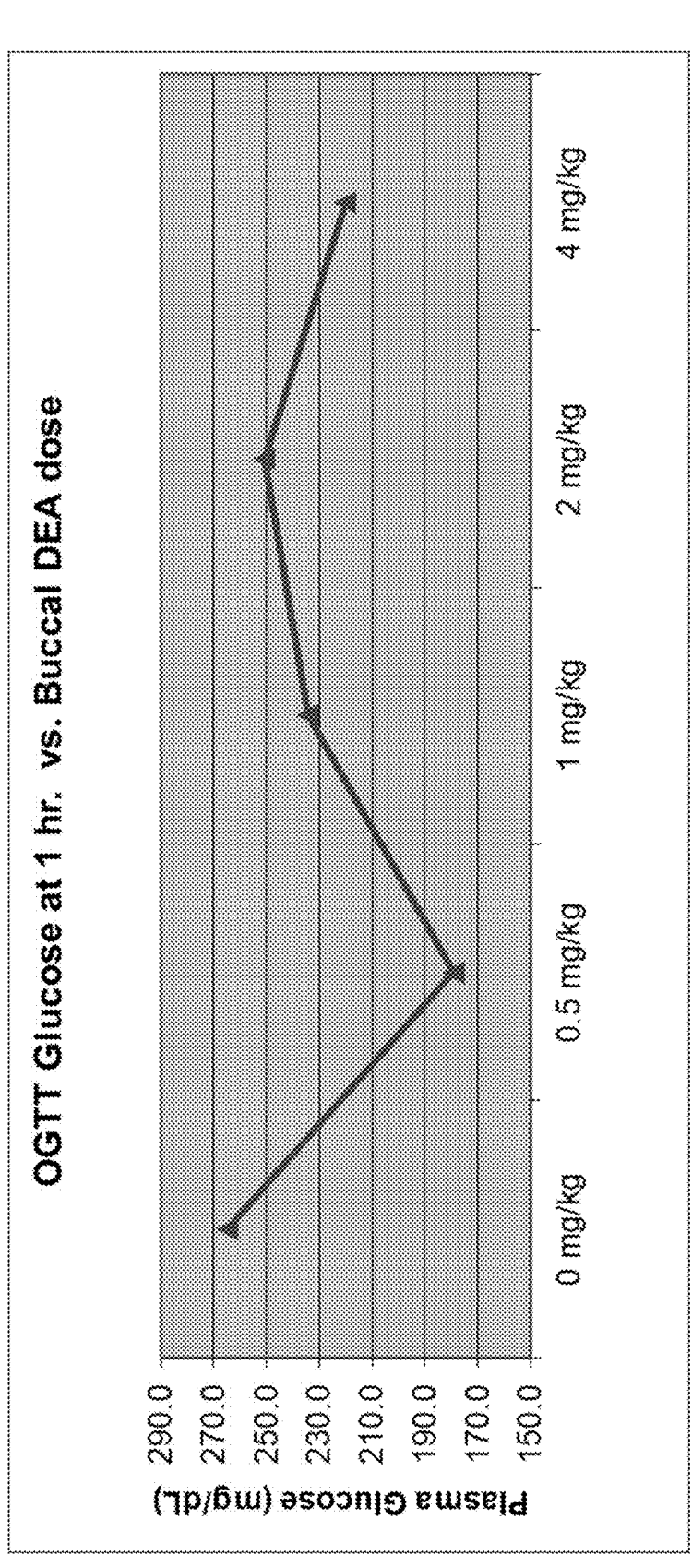
FIG. 12 shows the effect of DEA administration via buccal delivery on plasma glucose concentrations measured one hour after ingestion of a standard glucose dose in an OGTT as a function of the indicated DEA dosages, as described in Example 2.

FIG. 12 shows the effect of buccal delivery of 0 mg/kg, 0.5 mg/kg, 1 mg/kg, 2 mg/kg, and 4 mg/kg of DEA on plasma glucose concentrations (mg/dL) in the setting of (i.e., "during") an OGTT measured at 1 hour after ingestion of 75 grams of glucose in 300 mL volume. The results demonstrate that buccal administration of DEA lowered (improved) plasma glucose levels in the setting of OGTT at all DEA dosage amounts, with the more pronounced lowering (improvement) observed at 0.5 mg/kg, 1 mg/kg, and 4 mg/kg DEA dosage amounts, and the most pronounced lowering (improvement) at the 0.5 mg/kg DEA dosage amount.

Figure 13:
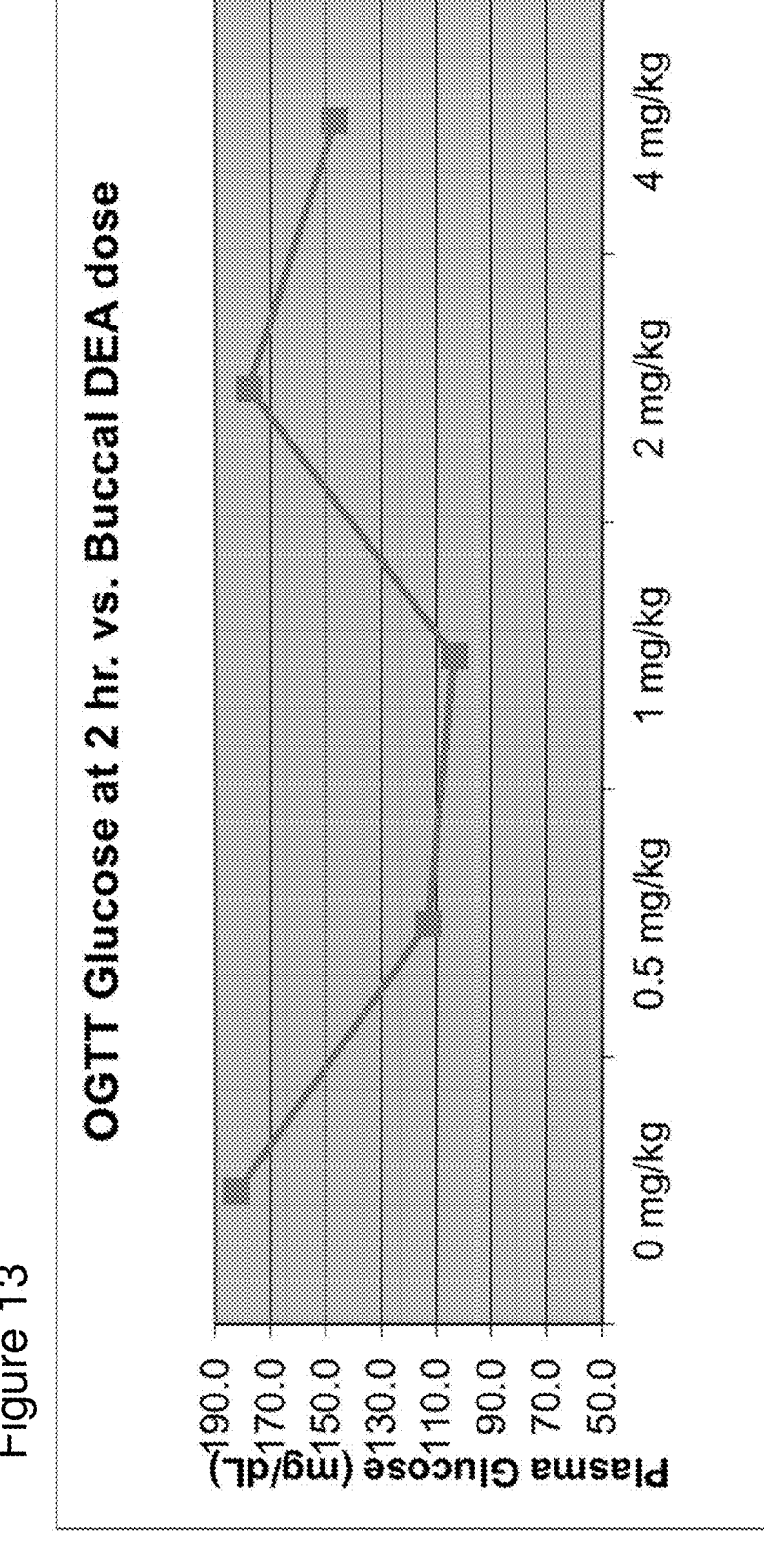
FIG. 13 shows the effect of DEA administration via buccal delivery on plasma glucose concentrations measured two hours after ingestion of a standard glucose dose in an OGTT as a function of the indicated DEA dosages, as described in Example 2.

FIG. 13 shows the effect of buccal delivery of 0 mg/kg, 0.5 mg/kg, 1 mg/kg, 2 mg/kg, and 4 mg/kg of DEA on plasma glucose concentrations (mg/dL) in the setting of (i.e., "during") an OGTT measured at 2 hours after ingestion of 75 grams of glucose in 300 mL volume. The results demonstrate that buccal administration of DEA lowered (improved) plasma glucose levels in the setting of OGTT at all DEA dosage amounts, with the more pronounced lowering (improvement) observed at 0.5 mg/kg, 1 mg/kg, and 4 mg/kg DEA dosage amounts, and the most pronounced lowering (improvement) at the 0.5 mg/kg and 1 mg/kg DEA dosage amounts.

Figure 14:
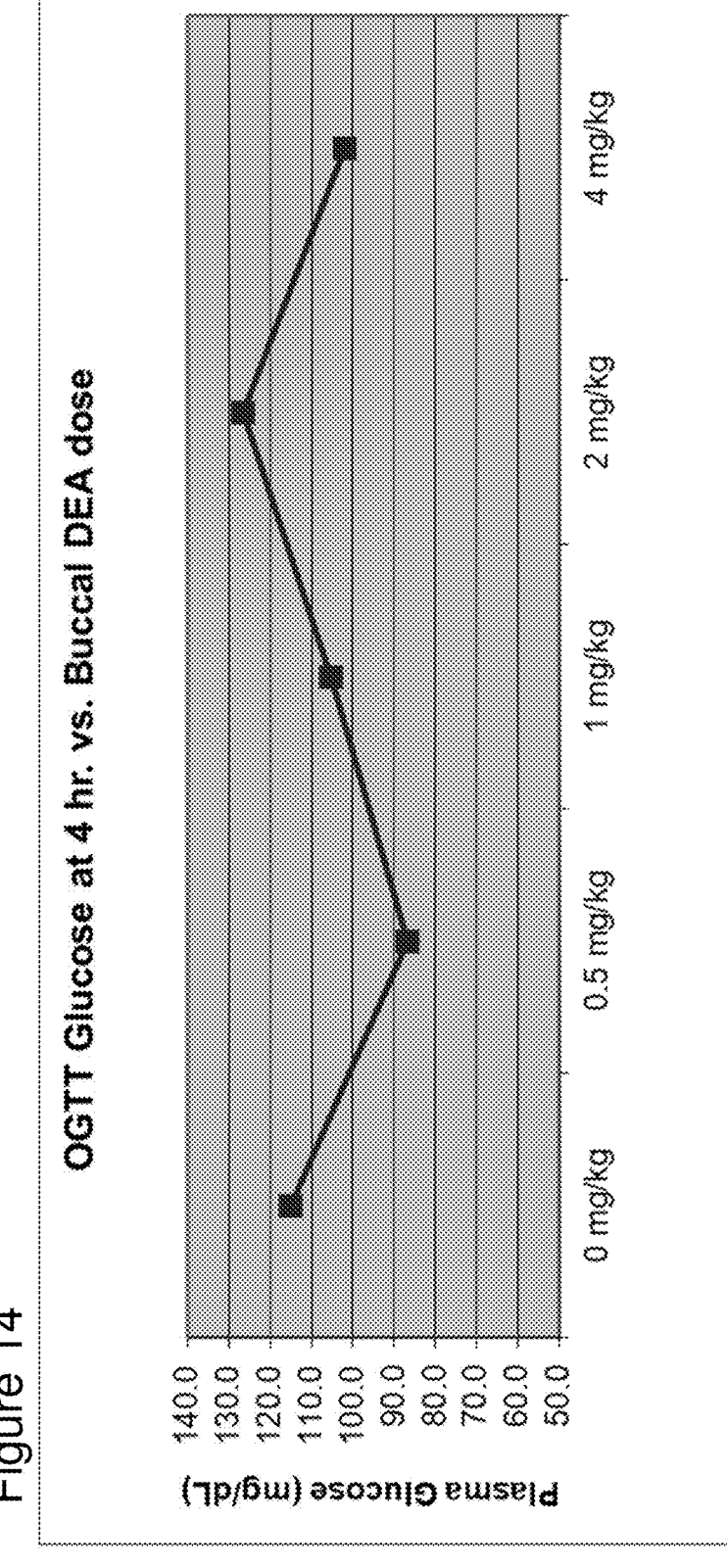
FIG. 14 shows the effect of DEA administration via buccal delivery on plasma glucose concentrations measured four hours after ingestion of a standard glucose dose in an OGTT as a function of the indicated DEA dosages, as described in Example 2.

FIG. 14 shows the effect of buccal delivery of 0 mg/kg, 0.5 mg/kg, 1 mg/kg, 2 mg/kg, and 4 mg/kg of DEA on plasma glucose concentrations (mg/dL) in the setting of (i.e., "during") an OGTT measured at 4 hours after ingestion of 75 grams of glucose in 300 mL volume. The results demonstrate that buccal administration of DEA lowered (improved) plasma glucose levels in the setting of OGTT at the 0.5 mg/kg, 1 mg/kg, and 4 mg/kg DEA dosage amounts DEA dosage amounts, with the more pronounced lowering (improvement) observed at 0.5 mg/kg, 1 mg/kg, and 4 mg/kg DEA dosage amounts.

FIG. 15 shows the effect of buccal DEA delivery (upper panel) and gastric delivery (lower panel) on total cholesterol (TC) levels, high density lipoprotein (HDL) levels, triglyceride levels, calculated low density lipoprotein (Calc LDL) levels, and TC/HDL ratio measured at the indicated DEA dosages (left-most column; DEA dosages in mg/kg). The results demonstrate lowered (i.e., improved) measured TC, triglyceride, and Calc LDL levels, as well as TC/HCL ratio at all tested DEA dosages upon both buccal and gastric delivery of DEA, relative to no DEA administration ("0" mg/kg DEA). The results also demonstrate elevated (i.e., improved) HCL levels at all DEA dosages upon both buccal and gastric delivery of DEA, relative to no DEA administration ("0" mg/kg DEA). More pronounced improvements in the indicated lipid levels and ratios were observed, e.g., at the 1 mg/kg DEA dose upon buccal delivery and at the 0.25 mg/kg DEA dose upon gastric delivery.

FIG. 16 shows the effect of buccal DEA delivery (upper panel) and gastric delivery (lower panel) on plasma glucose levels (in mg/dL) measured at the indicated in the setting of (i.e., "during") an OGTT measured at 0 hour, 1 hour, 2 hours, and 4 hours after ingestion of 75 grams of glucose in 300 mL volume. The results demonstrate lowered (i.e., improved) plasma glucose levels at most tested DEA dosages and post-glucose ingestion time points upon both buccal and gastric delivery of DEA, relative to no DEA administration ("0" mg/kg DEA). More pronounced improvements in plasma glucose levels were observed, e.g., at the 0.5 mg/kg DEA dose upon buccal delivery and at the 0.25 mg/kg DEA dose upon gastric delivery.

FIG. 17 provides a comparison of the indicated measurements of lipid levels (upper panel) and plasma glucose levels (lower panel) at the indicated DEA doses via buccal delivery and gastric delivery (left column), as well as assessment of statistical relevance of differences between delivery mode at for each measurement as determined by Student's paired tow tailed T test, homoskedastic analysis T ("T test"). The results indicate, for example, buccal delivery of DEA resulted in statistically significant greater improvement in total cholesterol and total cholesterol/high density lipoprotein (TC/HDL) ratio relative to improvement observed with gastric delivery of DEA. The results also indicate that. For example, buccal delivery of DEA resulted in significantly significant greater improvement in plasma glucose levels at o hour and 4 hours after ingestion of 75 grams of glucose in 300 mL volume in the setting of OGTT.

REFERENCES

1. Streeper R, Izbicka E, inventors; New Frontier Labs, LLC, assignee. U.S. Pat. No. 10,251,857 B2 Azelaic acid esters in the treatment of insulin resistance. USA 2019.

2. Esposito K, Chiodini P, Colao A, Lenzi A, Giugliano D. Metabolic syndrome and risk of cancer: a systematic review and meta-analysis. Diabetes Care. 2012; 35 (11): 2402-11. Epub 2012 Oct. 25. doi: 35/11/2402 [pii] 10.2337/dc12-0336. PubMed PMID: 23093685; PubMed Central PMCID: PMC3476894.

3. Moghaddam A A, Woodward M, Huxley R. Obesity and risk of colorectal cancer: a meta-analysis of 31 studies with 70,000 events. Cancer Epidemiol Biomarkers Prev. 2007; 16 (12): 2533-47. Epub 2007 Dec. 19. doi: 16/12/2533 [pii] 10.1158/1055-9965.EPI-07-0708. PubMed PMID: 18086756.

4. Huang Y, Cai X, Qiu M, Chen P, Tang H, Hu Y. Prediabetes and the risk of cancer: a meta-analysis. Diabetologia. 2014; 57 (11): 2261-9. Epub 2014 Sep. 12. doi: 10.1007/s00125-014-3361-2. PubMed PMID: 25208757.

5. Koo D, Han K, Park C. The Incremental Risk of Pancreatic Cancer According to Fasting Glucose Levels: Nationwide Population-Based Cohort Study The Journal of Clinical Endocrinologu and Metabollism. 2019; in press.

6. Giovannucci E, Harlan D M, Archer M C, Bergenstal R M, Gapstur S M, Habel L A, et al. Diabetes and cancer: a consensus report. Diabetes Care. 2010; 33 (7): 1674-85. Epub 2010 Jul. 1. doi: 33/7/1674 [pii] 10.2337/dc10-0666. PubMed PMID: 20587728; PubMed Central PMCID: PMC2890380.

7. Hernandez A V, Pasupuleti V, Benites-Zapata V A, Thota P, Deshpande A, Perez-Lopez F R. Insulin resistance and endometrial cancer risk: A systematic review and meta-analysis. Eur J Cancer. 2015; 51 (18): 2747-58. Epub 2015 Nov. 26. doi: S0959-8049 (15) 00851-5 [pii] 10.1016/j.ejca.2015.08.031. PubMed PMID: 26597445.

8. Caputo T, Gilardi F, Desvergne B. From chronic overnutrition to metaflammation and insulin resistance: adipose tissue and liver contributions. FEBS Lett. 2017; 591 (19): 3061-88. Epub 2017 Jul. 6. doi: 10.1002/1873-3468.12742. PubMed PMID: 28677122.

9. Christ A, Latz E. The Western lifestyle has lasting effects on metaflammation. Nat Rev Immunol. 2019; 19 (5): 267-8. Epub 2019 Mar. 27. doi: 10.1038/s41577-019-0156-1 10.1038/s41577-019-0156-1 [pii]. PubMed PMID: 30911129.

10. Boden G, Homko C, Barrero C A, Stein T P, Chen X, Cheung P, et al. Excessive caloric intake acutely causes oxidative stress, GLUT4 carbonylation, and insulin resistance in healthy men. Sci Transl Med. 2015; 7 (304): 304re7. Epub 2015 Sep. 12. doi: 7/304/304re7 [pii] 10.1126/scitranslmed.aac4765. PubMed PMID: 26355033; PubMed Central PMCID: PMC5600191.

11. Lustig R H. Fructose: it's "alcohol without the buzz". Adv Nutr. 2013; 4 (2): 226-35. Epub 2013 Mar. 16. doi: 4/2/226 [pii] 10.3945/an.112.002998. PubMed PMID: 23493539; PubMed Central PMCID: PMC3649103.

12. Shelmet J J, Reichard G A, Skutches C L, Hoeldtke R D, Owen O E, Boden G. Ethanol causes acute inhibition of carbohydrate, fat, and protein oxidation and insulin resistance. J Clin Invest. 1988; 81 (4): 1137-45. Epub 1988 Apr. 1. doi: 10.1172/JCI113428. PubMed PMID: 3280601; PubMed Central PMCID: PMC329642.

13. Kim S J, Ju A, Lim S G, Kim D J. Chronic alcohol consumption, type 2 diabetes mellitus, insulin-like growth factor-I (IGF-I), and growth hormone (GH) in ethanol-treated diabetic rats. Life Sci. 2013; 93 (21): 778-82. Epub 2013 Oct. 3. doi: S0024-3205 (13) 00553-5 [pii] 10.1016/j.lfs.2013.09.018. PubMed PMID: 24084046.

14. Hirakawa M, Arase Y, Amakawa K, Ohmoto-Sekine Y, Ishihara M, Shiba M, et al. Relationship between Alcohol Intake and Risk Factors for Metabolic Syndrome in Men. Intern Med. 2015; 54 (17): 2139-45. Epub 2015 Sep. 4. doi: 10.2169/internalmedicine.54.2736. PubMed PMID: 26328637.

15. Carr R M, Dhir R, Yin X, Agarwal B, Ahima R S. Temporal effects of ethanol consumption on energy homeostasis, hepatic steatosis, and insulin sensitivity in mice. Alcohol Clin Exp Res. 2013; 37 (7): 1091-9. Epub 2013 Feb. 13. doi: 10.1111/acer.12075. PubMed PMID: 23398239; PubMed Central PMCID: PMC3657580.

16. Sterrett J J, Bragg S, Weart C W. Type 2 Diabetes Medication Review. Am J Med Sci. 2016; 351 (4): 342-55. Epub 2016 Apr. 16. doi: S0002-9629 (15) 41058-4 [pii] 10.1016/j.amjms.2016.01.019. PubMed PMID: 27079339.

17. Smilowitz J T, O'Sullivan A, Barile D, German J B, Lonnerdal B, Slupsky C M. The human milk metabolome reveals diverse oligosaccharide profiles. J Nutr. 2013; 143 (11): 1709-18. Epub 2013 Sep. 13. doi: jn.113.178772 [pii] 10.3945/jn. 113.178772. PubMed PMID: 24027187; PubMed Central PMCID: PMC4083237.

18. Matsubara T, Tanaka N, Krausz K W, Manna S K, Kang D W, Anderson E R, et al. Metabolomics identifies an inflammatory cascade involved in dioxin- and diet-induced steatohepatitis. Cell Metab. 2012; 16 (5): 634-44. Epub 2012 Nov. 13. doi: S1550-4131 (12) 00406-8 [pii] 10.1016/j.cmet.2012.10.006. PubMed PMID: 23140643; PubMed Central PMCID: PMC3496181.

19. Fan H, Fan W. Characterization of key odorants in Chinese chixiang aroma-type liquor by gas chromatography-olfactometry, quantitative measurements, aroma recombination, and omission studies. J Agric Food Chem 2015; 63 (14): 3660-8

20. Saerens S M, Delvaux F, Verstrepen K J, Van Dijck P, Thevelein J M, Delvaux F R. Parameters affecting ethyl ester production by Saccharomyces cerevisiae during fermentation. Appl Environ Microbiol. 2008; 74 (2): 454-61. Epub 2007 Nov. 13. doi: 10.1128/AEM.01616-07. PubMed PMID: 17993562; PubMed Central PMCID: PMCPMC2223249.

21. Kostelenos G, Kiritsakis A. Olive tree history and evolution. In: Kiritsakis A, Shahidi F, editors. Olives and olive oil as functional foods. Oxford, UK: John Wiley & Sons Ltd; 2017. p. 1-12.

22. Rahmani M. Food hazards and quality control in table olive processing with a special reference to functional compounds. In: Kiritsakis A, Shahidi F, editors. Olives and olive oil as functional foods. Oxford, UK: John Wiley & Sons Ltd; 2017. p. 347-52.

23. Hymowitz T. The history of the soybean. Soybeans Chemistry, Production, Processing and Utilization: AOCS Press 2008. p. 1-31.

24. Kwon D Y, Daily J W, 3rd, Kim H J, Park S. Antidiabetic effects of fermented soybean products on type 2 diabetes. Nutr Res. 2010; 30 (1): 1-13. Epub 2010 Feb. 2. doi: S0271-5317 (09) 00245-0 [pii] 10.1016/j.nutres.2009.11.004. PubMed PMID: 20116654.

25. Kim J, Chung H. Components in Commercial Douchi a Chinese Fermented Black Bean Product by Supercritical Fluid Extraction. J Food Sci Nutr 2008; 13:12-7.

26. European Food Safety Authority (EFSA). Opinion of the Scientific Panel on Food Additives, Flavourings, Processing Aids and Materials in contact with Food (AFC) on a request from the Commission related to Flavouring Group Evaluation 10: Aliphatic primary and secondary saturated and unsaturated alcohols, aldehydes, acetals, carboxylic acids and esters containing an additional oxygenated functional group and lactones from chemical groups 9, 13 and 30 (Commission Regulation (EC) No 1565/2000 of 18 Jul. 2000) The EFSA Journal 2005; 246:1-110.

27. European Commission. Available from: https://ec.europa.eu/food/safety/food_improvement_agents/additives/database_en.

28. Food and Drug Administration (FDA) of the United States of America. Available from: https://www.accessdata.fda.gov/scripts/cdrh/cfdocs/cfcfr/CFRSearch.cfm?FR=172.515.

29. Food and Drug Administration (FDA) of the United States of America. Available from: https://www.accessdata.fda.gov/scripts/cder/iig/index.cfm?event=BasicSearch.page.

30. Singh B, Saxena A. Surrogate markers of insulin resistance: A review. World J Diabetes. 2010; 1 (2): 36-47. Epub 2011 May 4. doi: 10.4239/wjd.v1.i2.36. PubMed PMID: 21537426; PubMed Central PMCID: PMC3083884.

31. Bonora E, Tuomilehto J. The pros and cons of diagnosing diabetes with A1C. Diabetes Care. 2011; 34 Suppl 2: S184-90. Epub 2011 May 6. doi: 34/Supplement_2/S184 [pii] 10.2337/dc11-s216. PubMed PMID: 21525453; PubMed Central PMCID: PMC3632159.

32. American, Diabetes Association. Diagnosis and classification of diabetes mellitus. Diabetes Care. 2013; 36 Suppl 1: S67-74. Epub 2013 Jan. 4. doi: 10.2337/dc13-S067. PubMed PMID: 23264425; PubMed Central PMCID: PMCPMC3537273.

33. Tyrer S, Heyman B. Sampling in epidemiological research: issues, hazards and pitfalls. BJPsych Bull. 2016; 40 (2): 57-60. Epub 2016 Apr. 19. doi: 10.1192/pb.bp.114.050203. PubMed PMID: 27087985; PubMed Central PMCID: PMCPMC4817645.

34. Yeung E H, Zhang C, Mumford S L, Ye A, Trevisan M, Chen L, et al. Longitudinal study of insulin resistance and sex hormones over the menstrual cycle: the BioCycle Study. J Clin Endocrinol Metab. 2010; 95 (12): 5435-42. Epub 2010 Sep. 17. doi: 10.1210/jc.2010-0702. PubMed PMID: 20843950; PubMed Central PMCID: PMCPMC2999972.

35. Ibrahim M M A, Ghadzi S M S, Kjellsson M C, Karlsson M O. Study Design Selection in Early Clinical Anti-Hyperglycemic Drug Development: A Simulation Study of Glucose Tolerance Tests. CPT Pharmacometrics Syst Pharmacol. 2018; 7 (7): 432-41. Epub 2018 May 8. doi: 10.1002/psp4.12302. PubMed PMID: 29732710; PubMed Central PMCID: PMC6063744.

36. Warnick G, Kimberly M, Waymack P, Leary E. Standardization of Measurements for Cholesterol, Triglycerides, and Major Lipoproteins Labmedicine. 2008; 39 (8).

37. Sherifali D, Nerenberg K, Pullenayegum E, Cheng J E, Gerstein H C. The effect of oral antidiabetic agents on A1C levels: a systematic review and meta-analysis. Diabetes Care. 2010; 33 (8): 1859-64. Epub 2010 May 21. doi: 10.2337/dc09-1727. PubMed PMID: 20484130; PubMed Central PMCID: PMCPMC2909079.

38. Brambilla P, La Valle E, Falbo R, Limonta G, Signorini S, Cappellini F, et al. Normal fasting plasma glucose and risk of type 2 diabetes. Diabetes Care. 2011; 34 (6): 1372-4. Epub 2011 Apr. 19. doi: dc10-2263 [pii] 10.2337/dc10-2263. PubMed PMID: 21498787; PubMed Central PMCID: PMC3114342.

39. Tuso P. Prediabetes and lifestyle modification: time to prevent a preventable disease. Perm J. 2014; 18 (3): 88-93. Epub 2014 Aug. 8. doi: 10.7812/TPP/14-002. PubMed PMID: 25102521; PubMed Central PMCID: PMCPMC4116271.

40. Brunzell J D, Robertson R P, Lerner R L, Hazzard W R, Ensinck J W, Bierman E L, et al. Relationships between fasting plasma glucose levels and insulin secretion during intravenous glucose tolerance tests. J Clin Endocrinol Metab. 1976; 42 (2): 222-9. Epub 1976 Feb. 11. doi: 10.1210/jcem-42-2-222. PubMed PMID: 1262429.

41. Gaitonde P, Garhyan P, Link C, Chien J, Trame M, Schmidt S. A Comprehensive Review of Novel Drug-Disease Models in Diabetes Drug Development. Clinical Pharmacokinetics. 2016; 55 (7): 769-88. doi: https://doi.org/10.1007/s40262-015-0359-y.

42. Thomas M C. Glycemic exposure, glycemic control, and metabolic karma in diabetic complications. Adv Chronic Kidney Dis. 2014; 21 (3): 311-7. Epub 2014 May 2. doi: 10.1053/j.ackd.2014.03.004. PubMed PMID: 24780460.

43. Gerich J E. The importance of tight glycemic control. Am J Med. 2005; 118 (Suppl 9A): 7S-11S. Epub 2005 Oct. 18. doi: 10.1016/j.amjmed.2005.07.051. PubMed PMID: 16224937.

44. Bluher S, Mantzroros C. Leptin in humans: lessons from translational research. American Journal of Clinical Nutrition. 2009; 89 (3): 991S-7S.

45. Wang K, Shan S, Zheng H, Zhao X, Chen C, Liu C. Non-HDL-cholesterol to HDL-cholesterol ratio is a better predictor of new-onset non-alcoholic fatty liver disease than non-HDL-cholesterol: a cohort study. Lipids Health Dis. 2018; 17 (1): 196. Epub 2018 Aug. 23. doi: 10.1186/s12944-018-0848-8. PubMed PMID: 30131058; PubMed Central PMCID: PMCPMC6104008.

46. Donath M Y, Ehses J A, Maedler K, Schumann D M, Ellingsgaard H, Eppler E, et al. Mechanisms of beta-cell death in type 2 diabetes. Diabetes. 2005; 54 Suppl 2: S108-13. Epub 2005 Nov. 25. doi: 10.2337/diabetes.54.suppl_2.s108. PubMed PMID: 16306327.

47. Eriksson A, Attvall S, Bonnier M, Eriksson J W, Rosander B, Karlsson F A. Short-term effects of metformin in type 2 diabetes. Diabetes Obes Metab. 2007; 9 (4): 483-9. Epub 2007 Jun. 26. doi: DOM624 [pii] 10.1111/j.1463-1326.2006.00624.x. PubMed PMID: 17587390.

48. Salpeter S R, Buckley N S, Kahn J A, Salpeter E E. Meta-analysis: metformin treatment in persons at risk for diabetes mellitus. Am J Med. 2008; 121 (2): 149-57 e2. Epub 2008 Feb. 12. doi: S0002-9343 (07) 00988-6 [pii] 10.1016/j.amjmed.2007.09.016. PubMed PMID: 18261504.

49. Group DPPR. Long-term Effects of Metformin on Diabetes Prevention: Identification of Subgroups That Benefited Most in the Diabetes Prevention Program and Diabetes Prevention Program Outcomes Study. Diabetes Care. 2019; 42 (4): 601-8. Epub 2019 Mar. 17. doi: dc18-1970 [pii] 10.2337/dc18-1970. PubMed PMID: 30877090; PubMed Central PMCID: PMC6429636.

50. Streeper R, Izbicka E, inventors; New Frontier Labs LLC, assignee. U.S. Continuation patent application Ser. No. 16/627,338. Azelaic acid esters in the treatment of insulin resistance 2019.

51. Bodmer M, Meier C, Krahenbuhl S, Jick S S, Meier C R. Metformin, sulfonylureas, or other antidiabetes drugs and the risk of lactic acidosis or hypoglycemia: a nested case-control analysis. Diabetes Care. 2008; 31 (11): 2086-91. Epub 2008 Sep. 11. doi: dc08-1171 [pii] 10.2337/dc08-1171. PubMed PMID: 18782901; PubMed Central PMCID: PMC2571051.

52. Lin S H, Cheng P C, Tu S T, Hsu S R, Cheng Y C, Liu Y H. Effect of metformin monotherapy on serum lipid profile in statin-naive individuals with newly diagnosed type 2 diabetes mellitus: a cohort study. PeerJ. 2018; 6: e4578. Epub 2018 Apr. 19. doi: 10.7717/peerj.4578 4578 [pii]. PubMed PMID: 29666753; PubMed Central PMCID: PMC5899882.

53. McCreight L J, Bailey C J, Pearson E R. Metformin and the gastrointestinal tract. Diabetologia. 2016; 59 (3): 426-35. Epub 2016 Jan. 19. doi: 10.1007/s00125-015-3844-9 10.1007/s00125-015-3844-9 [pii]. PubMed PMID: 26780750; PubMed Central PMCID: PMC4742508.

54. Yerevanian A, Soukas A A. Metformin: Mechanisms in Human Obesity and Weight Loss. Curr Obes Rep. 2019; 8 (2): 156-64. Epub 2019 Mar. 16. doi: 10.1007/s13679-019-00335-3. PubMed PMID: 30874963; PubMed Central PMCID: PMCPMC6520185.

55. Luo F, Das A, Chen J, Wu P, Li X, Fang Z. Metformin in patients with and without diabetes: a paradigm shift in cardiovascular disease management. Cardiovasc Diabetol. 2019; 18 (1): 54. Epub 2019 Apr. 29. doi: 10.1186/s12933-019-0860-y. PubMed PMID: 31029144; PubMed Central PMCID: PMCPMC6486984.

56. Courtois S, Lehours P, Bessede E. The therapeutic potential of metformin in gastric cancer. Gastric Cancer. 2019; 22 (4): 653-62. Epub 2019 Mar. 23. doi: 10.1007/s10120-019-00952-w. PubMed PMID: 30900101.

57. Barzilai N, Crandall J P, Kritchevsky S B, Espeland M A. Metformin as a Tool to Target Aging. Cell Metab. 2016; 23 (6): 1060-5. Epub 2016 Jun. 16. doi: 10.1016/j.cmet.2016.05.011. PubMed PMID: 27304507; PubMed Central PMCID: PMCPMC5943638.

58. Kulkarni A S, Brutsaert E F, Anghel V, Zhang K, Bloomgarden N, Pollak M, et al. Metformin regulates metabolic and nonmetabolic pathways in skeletal muscle and subcutaneous adipose tissues of older adults. Aging Cell. 2018; 17 (2). Epub 2018 Feb. 1. doi: 10.1111/acel.12723. PubMed PMID: 29383869; PubMed Central PMCID: PMCPMC5847877.

59. Lemieux I, Lamarche B, Couillard C, Pascot A, Cantin B, Bergeron J, et al. Total cholesterol/HDL cholesterol ratio vs LDL cholesterol/HDL cholesterol ratio as indices of ischemic heart disease risk in men: the Quebec Cardiovascular Study. Arch Intern Med. 2001; 161 (22): 2685-92. Epub 2001 Dec. 26. doi: ioi01029 [pii]. PubMed PMID: 11732933.

60. Wang D, Wang L, Wang Z, Chen S, Ni Y, Jiang D. Higher non-HDL-cholesterol to HDL-cholesterol ratio linked with increased nonalcoholic steatohepatitis. Lipids in Health and Disease. 2018; 17 (1): 67. doi: 10.1186/s12944-018-0720-x.

61. Ertunc M E, Hotamisligil G S. Lipid signaling and lipotoxicity in metaflammation: indications for metabolic disease pathogenesis and treatment. J Lipid Res. 2016; 57 (12): 2099-114. Epub 2016 Jun. 23. doi: 10.1194/jlr.R066514. PubMed PMID: 27330055; PubMed Central PMCID: PMCPMC5321214.

62. Speliotes E K, Balakrishnan M, Friedman L S, Corey K E. Treatment of Dyslipidemia in Common Liver Diseases. Clin Gastroenterol Hepatol. 2018; 16 (8): 1189-96. Epub 2018 Apr. 24. doi: 10.1016/j.cgh.2018.04.023. PubMed PMID: 29684459; PubMed Central PMCID: PMCPMC6558967.

63. Binesh Marvasti T, Adeli K. Pharmacological management of metabolic syndrome and its lipid complications. Daru. 2010; 18 (3): 146-54. Epub 2010 Jan. 1. PubMed PMID: 22615610; PubMed Central PMCID: PMCPMC3304358.

64. Nicholls S J, Tuzcu E M, Sipahi I, Grasso A W, Schoenhagen P, Hu T, et al. Statins, high-density lipoprotein cholesterol, and regression of coronary atherosclerosis. JAMA. 2007; 297 (5): 499-508. Epub 2007 Feb. 8. doi: 10.1001/jama.297.5.499. PubMed PMID: 17284700.

65. Sattar N, Preiss D, Murray H M, Welsh P, Buckley B M, de Craen A J, et al. Statins and risk of incident diabetes: a collaborative meta-analysis of randomised statin trials. Lancet. 2010; 375 (9716): 735-42. Epub 2010 Feb. 20. doi: 10.1016/S0140-6736 (09) 61965-6. PubMed PMID: 20167359.

66. Seshadri S, Rapaka N, Prajapati B, Mandaliya D, Patel S, Muggalla C S, et al. Statins exacerbate glucose intolerance and hyperglycemia in a high sucrose fed rodent model. Sci Rep. 2019; 9 (1): 8825. Epub 2019 Jun. 21. doi: 10.1038/s41598-019-45369-8. PubMed PMID: 31217552; PubMed Central PMCID: PMCPMC6584635.

67. Golomb B A, Evans M A. Statin adverse effects: a review of the literature and evidence for a mitochondrial mechanism. Am J Cardiovasc Drugs. 2008; 8 (6): 373-418. Epub 2009 Jan. 23. doi: 10.2165/0129784-200808060-00004 10.2165/0129784-200808060-00004. PubMed PMID: 19159124; PubMed Central PMCID: PMCPMC2849981.

68. Fessler M B, Parks J S. Intracellular lipid flux and membrane microdomains as organizing principles in inflammatory cell signaling. J Immunol. 2011; 187 (4): 1529-35. Epub 2011 Aug. 4. doi: 187/4/1529 [pii] 10.4049/jimmunol.1100253. PubMed PMID: 21810617; PubMed Central PMCID: PMC3151145.

69. Schoeniger A, Adolph S, Fuhrmann H, Schumann J. The Impact of Membrane Lipid Composition on Macrophage Activation in the Immune Defense against *Rhodococcus equi* and *Pseudomonas aeruginosa*. Int J Mol Sci. 2011; 12 (11): 7510-28. Epub 2011 Dec. 17. doi: 10.3390/ijms12117510 ijms-12-07510 [pii]. PubMed PMID: 22174614; PubMed Central PMCID: PMC3233420.

70. Goluszko P, Nowicki B. Membrane cholesterol: a crucial molecule affecting interactions of microbial pathogens with mammalian cells. Infect Immun. 2005; 73 (12): 7791-6. Epub 2005 Nov. 22. doi: 73/12/7791 [pii] 10.1128/IAI.73.12.7791-7796.2005. PubMed PMID: 16299268; PubMed Central PMCID: PMC1307024.

71. Owen J S, Bruckdorfer K R, Day R C, McIntyre N. Decreased erythrocyte membrane fluidity and altered lipid composition in human liver disease. J Lipid Res. 1982; 23 (1): 124-32. Epub 1982 Jan. 1. PubMed PMID: 7057101.

US 12,605,354 B2

39 being effective at improving one or more abnormal lipid
levels when administered to a subject.

72. Kojima K. Molecular aspects of the plasma membrane in tumor cells. Nagoya J Med Sci. 1993; 56 (1-4): 1-18. Epub 1993 Nov. 1. PubMed PMID: 7898547.
73. Pilon M. Revisiting the membrane-centric view of diabetes. Lipids Health Dis. 2016; 15 (1): 167. Epub 2016 Sep. 28. doi: 10.1186/s12944-016-0342-0 10.1186/s12944-016-0342-0 [pii]. PubMed PMID: 27671740; PubMed Central PMCID: PMC5037885.
74. Lodish H B A, Zipursky S L, et al. Diffusion of Small Molecules across Phospholipid Bilayers. Molecular Cell Biology. 4 ed. New York: W. H. Freeman; 2000.
75. Walter A, Gutknecht J. Permeability of small nonelectrolytes through lipid bilayer membranes. J Membr Biol. 1986; 90 (3): 207-17. Epub 1986 Jan. 1. doi: 10.1007/bf01870127. PubMed PMID: 3735402.

What is claimed is:

1. A pharmaceutical composition formulated for buccal delivery and comprises diethyl azelate in an amount of 0.5 mg/kg, and a buccally acceptable carrier, wherein the composition provides an improvement when compared to a composition containing the same amount of diethyl azelate but formulated for gastric delivery, the improvement in one or more selected from the group consisting of: lowering low-density lipoprotein (LDL) levels; lowering a ratio of cholesterol to high density lipoprotein (HDL), lowering a LDL/HDL ratio; and reducing cholesterol.

2. The pharmaceutical composition of claim 1, wherein the composition is formulated for buccal delivery in a form selected from the group consisting of: a discrete unit dose; a powder; a granule; a solution; a suspension in an aqueous liquid or non-aqueous liquid; an oil-in-water liquid emulsion; and a water-in-oil liquid emulsion, the composition 3. The pharmaceutical composition of claim 1, wherein the amount of diethyl azelate is effective at lowering an elevated low-density lipoprotein (LDL) level, elevating a diminished high-density lipoproteins (HDL) level, lowering an elevated triglyceride level, lowering an elevated cholesterol/HDL, lowering an elevated LDL/HDL, lowering an elevated LDL/triglyceride, or lowering an elevated non-cholesterol HDL/HDL when administered to a subject.

4. The pharmaceutical composition of claim 1, wherein the composition is formulated for buccal delivery in a form selected from the group consisting of tablets, lozenges, pastilles, and gels, the composition being effective at treating or preventing a dyslipidemia, or a disease or condition associated with a dyslipidemia, when administered to a subject.

5. The pharmaceutical composition of claim 1, further comprising a second active ingredient selected from the group consisting of: a $C_1$-$C_4$ alkyl ester azelate other than diethyl azelate (DEA), a biguanide, metformin, buformin, phenformin, a thiazolidinedione, pioglitazone, rosiglitazone, a corticosteroid, prednisone, an insulin, a lipase inhibitor, orlistat, a glucagon-like peptide-1 (GLP-1) agonist, an exendin, exenatide, liraglutide, lixisenatide, albiglutide, dulaglutide, semaglutide, an HMG-COA reductase inhibitor, a statin, atorvastatin, luvastatin, lovastatin, pitavastatin, pravastatin, rusovastatin, simvastatin, a fibrate, gemfibrozil, fenofibrate, niacin, a leptin, a leptin agonist, metreleptin, an amylin agonist, pramlintide, and combinations thereof.

*     *     *     *     *